United States Patent [19]
Coutts et al.

[11] Patent Number: 5,633,395
[45] Date of Patent: May 27, 1997

[54] CHEMICALLY-DEFINED NON-POLYMERIC VALENCY PLATFORM MOLECULES AND CONJUGATES THEREOF

[75] Inventors: Stephen M. Coutts, Rancho Santa Fe; David S. Jones, San Diego; Douglas A. Livingston, San Diego; Lin Yu, San Diego, all of Calif.

[73] Assignee: La Jolla Pharmaceutical Company, San Diego, Calif.

[21] Appl. No.: 453,452

[22] Filed: May 30, 1995

Related U.S. Application Data

[63] Continuation of Ser. No. 152,506, Nov. 15, 1993, Pat. No. 5,552,391, which is a continuation-in-part of Ser. No. 914,869, Jul. 15, 1992, Pat. No. 5,276,013, which is a continuation-in-part of Ser. No. 494,118, Mar. 13, 1990, Pat. No. 5,162,515, which is a continuation-in-part of Ser. No. 466,138, Jan. 16, 1990, abandoned, and Ser. No. 118,055, Sep. 8, 1993, which is a continuation-in-part of Ser. No. 652,648, Feb. 8, 1991, Pat. No. 5,268,454.

[51] Int. Cl.$^6$ ............................................. C07F 9/02
[52] U.S. Cl. ............................................. 558/159
[58] Field of Search ................................. 558/159

[56] References Cited

U.S. PATENT DOCUMENTS

| | | | |
|---|---|---|---|
| 4,191,668 | 3/1980 | Katz | 260/6 |
| 4,220,565 | 9/1980 | Katz | 260/6 |
| 4,650,675 | 3/1987 | Borel et al. | 424/85 |
| 4,751,181 | 6/1988 | Keene | 435/70 |
| 5,126,131 | 6/1992 | Dintzis et al. | 424/88 |
| 5,162,515 | 11/1992 | Conrad et al. | 536/27 |
| 5,276,013 | 1/1994 | Conrad et al. | 514/2 |

FOREIGN PATENT DOCUMENTS

| | | |
|---|---|---|
| WO86/04093 | 7/1986 | WIPO . |
| WO92/11029 | 7/1992 | WIPO . |

OTHER PUBLICATIONS

Borel et al., "Prevention of murine lupus nephritis by carrier-dependent induction of immunologic tolerance to denatured DNA" *Science* (1973) 182:76–78.

Parker et al., "Modification of NZB/NZW F$_1$ autoimmune disease by development of tolerance to DNA" *J. Immunol.* (1974) 113(1):292–297.

Borel et al., "A possible new therapy of systemic lupus erythematosus (SLE)" *Ann. N.Y. Acad. Sci.* (1986) 475:296–306.

Borel et al., "Oligonucleotide linked to human gammaglobulin specifically diminishes anti–DNA antibody formation in cultured lymphoid cells from patients with systemic lupus erythematosus" *J. Clin. Invest.* (1988) 82:1901–1907.

Sasaki et al., "Induction of immunological tolerance to single-stranded and double-stranded DNA" *Scand. J. Immunol.* (1982) 16:191–200.

Sehon, "Suppression of IgE antibody responses with tolerogenic conjugates of allergens and haptens" *Prog. Allergy* (1982) 32:161–202.

Wilkinson et al., "Tolerance induction in mice by conjugates of monoclonal immunoglobulins and monomethoxypolyethylene glycol" *J. Immunol.* (1987) 139:326–331.

Borel et al., "A novel technique to link either proteins or peptides to gammaglobulin to construct tolerogens" *J. Immunol. Methods* (1990) 126:159–168.

Eshhar et al., "Induction of tolerance to nucleic acid determinants by administration of a complex of nucleoside D–glutamic acid and D–lysine (D–GL)" *J. Immunol.* (1975) 144(2):872–876.

Papalian et al., "Reaction of systemic lupus erythematosus antinative DNA antibodies with native DNA fragments from 20 to 1,200 base pairs" *J. Clin. Invest.* (1980) 65:469–477.

Stollar et al., "Secondary structure in denatured DNA is responsible for its reaction with antinative DNA antibodies of systematic lupus erythematosus sera" (1980) 66:210–219.

Agrawal et al., "Efficient methods for attaching non–radioactive labels to the 5' end of synthetic oligonucleotides" *Nucl. Acids Res.* (1987) 14(15):6227–6245.

Kremsky et al., "Immobilization of DNA via oligonucleotides containing an aldehyde or carboxylic acid group at the 5' terminus" *Nucl. Acids Res.* (1987) 15(7):2891–2909.

*Primary Examiner*—John W. Rollins
*Attorney, Agent, or Firm*—Morrison & Foerster LLP

[57] ABSTRACT

Chemically-defined, non-polymeric valency platform molecules and conjugates comprising chemically-defined valency platform molecules and biological or chemical molecules including polynucleotide duplexes of at least 20 base pairs that have significant binding activity for human lupus anti-dsDNA autoantibodies.

1 Claim, 17 Drawing Sheets

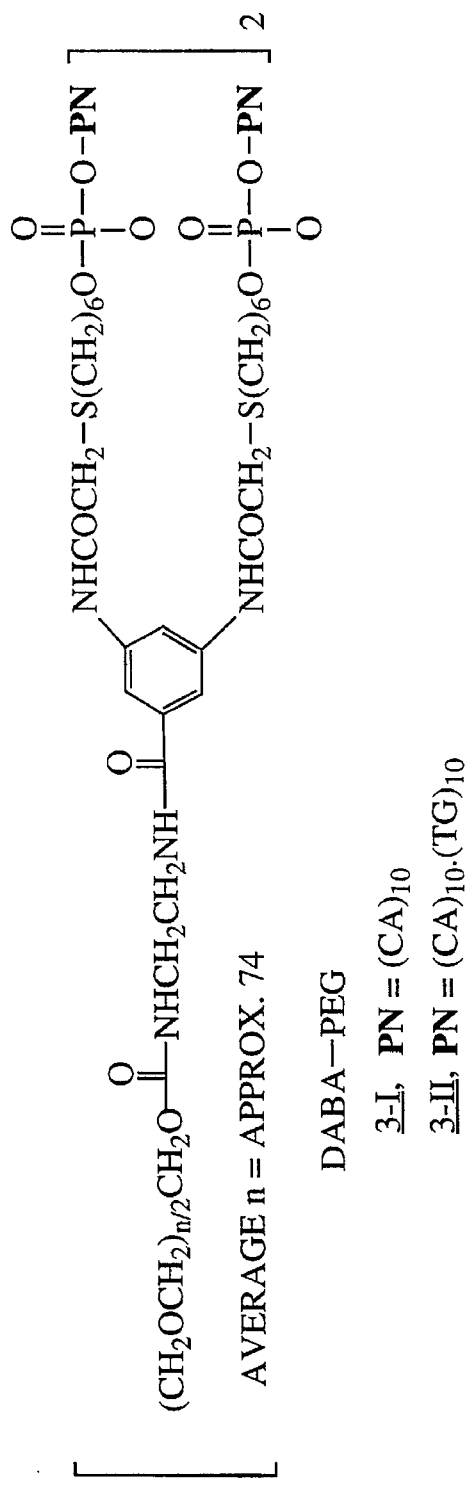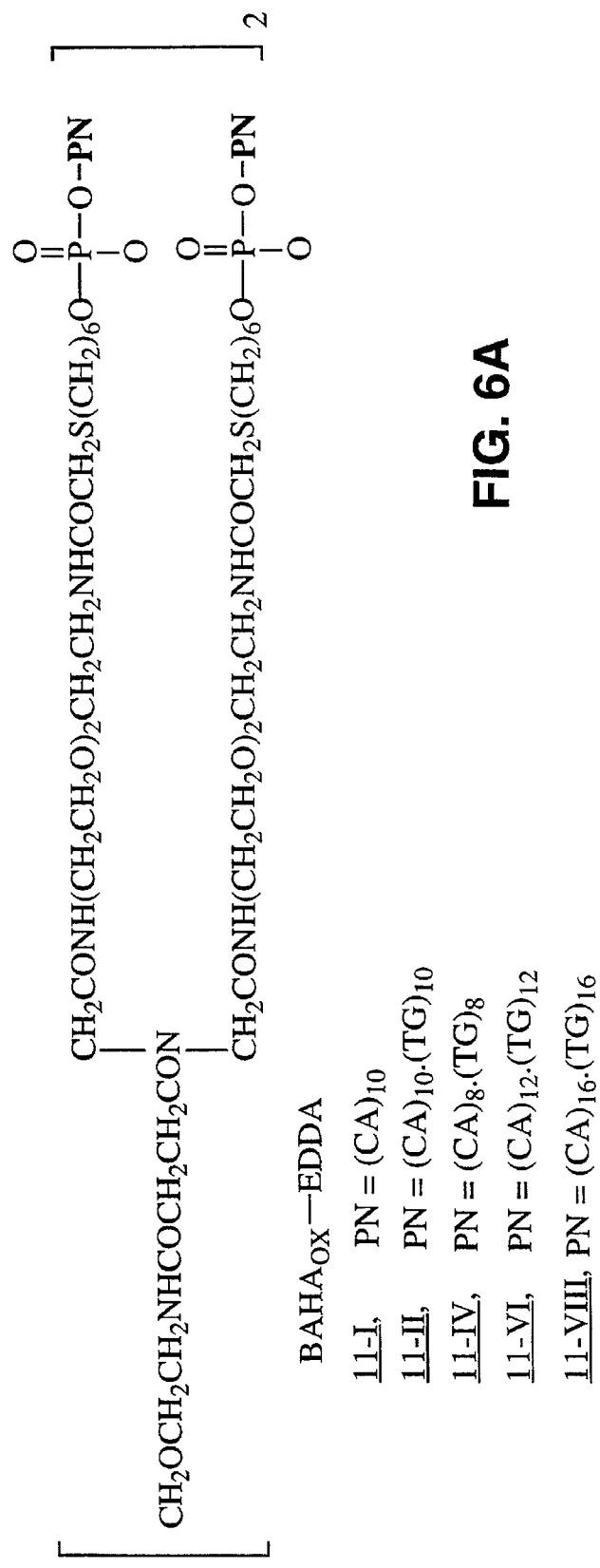
FIG. 6A

HAD—AHAB—TEG

MELITTIN CONJUGATE #1, R = H₂N-Cys-Trp-Ile-Lys-Arg-Lys-Arg-Gln-Gln-Gly-CO₂H
AVERAGE n = APPROX. 74

MELITTIN CONJUGATE #2, R = H₂N-Cys-Trp-Ile-Lys-Arg-Lys-Arg-Gln-Gln-Gly-CO₂H
MELITTIN CONJUGATE #3, R = H₂N-Trp-Ile-Lys-Arg-Lys-Arg-Gln-Gln-Lys-Cys-Gly-CO₂H
MELITTIN CONJUGATE #4, R = H₂N-Cys-Ile-Ser-Trp-Ile-Lys-Arg-Lys-Arg-Gln-Gln-Gly-CO₂H
MELITTIN CONJUGATE #5, R = (H₂N-Trp-Ile-Lys-Arg-Lys-Arg-Gln-Gln)₂-Lys-Cys-Gly-CO₂H

MELITTIN PEPTIDES ATTACHED THROUGH SULFUR ATOM ON ADDED CYSTEINE, AVERAGE N = APPROX. 74

FIG. 13

CHEMICALLY-DEFINED NON-POLYMERIC VALENCY PLATFORM MOLECULES AND CONJUGATES THEREOF

CROSS-REFERENCE TO RELATED APPLICATIONS

This application is a continuation of application Ser. No. 08/152,506 filed Nov. 15, 1993, U.S. Pat. No. 5,552,381 which is a CIP of Ser. No. 07/914,869, filed Jul. 15, 1992, U.S. Pat. No. 5,276,807 which is a CIP of Ser. No. 07/494,118, filed Mar. 13, 1990, now U.S. Pat. No. 5,162,515, which is a CIP of Ser. No. 07/466,138, filed Jan. 16, 1990, abandoned, and a CIP of Ser. No. 08/118,055, filed Sep. 8, 1993, which is a CIP of Ser. No. 07/652,648, filed Feb. 8, 1991, now U.S. Pat. No. 5,268,454.

TECHNICAL FIELD

This invention relates to conjugates comprising chemically-defined, non-polymeric valency platform molecules coupled to biological or chemical molecules such as polynucleotides for treating diseases such as the autoimmune disease systemic lupus erythematosus (SLE or "lupus"). This invention also relates to the chemically-defined, non-polymeric valency platform molecules.

BACKGROUND

A number of compounds have been employed as carriers for biologically useful molecules in preparing conjugates that are alleged to be tolerogenic. For example, Benacerraf, Katz, and their colleagues investigated and described the use of conjugates of the random co-polymer D-glutamic acid/D-lysine, referred to as D-GL in earlier literature (hereinafter D-EK) with haptens and various antigens to induce specific immune tolerance. See U.S. Pats. Nos. 4,191,668 and 4,220,565.

Other investigators have studied conjugates of nucleosides or DNA with other carriers. Borel et al. (*Science* (1973) 182:76) evaluated the ability of isogenic mouse IgG-nucleoside conjugates to reduce the antibody response to denatured DNA in young animals of the NZB mouse strain. In separate studies Parker et al. (*J. Immunol.* (1974) 113:292) evaluated the effect of denatured DNA conjugated to poly-D-lysine and/or cyclophosphamide on the progression of the above-described syndrome in NZB mice.

In a later article (*Ann NY Acad Sci* (1986) 475:296-306) Borel et al. describe oligonucleotide-immunoglobulin conjugates. Borel et al. (*J Clin Invest* (1988) 82:1901-1907 or U.S. Pat. No. 4,650,675) have described in vitro studies using conjugates of human immunoglobulin linked to DNA. U.S. Pat. No. 5,126,131 (Dintzis et al.) also relates to conjugates comprising carriers and molecules involved in immune responses.

Other references describe conjugates of nonimmunogenic polymers and immunogens (Sasaki et al., *Scand. J. Immun.* (1982) 16:191-200; Sehon, *Prog. Allergy* (1982) 32:161-202; Wilkinson et al., *J. Immunol.* (1987) 139:326-331, and Borel et al., *J. Immunol. Methods* (1990) 126:159-168).

In commonly-owned U.S. Ser. No. 07/914,869, U.S. Pat. Nos. 5,162,515, and 07/652,658, conjugates comprising polymeric carriers such as D-EK, polyethylene glycol, poly-D-lysine, polyvinyl alcohol, polyvinyl pyrrolidone and immunoglobulins are described.

In sum, applicants believe that the prior art shows only ill-defined chemical compounds or compounds with numerous non-specific attachment sites employed as valency platform molecules in conjugates. Because the valency of such compounds, the specific location of the attachment sites, and the number of attachment sites are unpredictable and fluctuate widely, prior art conjugates comprising such compounds cannot be made reproducibly and show wide ranges in their reported activity.

DISCLOSURE OF THE INVENTION

In contrast to the above-described art, applicants have developed conjugates comprising chemically-defined, non-polymeric valency platform molecules wherein the valency of the platform molecules is predetermined and wherein each attachment site is available for binding of a biological or synthetic molecule. Valency platform molecules within the present invention are defined with respect to their chemical structure, valency, homogeneity and a defined chemistry which is amenable to effective conjugation with the appropriate biological and/or synthetic molecules.

Thus, one aspect of the instant invention is directed to conjugates comprising the chemically-defined, non-polymeric valency platform molecules and biological and/or chemical molecules. Exemplary of biological and/or chemical molecules suitable for conjugation to chemically-defined, non-polymeric valency platform molecules to form conjugates within the instant invention are carbohydrates, drugs, lipids, lipopolysaccharides, peptides, proteins, glycoproteins, single-stranded or double-stranded oligonucleotides and chemical analogs thereof, analogs of immunogens, haptens, mimotopes, aptamers and the like. Chemically-defined, non-polymeric valency platform molecules suitable for use within the present invention include, but are not limited to, derivatives of biologically compatible and nonimmunogenic carbon-based compounds of the following formulae:

Formula 1

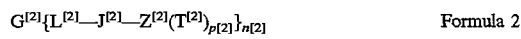

Formula 2 wherein each of $G^{[1]}$ and $G^{[1]}$, if present, is independently a linear, branched or multiply-branched chain comprising 1–2000, more preferably 1–1000, chain atoms selected from the group C, N, O, Si, P and S;

more preferably, $G^{[2]}$, if present, is a radical derived from a polyalcohol, a polyamine, or a polyether; most preferably, $G^{[2]}$ is selected from the group $—(CH_2)_q—$ wherein q=0 to 20, $—CH_2(CH_2OCH_2)_rCH_2—$, wherein r=0 to 300, and $C(CH_2OCH_2CH_2—)_s(CH_2OH)_{4-s}$ wherein s=1 to 4, more preferably s=3 to 4;

each of the $n^{[1]}$ moieties shown as $T^{[1]}$ and each of the $p^{[2]} \times n^{[2]}$ moieties shown as $T^{[2]}$ is independently chosen from the group $NHR^{SUB}$ (amine), $C(=O)NHNHR^{SUB}$ (hydrazide), $NHNHR^{SUB}$ (hydrazine), $C(=O)OH$ (carboxylic acid), $C(=O)OR^{ESTER}$ (activated ester), $C(=O)OC(=O)R^B$ (anhydride), $C(=O)X$ (acid halide), $S(=O)_2X$ (sulfonyl halide), $C(=NR^{SUB})OR^{SUB}$ (imidate ester), NCO (isocyanate), NCS (isothiocyanate), $OC(=O)X$ (haloformate), $C(=O)$ $OC(=NR^{SUB})NHR^{SUB}$ (carbodiimide adduct), $C(=O)H$ (aldehyde), $C(=O)R^B$ (ketone), SH (sulfhydryl or thiol), OH (alcohol), $C(=O)CH_2X$ (haloacetyl), $R^{ALK}X$ (alkyl halide), $S(=O)_2OR^{ALK}X$ (alkyl sulfonate), $NR^1R^2$ wherein $R^1R^2$ is $—C(=O)CH=CHC(=O)—$ (maleimide), $C(=O)CR^B=CR^B_2$ (α,β-unsaturated carbonyl), $R^{ALK}—Hg—X$ (alkyl mercurial), and $S(=O)CR^B=CR^B_2$ (α,β-unsaturated sulfone);

more preferably each of the $n^{[1]}$ moieties shown as $T^{[1]}$ and each of the $p^{[2]} \times n^{[2]}$ moieties shown as $T^{[2]}$ is independently chosen from the group $NHR^{SUB}$ (amine), $C(=O)CH_2X$ (haloacetyl), $R^{ALK}X$ (alkyl halide), $S(=O)_2OR^{ALK}X$ (alkyl sulfonate), $NR^1R^2$ wherein $R^1R^2$ is $-C(=O)CH=CHC(=O)-$ (maleimide), $C(=O)CR^B=CR^B{}_2$ ($\alpha,\beta$-unsaturated carbonyl), $R^{ALK}-Hg-X$ (alkyl mercurial), and $S(=O)CR^B=CR^B{}_2$ ($\alpha,\beta$-unsaturated sulfone);

even more preferably each of the $n^{[1]}$ moieties shown as $T^{[1]}$ and each of the $p^{[2]} \times n^{[2]}$ moieties shown as $T^{[2]}$ is independently chosen from the group $NHR^{SUB}$ (amine), $C(=O)CH_2X$ (haloacetyl), $NR^1R^2$ wherein $R^1R^2$ is $-C(=O)CH=CHC(=O)-$ (maleimide), and $C(=O)CR^B=CR^B{}_2$ ($\alpha,\beta$-unsaturated carbonyl);

most preferably, all of the $n^{[1]}$ moieties shown as $T^{[1]}$ and all of the $p^{[2]} \times n^{[2]}$ moieties shown as $T^{[2]}$ are identical; wherein each X is independently a halogen of atomic number greater than 16 and less than 54 or other good leaving group (i.e., weak bases such as alkyl or alkyl-substituted sulfonates or sulfates and the like, aryl or aryl-substituted sulfonates or sulfates and the like that act similarly to a halogen in this setting);

each $R^{ALK}$ is independently a linear, branched, or cyclic alkyl (1-20C) group;

each $R^{SUB}$ is independently H, linear, branched, or cyclic alkyl (1-20C), aryl (6-20C), or alkaryl (7-30C);

each $R^{ESTER}$ is independently N-succinimidyl, p-nitrophenyl, pentafluorophenyl, tetrafluorophenyl, pentachlorophenyl, 2,4,5-trichlorophenyl, 2,4-dinitrophenyl, cyanomethyl and the like, or other activating group such as 5-chloro,8-quinolone-1-yl, 1-piperidyl, 1-benzotriazolyl and the like;

each $R^B$ is independently a radical comprising 1–50 atoms selected from the group C, H, N, O, Si, P and S;

each of the $n^{[2]}$ moieties shown as $L^{[1]}$, if present, is independently chosen from the group O, $NR^{SUB}$ and S;

each of the $n^{[2]}$ moieties shown as $J^{[2]}$, if present, is independently chosen from the group $C(=O)$ and $C(=S)$;

$n^{[1]}$=1 to 32, more preferably $n^{[1]}$=2 to 16, even more preferably $n^{[3]}$=2 to 8, most preferably $n^{[1]}$=2 to 4;

$n^{[2]}$=1 to 32, more preferably $n^{[2]}$=1 to 16, even more preferably $n^{[2]}$=1 to 8, yet more preferably $n^{[2]}$=1 to 4, most preferably $n^{[2]}$=1 to 2;

$p^{[2]}$=1 to 8, more preferably $p^{[2]}$=1 to 4, most preferably $p^{[2]}$=1 to 2;

with the proviso that the product $n^{[2]} \times p^{[2]}$ be greater than 1 and less than 33;

each of the $n^{[2]}$ moieties shown as $Z^{[2]}$ is independently a radical comprising 1–200 atoms selected from the group C, H, N, O, Si, P and S, containing attachment sites for at least $p^{[2]}$ functional groups on alkyl, alkenyl, or aromatic carbon atoms;

more preferably, all of the $n^{[2]}$ moieties shown as $Z^{[2]}$ are identical;

more preferably, each of the $n^{[2]}$ moieties shown as $Z^{[2]}$ is independently described by a formula chosen from the group:

| | |
|---|---|
| $Z^{[2]}$ is $W^{[3]}-Y^{[3]}$(attachment site)$_{p[2]}$ | Formula 3 |
| $Z^{[2]}$ is $W^{[4]}-N\{Y^{[4]}$(attachment site)$_{p[2]/2}\}_2$ | Formula 4 |
| $Z^{[2]}$ is $W^{[5]}-CH\{Y^{[5]}$(attachment site)$_{p[2]/2}\}_2$ | Formula 5 | wherein each of the $n^{[2]}$ moieties shown as $W^{[3]}$, $W^{[4]}$, or $W^{[5]}$, if present, is independently a radical comprising 1–100 atoms selected from the group C, H, N, O, Si, P and S;

each of the $n^{[2]}$ moieties shown as $Y^{[3]}$, each of the $2 \times n^{[2]}$ moieties shown as $Y^{[4]}$, and each of the $2 \times n^{[2]}$ moieties shown as $Y^{[5]}$ is independently a radical comprising 1–100 atoms selected from the group C, H, N, O, Si, P and S, containing attachment sites for at least $p^{[2]}$ (for $Y^{[3]}$) or $p^{[2]}/2$ (for $Y^{[4]}$ and $Y^{[5]}$ where $p^{[2]}/2$ is an integer) functional groups on alkyl, alkenyl, or aromatic carbon atoms;

more preferably, each of the $n^{[2]}$ moieties shown as $W^{[3]}$, if present, is independently chosen from the group $(CH_2)_r$, $(CH_2CH_2O)_r$, $NR^{SUB}(CH_2CH_2O)_rCH_2CH_2$, and $NR^{SUB}(CH_2)_rNR^{SUB}C(=O)$, wherein r=1 to 10;

more preferably, each of the $n^{[2]}$ moieties shown as $Y^{[3]}$ is independently linear, branched, or cyclic alkyl (1-20C), aryl (6-20C), or alkaryl (7-30C); most preferably, each of the $n^{[2]}$ moieties shown as $Y^{[3]}$ is independently chosen from the group $C_6H_4$ (phenyl-1,4-diradical), $C_6H_3$ (phenyl-1,3,5-triradical), and $(CH_2)_r$ wherein r=1 to 10;

more preferably, each of the $n^{[2]}$ moieties shown as $W^{[4]}$, if present, is independently chosen from the group $(CH_2)_rC(=O)$ and $(CH_2)_rNR^{SUB}C(=O)$, wherein r=1 to 10;

more preferably, each of the $2 \times n^{[2]}$ moieties shown as $Y^{[4]}$, is independently chosen from the group $(CH_2)_r$, $(CH_2)_rNR^{SUB}C(=O)$ $(CH_2)_q$, $(CH_2)_rC(=O)NR^{SUB}(CH_2)_q$, $(CH_2)_rR^{SUB}C(=O)$ $(CH_2)_qNR^{SUB}C(=O)$ $(CH_2)_r$, $(CH_2)_rC(=O)NR^{SUB}(CH_2)_qNR^{SUB}C(=O)$ $(CH_2)_r$, $(CH_2)_rNR^{SUB}C(=O)$ $(CH_2CH_2O)_qCH_2CH_2$, and $(CH_2)_rC(=O)NR^{SUB}(CH_2CH_2O)_qCH_2CH_2$, wherein r=1 to 10, more preferably r=2 to 6, and q=1 to 10, more preferably q=1 to 3;

more preferably, each of the $n^{[2]}$ moieties shown as $W^{[5]}$, if present, is independently chosen from the group $(CH_2)_rC(=O)$ $NR^{SUB}$ and $(CH_2)_rNR^{SUB}C(=O)NR^{SUB}$, wherein r=1 to 10;

more preferably, each of the $2 \times n^{[2]}$ moieties shown as $Y^{[5]}$, is independently chosen from the group $(CH_2)_r$ and $(CH_2)_rC(=O)NR^{SUB}(CH_2)_q$, wherein r=1 to 10 and q=1 to 10.

In a further preferred embodiment for treating lupus, a conjugate comprises a chemically-defined, non-polymeric valency platform molecule and a multiplicity of polynucleotide duplexes of at least about 20 base pairs each bound to the platform molecule, and having significant binding activity for human SLE anti-dsDNA autoantibodies. In these preferred embodiments, the polynucleotide duplexes are substantially homogeneous in length and one strand of the duplex is conjugated to the valency platform molecule either directly or via a linker molecule. Usually synthetic polynucleotides are coupled to a linker molecule before being coupled to a valency platform molecule. Usually the linker containing strand of the duplex is coupled at or proximate (i.e. within about 5 base pairs) one of its ends such that each strand forms a pendant chain of at least about 20 base pairs measured from the site of attachment of the strand to the linker molecule. The second strand is then annealed to the first strand to form a duplex. Thus, a conjugate within the present invention can be generally described by the following formula:

[(PN)$_n$-linker]$_m$-valency platform molecule.

wherein PN=a double stranded polynucleotide with "n" nucleotides, wherein n=at least about 20, and m=2–8.

Exemplary of suitable linker molecules within the present invention are 6 carbon thiols such as HAD, a thio-6 carbon chain phosphate, and HAD$_p$S, a thio-6 carbon chain phosphorothioate. Chemically-defined valency platform molecules within the present invention are formed, for example, by reacting amino modified-PEG with 3,5-bis-(iodoacetamido) benzoyl chloride (hereinafter "IA-DABA"); 3-carboxypropionamide-N,N-bis-[(6,-N'-carbobenzyloxyaminohexyl)acetamide] 4"-nitrophenyl ester (hereinafter "BAHA"); 3-carboxypropionamide-N,N-bis-[(8'-N'-carbobenzyloxyamino-3',6'-dioxaoctyl)acetamide] 4"-nitrophenyl ester (hereinafter "BAHA$_{ox}$"); or by reacting PEG-bis-chloroformate with N,N-di(2-[6'-N'-carbobenzyloxyaminohexanoamido]ethyl)amine (hereinafter "AHAB") to form chemically-defined valency platform molecules.

Surprisingly unexpected results of at least approximately ten fold up to more than one-hundred fold increase in immunosuppression are achieved using conjugates comprising the chemically-defined, non-polymeric valency platform molecules of the instant invention and biological or synthetic molecules (non-haptens) when compared to the polymeric carriers described in the prior art. For example, at least a one hundred-fold increase in the immunosuppression of anti-dsDNA autoantibodies was achieved as described herein using conjugates within the present invention comprising chemically-defined, non-polymeric valency platform molecules when compared to conjugates comprising an ill-defined carrier described in the prior art.

Still another aspect is a conjugate of (a) a chemically-defined, non-polymeric valency platform molecule and (b) a multiplicity of polynucleotide duplexes each and all of which is bound to the valency platform molecule by a functional group located at or proximate a terminus of one of the strands of the duplex, said conjugate being a human SLE tolerogen.

Pharmaceutical compositions of the above-described conjugates and pharmaceutically acceptable vehicles are another aspect of the invention.

A further aspect of the invention is a method for treating SLE in an individual in need of such treatment comprising administering to the individual an effective amount of the above-described conjugates.

Yet another aspect of the invention is a method of inducing specific B cell anergy to an immunogen in an individual comprising administering to the individual an effective amount of the above-described conjugates.

Another aspect of the invention is a method of treating an individual for an antibody-mediated pathology in which undesired antibodies are produced in response to an immunogen comprising administering to the individual an effective amount of the above-described conjugates.

A further aspect of the invention is a method for making the conjugates described above comprising: covalently bonding the biological or chemical molecule to a chemically-defined valency platform molecule to form a conjugate.

A further aspect of the invention is a method for making the conjugates for treating SLE described above comprising: reacting a multiplicity of single-stranded polynucleotides each of which is at least about 20 nucleotides in length and has a functional group at or proximate one of its termini that reacts with functional groups on the chemically-defined valency platform molecule to form a conjugate, and annealing complementary single-stranded polynucleotides to the single-stranded polynucleotides conjugated to the chemically-defined valency platform molecule to form pendant chains of double-stranded DNA.

Yet another aspect of the invention is directed to novel chemically-defined, non-polymeric valency platform molecules of the formulae:

$$G^{[6]}\{O—C(=O)—NR^{SUB}—Q^{[6]}(T^{[6]})_{p[6]}\}_{n[6]} \qquad \text{Formula 6}$$

or $$G^{[7]}\{O—C(=O)—N[Q^{[7]}(T^{[7]})_{p[7]/2}]_2\}_{n[7]} \qquad \text{Formula 7}$$

wherein each of $G^{[6]}$ and $G^{[7]}$, if present, is independently a linear, branched or multiply-branched chain comprising 1–2000, more preferably 1–1000, chain atoms selected from the group C, N, O, Si, P and S; more preferably, each of $G^{[6]}$ and $G^{[7]}$ is a radical derived from a polyalcohol, a polyamine, or a polyglycol; most preferably, each of $G^{[6]}$ and $G^{[7]}$ is selected from the group $—(CH_2)_q—$ wherein q=0 to 20, $—CH_2(CH_2OCH_2)_rCH_2—$, wherein r=0 to 300, and $C(CH_2OCH_2CH_2—)_s(CH_2OH)_{4s}$ wherein s=1 to 4, more preferably s=3 to 4;

each of the $n^{[6]}\times p^{[6]}$ moieties shown as $T^{[6]}$ and each of the $n^{[7]}\times p^{[7]}$ moieties shown as $T^{[7]}$ is independently chosen from the group $NHR^{SUB}$ (amine), $C(=O)NHNHR^{SUB}$ (hydrazide), $NHNHR^{SUB}$ (hydrazine), $C(=O)OH$ (carboxylic acid), $C(=O)OR^{ESTER}$ (activated ester), $C(=O)OC(=O)R^B$ (anhydride), $C(=O)X$ (acid halide), $S(=O)_2X$ (sulfonyl halide), $C(=NR^{SUB})OR^{SUB}$ (imidate ester), NCO (isocyanate), NCS (isothiocyanate), $OC(=O)X$ (haloformate), $C(=O)OC(=NR^{SUB})NHR^{SUB}$ (carbodiimide adduct), $C(=O)H$ (aldehyde), $C(=O)R^B$ (ketone), SH (sulfhydryl or thiol), OH (alcohol), $C(=O)CH_2X$ (haloacetyl), $R^{ALK}X$ (alkyl halide), $S(=O)_2OR^{ALK}X$ (alkyl sulfonate), $NR^1R^2$ wherein $R^1R^2$ is $—C(=O)CHCHC(=O)—$ (maleimide) $C(=O)CR^B=CR^B_2$ (α,β-unsaturated carbonyl) $R^{ALK}—Hg—X$ (alkyl mercurial) and $S(=O)CR^B=CR^B_2$ (α,β-unsaturated sulfone);

more preferably, each of the $n^{[6]}\times p^{[6]}$ moieties shown as $T^{[6]}$ and each of the $n^{[7]}\times p^{[7]}$ moieties shown as $T^{[7]}$ is independently chosen from the group $NHR^{SUB}$ (amine), $C(=O)CH_2X$ (haloacetyl), $R^{ALK}X$ (alkyl halide), $S(=O)_2OR^{ALK}X$ (alkyl sulfonate), $NR^1R^2$ wherein $R^1R^2$ is $—C(=O)CH=CHC(=O)—$ (maleimide) $C(=O)CR^B=CR^B_2$ (α,β-unsaturated carbonyl) $R^{ALK}—Hg—X$ (alkyl mercurial) and $S(=O)CR^B=CR^B_2$ (α,β-unsaturated sulfone);

even more preferably each of the $n^{[6]}\times p^{[6]}$ moieties shown as $T^{[6]}$ and each of the $n^{[7]}\times p^{[7]}$ moieties shown as $T^{[7]}$ is independently chosen from the group $NHR^{SUB}$ (amine), $C(=O)CH_2X$ (haloacetyl), $NR^1R^2$ wherein $R^1R^2$ is $—C(=O)CH=CHC(=O)—$ (maleimide) and $C(=O)CR^B=CR^B_2$ (α,β-unsaturated carbonyl);

most preferably, all of the $n^{[6]}\times p^{[6]}$ moieties shown as $T^{[6]}$ and all of the $n^{[7]}\times p^{[7]}$ moieties shown as $T^{[7]}$ are identical; wherein each X is independently a halogen of atomic number greater than 16 and less than 54 or other good leaving group;

each $R^{ALK}$ is independently a linear, branched, or cyclic alkyl (1-20C) group;

each $R^{SUB}$ is independently H, linear, branched, or cyclic alkyl (1-20C), aryl(6-20C), or alkaryl (27-30C);

each $R^{ESTER}$ is independently N-succinimidyl, p-nitrophenyl, pentafluorophenyl, tetrafluorophenyl, pentachlorophenyl, 2,4,5-trichlorophenyl, 2,4-dinitrophenyl, cyanomethyl and the like, or other activating group;

each $R^B$ is independently a radical comprising 1–50 atoms selected from the group C, H, N, O, Si, P and S;

$n^{[6]}$=1 to 32, more preferably $n^{[6]}$=1 to 16, even more preferably $n^{[6]}$=1 to 8, yet more preferably $n^{[6]}$=1 to 4, most preferably $n^{[6]}$=1 to 2;

$p^{[6]}$=1 to 8, more preferably $p^{[6]}$=1 to 4, most preferably $p^{[6]}$=1 to 2;

with the proviso that the product $n^{[6]}\times p^{[6]}$ be greater than 1 and less than 33;

n[7]=1 to 32, more preferably n[7]=1 to 16, even more preferably n[7]=1 to 8, yet more preferably n[7]=1 to 4, most preferably n[7]=1 to 2;

p[7]=1 to 8, more preferably p[7]=1 to 4, most preferably p[7]=1 to 2;

with the proviso that the product n[7]×p[7] be greater than 1 and less than 33;

each of the n[6] moieties shown as $Q^{[6]}$ and each of the 2×n[7] moieties shown as $Q^{[7]}$ is independently a radical comprising 1–100 atoms selected from the group C, H, N, O, Si, P and S, containing attachment sites for at least p[6] (for $Q^{[6]}$) or p[7]/2 (for $Q^{[7]}$, where p[7]/2 is an integer) functional groups on alkyl, alkenyl, or aromatic carbon atoms;

more preferably, all of the n[6] moieties shown as $Q^{[6]}$ are identical;

more preferably, all of the 2×n[7] moieties shown as $Q^{[7]}$ are identical;

more preferably, each of the n[6] moieties shown as $Q^{[6]}$, is independently chosen from the group $CH[(CH_2)_r$ (attachment site)$]_2$ and $CH[(CH_2)_rC(=O)NR^{SUB}(CH_2)_q$ (attachment site)$]_2$, wherein r=1 to 10 and q=1 to 10;

more preferably, each of the 2×n[7] moieties shown as $Q^{[7]}$, is independently chosen from the group $(CH_2)_r$, $(CH_2)_rNR^{SUB}C(=O)(CH_2)_q$, $(CH_2)_rC(=O)NR^{SUB}(CH_2)_q$, $(CH_2)_rNR^{SUB}C(=O)$ $(CH_2)_qNR^{SUB}C(=O)$ $(CH_2)_r$, $(CH_2)_rC(=O)NR^{SUB}(CH_2)_qNR^{SUB}C(=O)$ $(CH_2)_r$, $(CH_2)_rNR^{SUB}C(=O)$ $(CH_2CH_2O)_qCH_2CH_2$, and $(CH_2)_rC(=O)NR^{SUB}(CH_2CH_2O)_qCH_2CH_2$, wherein r=1 to 10, more preferably r=2 to 6, and q=1 to 10, more preferably q=1 to 3.

BRIEF DESCRIPTION OF THE DRAWINGS

FIGS. 6A–C show the structure of the derivatized valency platform molecule and the linker coupling the polynucleotide to the platform molecule for Conjugates 3-I, 3-II, 11-I, 11-II, 11-IV, 11-VI, 11-VIII, 17-I, 17-II, 20-I, 20-II, 20-III, and 20-IV.

FIG. 13 illustrates melittin conjugates within the present invention.

MODES FOR CARRYING OUT THE INVENTION

Figure 1:
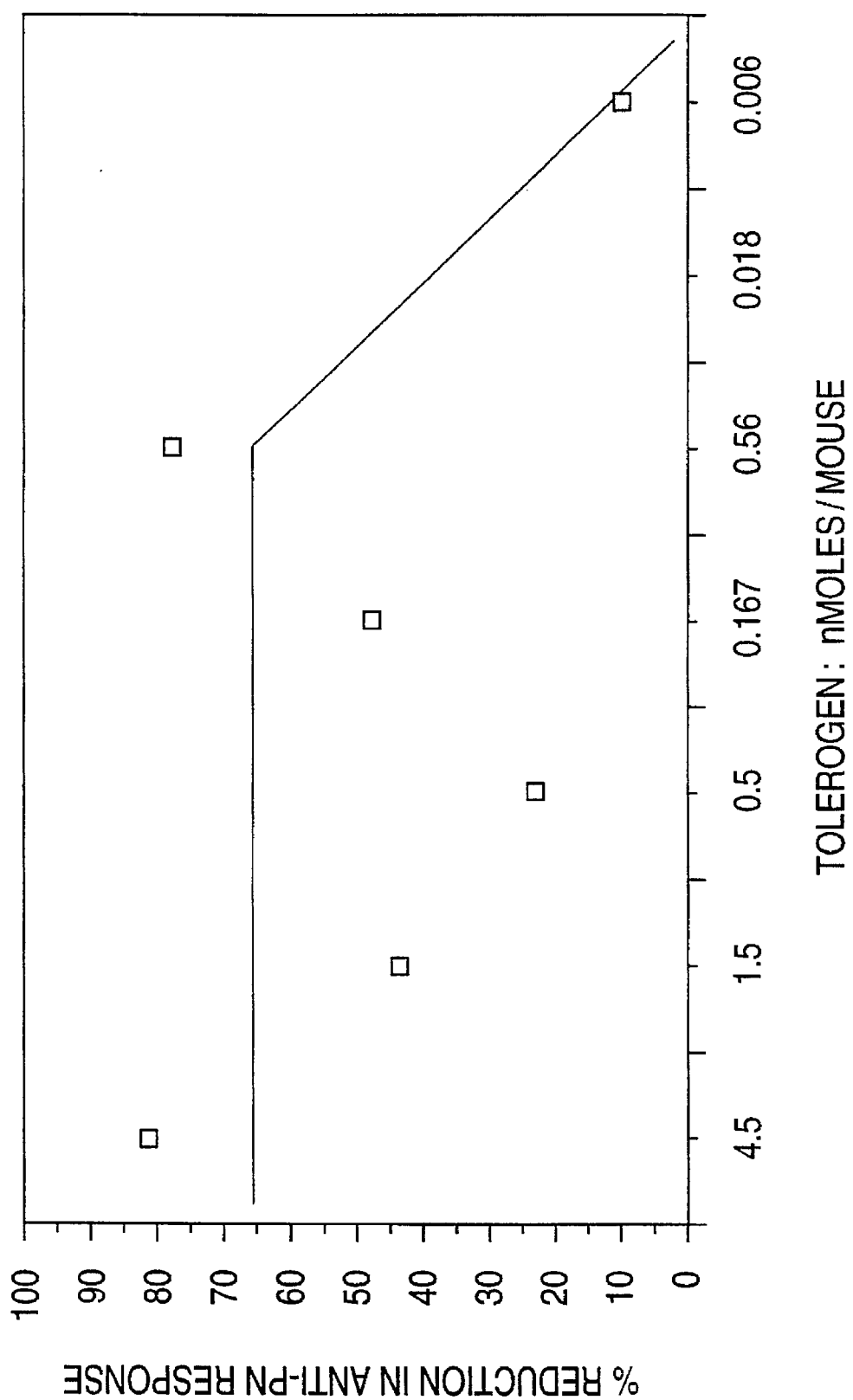
FIG. 1 shows the anti-PN response in mice primed with PN-KLH, treated with [(PN)$_{20}$-BAHA]-EDDA, Conjugate 17-II, in the doses shown or with saline, which were given a booster injection of PN-KLH and then bled 5 days later. Sera were tested at 3 dilutions by the Farr assay using radiolabeled PN at $10^{-8}$M and the data are presented as the percentage reduction of anti-PN antibodies. There were 5 mice per group.

As used herein "valency platform molecule" means a chemically-defined, non-polymeric, nonimmunogenic molecule containing sites which facilitate the attachment of a discreet number of biological and/or chemical molecules.

"Nonimmunogenic" is used to describe the valency platform molecule and means that the valency platform molecule elicits substantially no immune response when it is administered by itself or when administered as the platform portion of a conjugate to an individual.

As used herein "individual" denotes a member of the mammalian species and includes humans, primates, mice and domestic animals such as cattle and sheep, sports animals such as horses, and pets such as dogs and cats.

As used herein the term "immunogen" means a chemical entity that elicits a humoral immune response when injected into an animal. Immunogens have both B cell epitopes and T cell epitopes.

The term "analog" of an immunogen intends a molecule that (a) binds specifically to an antibody to which the immunogen binds specifically and (b) lacks T cell epitopes. Although the analog will normally be a fragment or derivative of the immunogen and thus be of the same chemical class as the immunogen (e.g., the immunogen is a polypeptide and the analog is a polypeptide), chemical similarity is not essential. Accordingly, the analog may be of a different chemical class than the immunogen (e.g., the immunogen is a carbohydrate and the analog is a polypeptide) as long as it has the functional characteristics (a) and (b) above. The analog may be a protein, carbohydrate, lipid, lipoprotein, glycoprotein, lipopolysaccharide, nucleic acid or other chemical or biochemical entity.

An analog of an immunogen may also comprise a "mimotope." The term "mimotope" intends a synthetic molecule which competitively inhibits the antibody from binding the immunogen. Because it specifically binds the antibody, the mimotope is considered to mimic the antigenic determinants of the immunogen. Like an analog of an immunogen, a mimotope (a) binds specifically to an antibody to which the immunogen binds specifically and (b) lacks T cell epitopes.

An analog of an immunogen may also comprise an "aptamer." The term "aptamer" intends a synthetic oligonucleotide which competitively inhibits the antibody from binding the immunogen. Like an analog of an immunogen, an aptamer (a) binds specifically to an antibody to which the immunogen binds specifically and (b) lacks T cell epitopes.

As used herein the term "B cell anergy" intends unresponsiveness of those B cells requiring T cell help to produce and secrete antibody and includes, without limitation, clonal deletion of immature and/or mature B cells and/or the inability of B cells to produce antibody and or apoptosis. "Unresponsiveness" means a therapeutically effective reduction in the humoral response to an immunogen. Quantitatively the reduction (as measured by reduction in antibody production) is at least 50%, preferably at least 75%, and most preferably 100%.

"Antibody" means those antibodies whose production is T cell dependent.

The valency of a chemically-defined valency platform molecule within the present invention can be predetermined by the number of branching groups added to the platform molecule. Suitable branching groups are typically derived from diamino acids, triamines, and amino diacids. A conjugate within the instant invention is biologically stabilized; that is, it exhibits an in vivo excretion half-life of hours to days to months to confer therapeutic efficacy. The chemically-defined valency platform molecules of the instant invention are also substantially nonimmunogenic (i.e., they exhibit no or only mild immunogenicity when administered to animals), non-toxic at the doses given (i.e., they are sufficiently non-toxic to be useful as therapeutic agents) and are preferably composed of a defined chemical structure. They provide a non-immunogenic, non-toxic polyfunctional substrate to which a multiplicity of biological or chemical molecules such as polynucleotide duplexes may be attached covalently. They will normally have an average molecular weight in the range of about 200 to about 200,000, usually about 200 to about 20,000, and are homogeneous as compared to the prior art polymers which were a mixture of compounds of widely fluctuating molecular weight. Examples of particularly preferred, homogenous valency platform molecules within the present invention are derivatized 2,2'-ethylenedioxydiethylamine (EDDA), triethylene glycol (TEG) and polyethylene glycols (PEGs) having a molecular weight of about 200 to about 8,000.

Conjugation of a biological or synthetic molecule to the chemically-defined platform molecule may be effected in any number of ways, typically involving one or more crosslinking agents and functional groups on the biological or synthetic molecule and valency platform molecule.

The synthetic polynucleotide duplexes that are coupled to the valency platform molecule are composed of at least about 20 bp and preferably 20–50 bp. Polynucleotides described herein are deoxyribonucleotides unless otherwise indicated and are set forth in 5' to 3' orientation. Preferably the duplexes are substantially homogeneous in length; that is, the variation in length in the population will not normally exceed about ±20%, preferably ±10%, of the average duplex length in base pairs. They are also preferably substantially homogeneous in nucleotide composition; that is, their base composition and sequence will not vary from duplex to duplex more than about 10%. Most preferably they are entirely homogeneous in nucleotide composition from duplex to duplex.

Based on circular dichroic (CD) spectra interpretation, the duplexes that are useful in the invention assume a B-DNA type helical structure. It should be understood that it is not intended that the invention be limited by this belief and that the duplexes may, upon more conclusive analysis assume Z-DNA and/or A-DNA type helical structures.

These polynucleotide duplexes may be synthesized from native DNA or synthesized by chemical or recombinant techniques. Naturally occurring or recombinantly produced dsDNA of longer length may be digested (e.g., enzymatically, chemically or by mechanical shearing) and fractionated (e.g., by agarose gel or Sephadex® column) to obtain polynucleotides of the desired length.

Alternatively, pairs of complementary single-stranded polynucleotide chains up to about 70 bases in length are readily prepared using commercially available DNA synthesizers and then annealed to form duplexes by conventional procedures. Synthetic dsDNA of longer length may be obtained by enzymatic extension (5'-phosphorylation followed by ligation) of the chemically produced shorter chains.

The polynucleotides may also be made by molecular cloning. For instance, polynucleotides of desired length and sequence are synthesized as above. These polynucleotides may be designed to have appropriate termini for ligation into specific restriction sites. Multiple iterations of these oligomers may be ligated in tandem to provide for multicopy replication. The resulting construct is inserted into a standard cloning vector and the vector is introduced into a suitable microorganism/cell by transformation. Transformants are identified by standard markers and are grown under conditions that favor DNA replication. The polynucleotides may be isolated from the other DNA of the cell/microorganism by treatment with restriction enzymes and conventional size fractionation (e.g., agarose gel, Sephadex® column).

Alternatively, the polynucleotides may be replicated by the polymerase chain reaction (PCR) technology. Saiki, R. K. et al., *Science* (1985) 230:1350; Sacki, et al., *Science* (1988) 239:487; Sambrook, et al., *In Molecular Cloning Techniques: A Laboratory Manual*, Vol. 12, p 14.1–14.35 Cold Spring Harbor Press (1989).

Polynucleotides may be screened for binding activity with SLE antisera by the assays described in the examples. The modified Farr assay in which binding activity may be expressed as $I_{50}$ (the polynucleotide concentration in molar nucleotides resulting in half-maximal inhibition) is a preferred assay. Polynucleotide duplexes having an $I_{50}$ of less than about 500 nM, preferably less than 50 nM, are deemed to have significant binding activity and are, therefore, useful for making the conjugates of this invention.

The polynucleotides are conjugated to the chemically-defined valency platform molecule in a manner that preserves their antibody binding activity. This is done by conjugating the polynucleotide to the valency platform molecule at a predetermined site on the polynucleotide chain such that the polynucleotide forms a pendant chain of at least about 20 base pairs measured from the conjugating site to the free (unattached) end of the chain.

In a particularly preferred embodiment, the polynucleotides of the invention conjugates are coupled to a linker molecule at or proximate one of their ends. The linker molecule is then coupled to the chemically-defined valency platform molecule. For example, a defined double-stranded PN can be conjugated to a valency platform molecule by first providing a single chain consisting of approximately 20 alternating cytosine (C) and adenosine (A) nucleotides. Four CA chains can then be covalently conjugated through linkers such as HAD to four reactive sites on a derivatized platform molecule such as triethylene glycol. The valency platform molecule is synthesized to include groups such as bromoacetyl. During the conjugation, a leaving group is displaced by sulfur. A second single nucleotide chain consisting of approximately 20 alternating thymidine (T) and guanosine (G) nucleotides can then be annealed to the CA strand to form a double-stranded PN conjugate of the formula, $[(PN)_{20}\text{-linker}]_4$-valency platform molecule.

Alternatively, in another preferred embodiment, the polynucleotide may be coupled to the derivatized valency platform molecule at the 3' end of the polynucleotide via a morpholino bridge formed by condensing an oxidized 3' terminal ribose on one of the strands of the polynucleotide with a free amino group on the derivatized platform molecule and then subjecting the adduct to reducing conditions to form the morpholino linkage. Such coupling requires the derivatized platform molecule to have at least an equal number of amino groups as the number of polynucleotide duplexes to be bound to the platform molecule. The synthesis of such a conjugate is carried out in two steps. The first step is coupling one strand of the polynucleotide duplex to the derivatized platform molecule via the condensation/reduction reaction described above. The oxidized 3' terminal ribose is formed on the single polynucleotide strand by treating the strand with periodate to convert the 3' terminal ribose group to an oxidized ribose group. The single-stranded polynucleotide is then added slowly to an aqueous solution of the derivatized platform molecule with a pH of about 6.0 to 8.0 at 2°–8° C. The molar ratio of polynucleotide to platform molecule in all the conjugation strategies will normally be in the range of about 2:1 to about 30:1, usually about 2:1 to about 8:1 and preferably about 4:1 to 6:1. In this regard, it is preferable that the conjugate not have an excessively large molecular weight as large molecules, particularly those with repeating units, of m.w. >200,000 may be T-independent immunogens. See Dintzis et al., *J. Immun.* (1983) 131:2196 and *J. Immun.* (1989) 143:1239. During or after the condensation reaction (normally a reaction time of 24 to 48 hr), a strong reducing agent, such as sodium cyanoborohydride, is added to form the morpholino group. The complementary strand of the duplex is then added to the conjugate and the mixture is heated and slowly cooled to cause the strands to anneal. The conjugate may be purified by gel permeation chromatography.

An alternative to the ribose strategy is forming aldehyde functionalities on the polynucleotides and using those functionalities to couple the polynucleotide to the platform molecule via reactive functional groups thereon. Advantage may be taken of the fact that gem, vicinal diols, attached to the 3' or 5' end of the polynucleotide, may be oxidized with sodium periodate to yield aldehydes which can condense with functional amino groups of the platform molecule. When the diols are in a ring system, e.g., a five-membered ring, the resulting condensation product is a heterocyclic ring containing nitrogen, e.g., a six-membered morpholino or piperidino ring. The imino-condensation product is stabilized by reduction with a suitable reducing agent; e.g., sodium borohydride or sodium cyanoborohydride. When the diol is acyclic, the resulting oxidation product contains just one aldehyde and the condensation product is a secondary amine.

Another procedure involves introducing alkylamino or alkylsulfhydryl moieties into either the 3' or 5' ends of the polynucleotide by appropriate nucleotide chemistry, e.g., phosphoramidite chemistry. The nucleophilic groups may then be used to react with a large excess of homobifunctional cross-linking reagent, e.g., dimethyl suberimidate, in the case of alkylamine derivatives, or an excess of heterobifunctional cross-linking reagent, e.g., m-maleimidobenzoyl-N-hydroxysuccinimide ester (MBS) or succinimidyl (4-iodoacetyl) aminobenzoate (SIAB), for the alkylsulfhydryl derivatives. Once excess cross-linker is removed, the polynucleotide derivatives are reacted with amino groups on the platform molecule. Alternatively, the sulfhydryl group may be reacted with an electrophilic center on the platform, such as a maleimide or α-haloacetyl group or other appropriate Michael acceptor.

Still another strategy employs modified nucleosides. Suitable deoxynucleoside derivatives can be incorporated, by standard DNA synthetic chemistry, at desired positions in the polynucleotide, preferably on the 5' or 3' ends. These nucleoside derivatives may then react specifically and directly with alkylamino groups on the platform molecule. Alternatively, side reactions seen with the above-described dialdehyde chemistry, such as amine catalyzed beta-elimination, can be circumvented by employing appropriate nucleoside derivatives as the 3' terminus of the chain to be attached. An example of this is 5' methylene extension of ribose; i.e., a 5' (2-hydroxyethyl)- group instead of a 5' hydroxymethyl group. An alternative would be to use a phosphonate or phosphinate linkage for the 3' terminal dinucleotide of the polynucleotide to be attached to the platform molecule.

Analogs of Immunogens

Immunogens that are involved in antibody- mediated pathologies may be external (foreign to the individual) immunogens such as allergens, sperm associated with male infertility, the rheumatic fever carbohydrate complex, the RBC Rh/D antigen associated with hemolytic disease of the newborn, biological drugs, including native biological substances foreign to the individual such as therapeutic proteins, peptides and antibodies, and the like or self-immunogens (autoimmunogens) such as those associated with thyroiditis (thyroglobulin), stroke (cardiolipin) and myasthenia gravis (acetylcholine receptor).

Analogs to such immunogens may be identified by screening candidate molecules to determine whether they (a) bind specifically to serum antibodies to the immunogen and (b) lack T cell epitopes. Specific binding to serum antibodies may be determined using conventional immunoassays and the presence or absence of T cell epitopes may be determined by conventional T cell activation assays. In this regard, an analog which "binds specifically" to serum antibodies to the immunogen exhibits a reasonable affinity thereto. Further in this regard, it should be recognized that testing for T cell epitopes is conducted on a subject-bysubject basis using T cells taken from an intended recipient or from various patients that represent the target population of recipients. The presence or absence of T cell epitopes may be determined using the tritiated thymidine incorporation assay described in the examples. The presence of T cell epitopes can also be determined by measuring secretion of T cell-derived lymphokines by methods well known in the art. Analogs that fail to induce statistically significant incorporation of thymidine above background are deemed to lack T cell epitopes. It will be appreciated that the quantitative amount of thymidine incorporation may vary with the immunogen. Typically a stimulation index below about 2—3, more usually about 1–2, is indicative of a lack of T cell epitopes.

A normal first step in identifying useful analogs is to prepare a panel or library of candidates to screen. For instance, in the case of protein or peptide analogs, libraries may be made by synthetic or recombinant techniques such as those described by Geysen et al. in *Synthetic Peptides as Antigens;* Ciba Symposium (1986) 119:131–149; Devlin et al., *Science* (1990) 249:404–406; Scott et al., *Science* (1990) 249:386–390; and Cwirla et al., *PNAS USA* (1990) 87:6378–6382. In one synthetic technique, peptides of about 5 to 30 amino acids are synthesized in such a manner that each peptide overlaps the next and all linear epitopes are represented. This is accomplished by overlapping both the carboxyl and amino termini by one less residue than that expected for a B cell epitope. For example, if the assumed minimum requirement for a B cell epitope is six amino acids, then each peptide must overlap the neighboring peptides by five amino acids. In this embodiment, each peptide is then screened against antisera produced against the native immunogen, either by immunization of animals or from patients, to identify the presence of B cell epitopes. Those molecules with antibody binding activity are then screened for the presence of T cell epitopes as described in the examples. The molecules lacking T cell epitopes are useful as analogs in the invention.

If the T cell epitope(s) of an immunogen are known or can be identified, random T cell screening of candidate analogs is not necessary. In such instances, the T cell epitope(s) may be altered (e.g., by chemical derivatization, or elimination of one or more components of the epitope) to render them inoperative or be eliminated completely, such as, for instance, in the case of peptides, by synthetic or recombinant procedures.

Mimotopes and aptamers are synthesized by conventional methods and are screened in the same manner as other analogs of immunogens.

The analogs are coupled to a nonimmunogenic valency platform molecule to prepare the conjugates of the invention. Conjugates comprising valency platform molecules and biologically active molecules such as carbohydrates, lipids, lipopolysaccharides, proteins, glycoproteins, drugs, and analogs of interest are synthesized utilizing the chemistries exemplified herein. A preferred method of synthesis is to incorporate a linker molecule on the biological molecule by well known methods chosen on a case-by-case basis.

When conjugating drugs such as adriamycin (doxorubicin) to a valency platform molecule, the amino group on a sugar ring can react with platform molecules containing active esters. Adriamycin can also be modified to contain thiol groups for conjugation to a haloacetylated platform (Kaneko, T., et al., *Bioconjugate Chemistry,* 2:133 (1991)).

Carbohydrates such as oligosaccharides can be modified to contain a sulfhydryl-containing linker (Wood, S. J. and Wetzel, R., *Bioconjugate Chemistry,* 3:391 (1992)). The sulfhydryl group is used for conjugation to a haloacetylated platform. Alternatively, carbohydrates can be oxidized to generate aldehydes which are reacted with amino platforms in the presence of $NaBCHBH_3$ to form conjugates.

Lipids such as glycolipids containing an ethanolamine group are reacted with an activated carboxylate on the platform. Lipopolysaccharides containing sugar units are oxidized to generate aldehydes which are reacted in the presence of $NaCNBH_3$ with amino platforms to form conjugates by reductive amination.

In the case of additional proteins such as Fab' antibody fragments, sulfhydryl groups on the protein (Fab') are conjugated to a platform via haloacetyl groups. Glycoproteins are modified with a thiol linker using iminothiolate. The thiol reacts with platforms containing haloacetyl groups.

The ability of the conjugates to act as tolerogens and specifically suppress production of antibodies may be evaluated in the murine model described in the examples.

The conjugates will normally be formulated for administration by injection, (e.g., intraperitoneally, intramuscularly, intravenously etc.). Accordingly, they will typically be combined with pharmaceutically acceptable aqueous carriers such as saline, Ringer's solution, dextrose solution, and the like. The conjugate will normally constitute about 0.01% to 10% by weight of the formulation. The conjugate is administered to an individual in amounts sufficient to at least partially reestablish tolerance to the autoantigens causing SLE. Such amounts are sometimes herein referred to as "therapeutically effective" amounts. The particular dosage regimen i.e., dose, timing and repetition, will depend upon the particular individual, and that individual's medical history. Normally a dose of about 1 to 1000 μg conjugate/kg body weight will be given. Repetitive administrations may be required to achieve and/or maintain a state of immune tolerance.

The following examples further illustrate the invention and its unexpectedness relative to the prior art. These examples are not intended to limit the invention in any manner.

EXAMPLE 1

The following reaction schemes illustrate methods of synthesizing derivatized chemically-defined valency platform molecules within the present invention. In this example, DMTr=4,4'-dimethoxytriphenylmethyl; Tr=trityl; Bz=benzoyl; Cp=deoxycytidine monophosphate, CE=cyanoethyl; CPG=controlled pore glass, DMF=dimethylformamide, DCC=dicyclohexylcarbodiimide, TFA=trifluoroacetic acid, CDI=carbonyl diimidazole, Ts=tosyl (para-toluene sulfonyl), DIPAT=diisopropyl ammonium tetraazolide, TBDMSCl=tertbutyl dimethyl silyl chloride, TBAF=tetrabutyl ammonium fluoride, NMMO=N-methylmorpholine-N-oxide.

Reaction Scheme 1
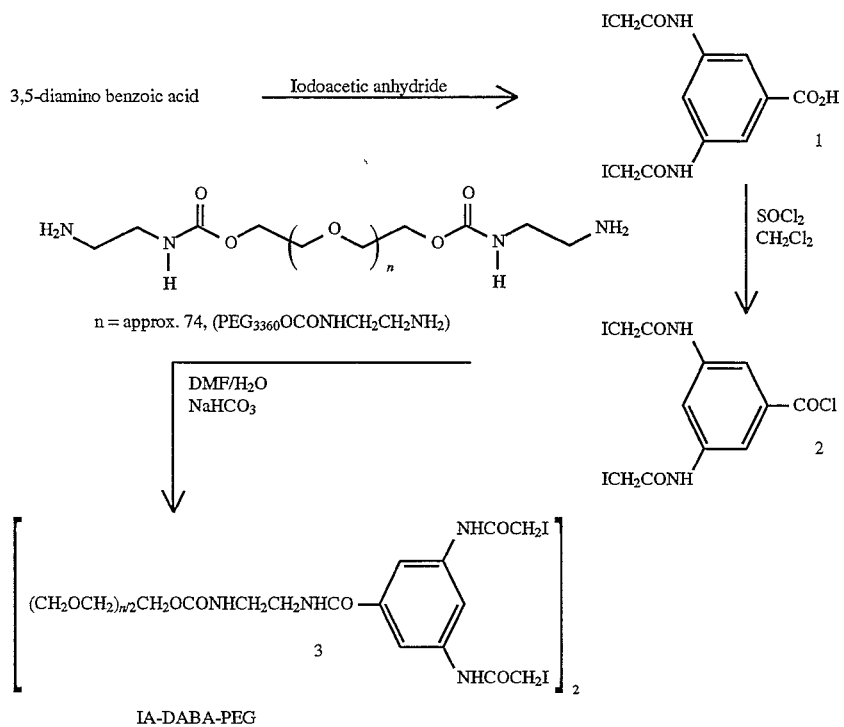
Reaction Scheme 2
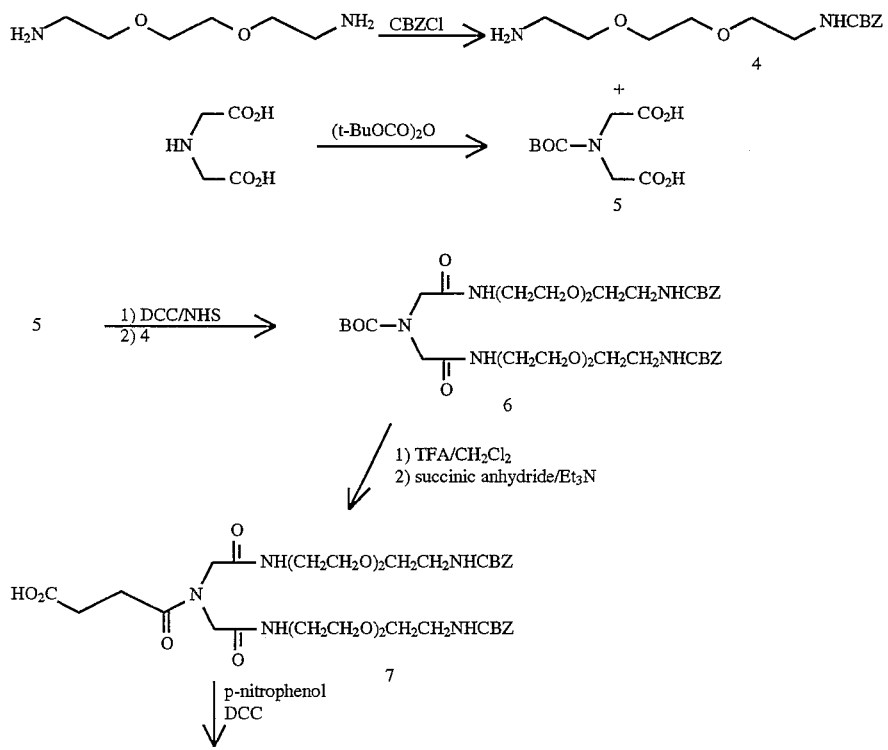

-continued
Reaction Scheme 2
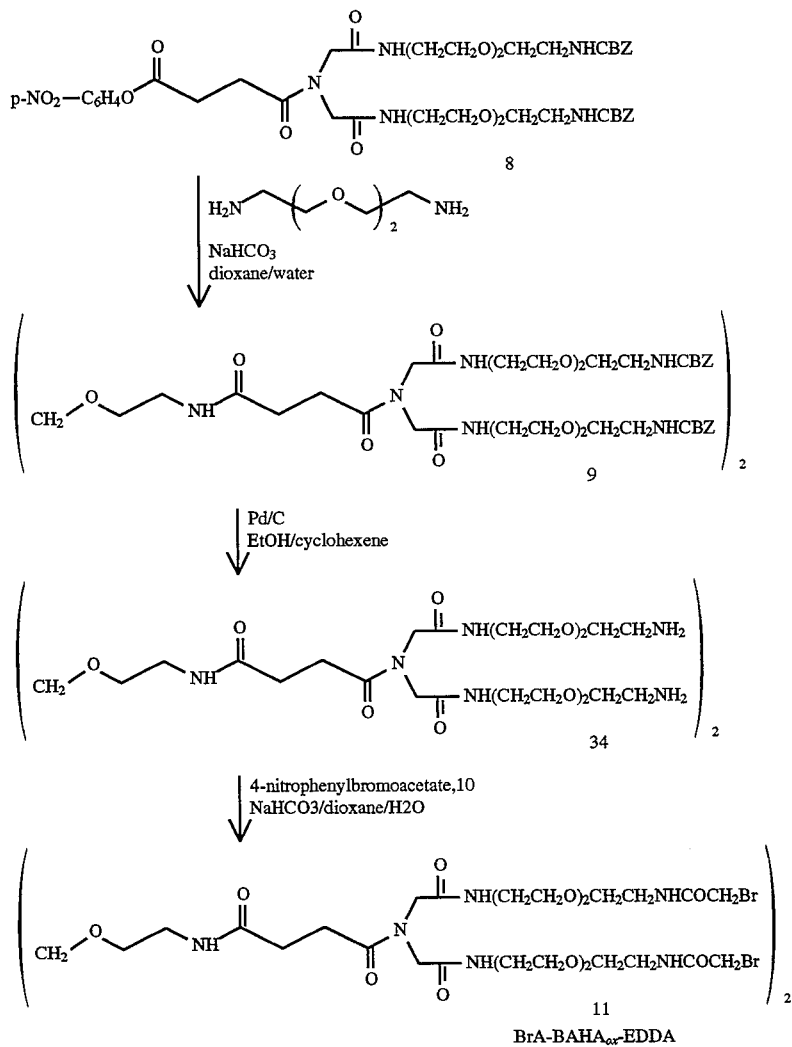
Reaction Scheme 3
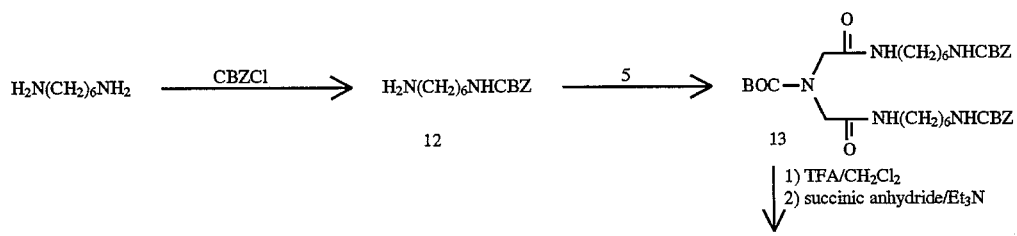

-continued
Reaction Scheme 3
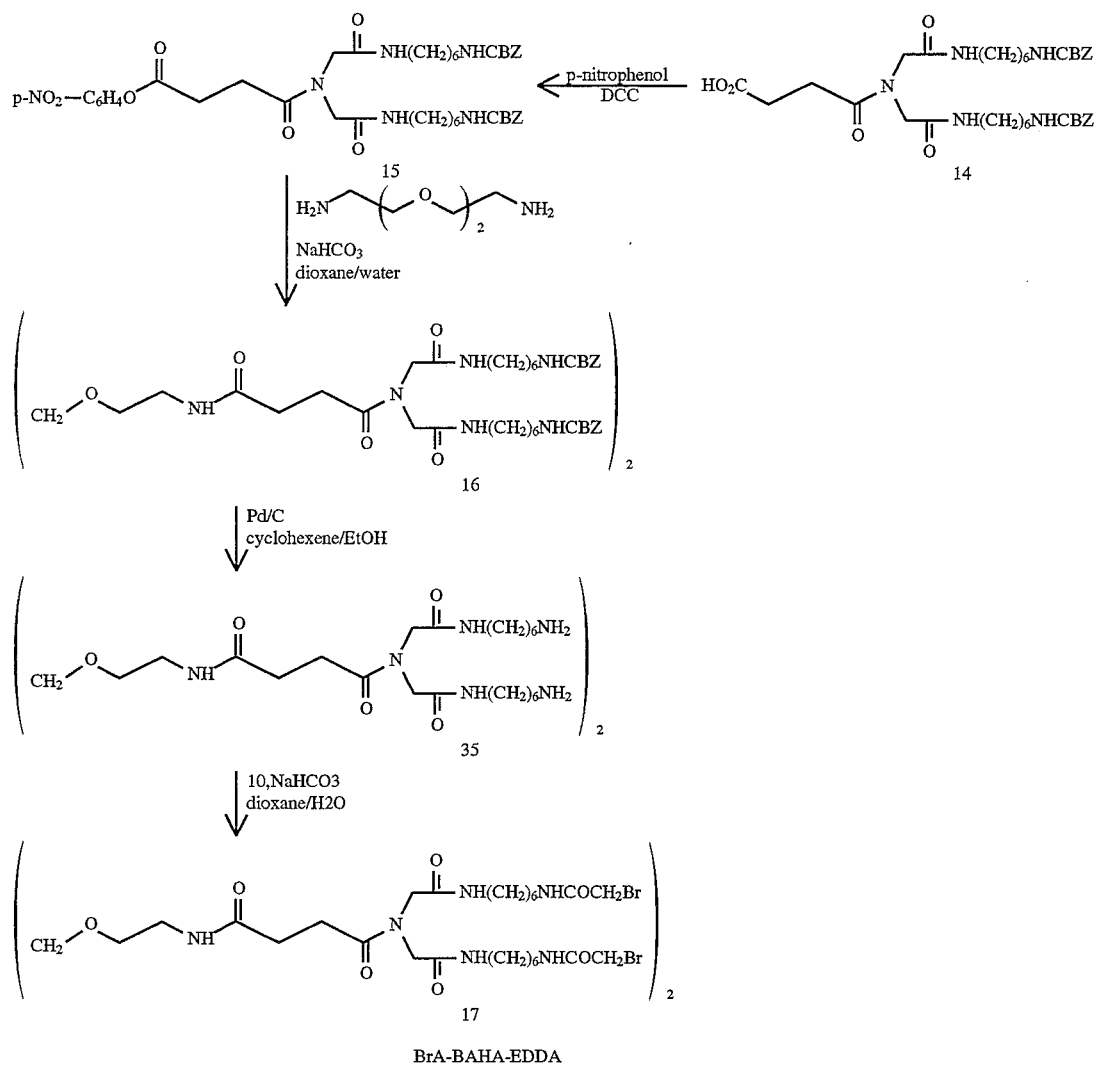
BrA-BAHA-EDDA
Reaction Scheme 4
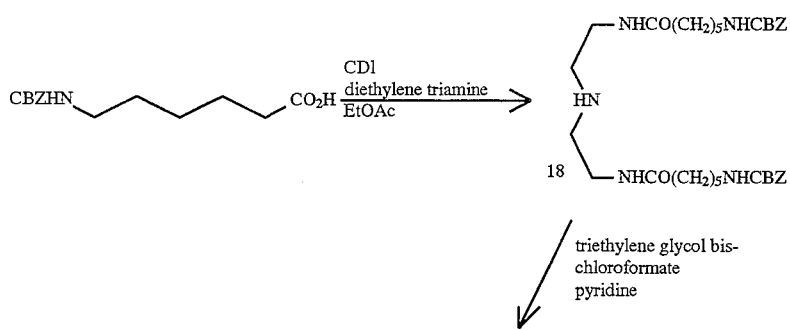

-continued
Reaction Scheme 4
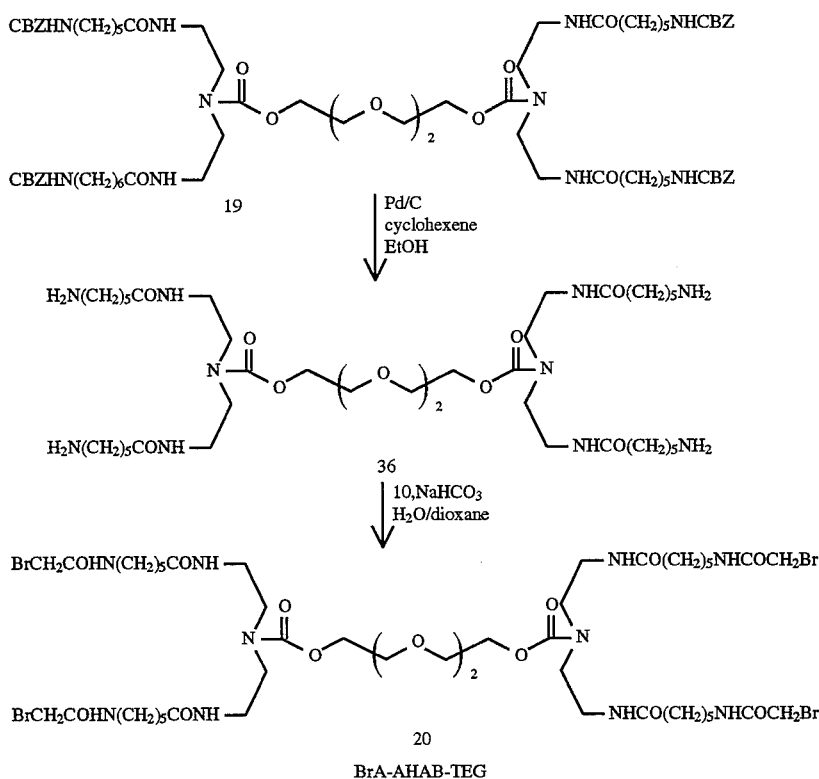
Reaction Scheme 5
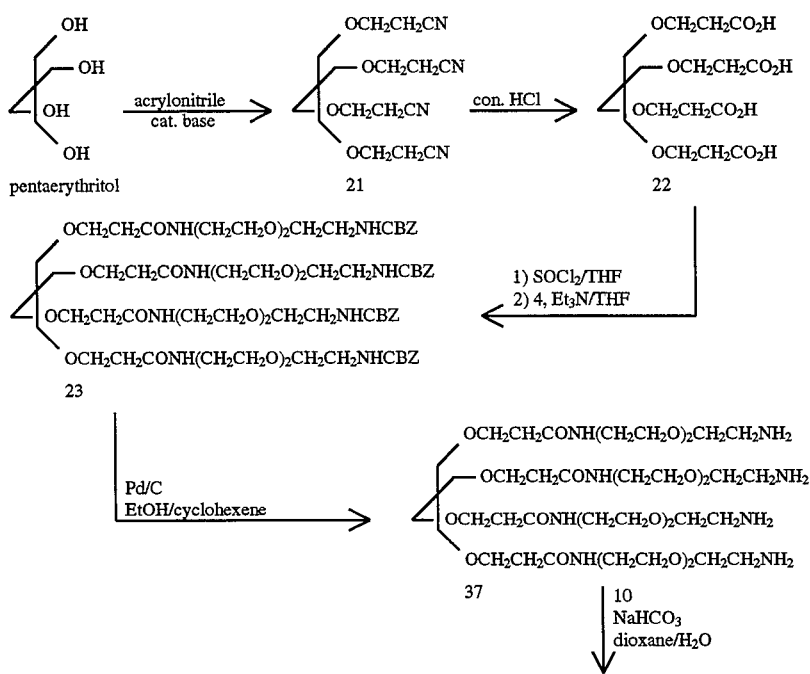

-continued
Reaction Scheme 5
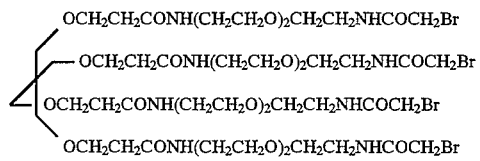
Reaction Scheme 6
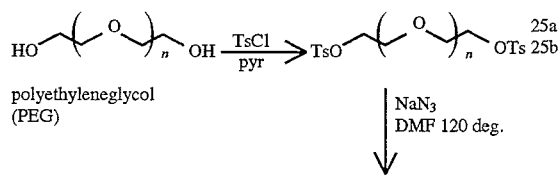
polyethyleneglycol
(PEG)
-continued
Reaction Scheme 6
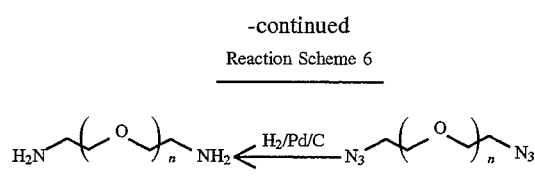
n = approx. 74 (PEG average MW = approx. 3350)
n = approx. 200 (PEG average MW = approx. 8000)
Reaction Scheme 7
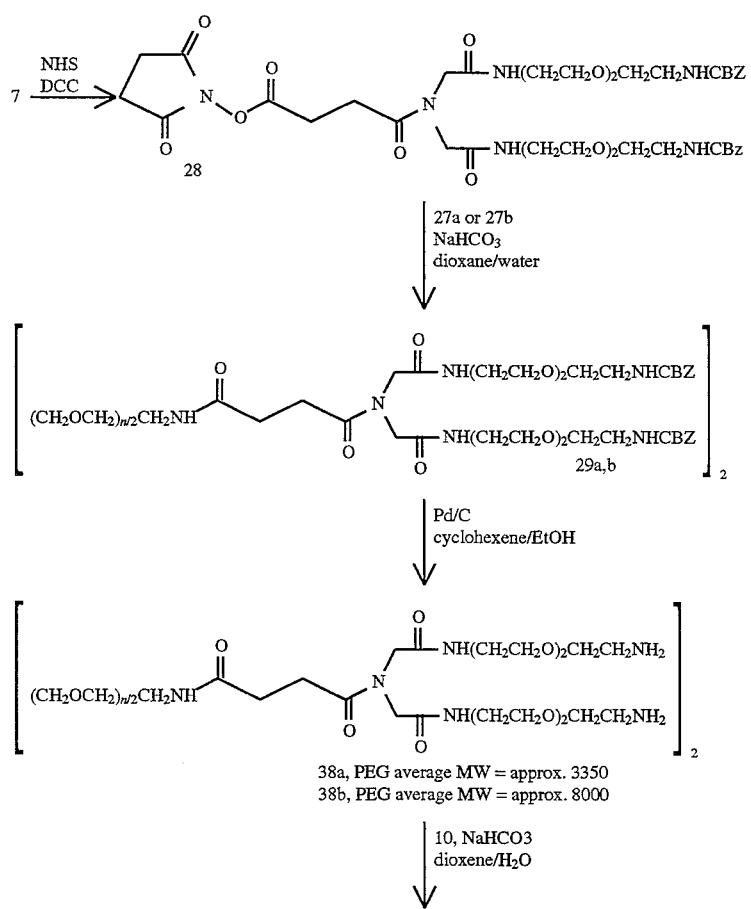
38a, PEG average MW = approx. 3350
38b, PEG average MW = approx. 8000

Reaction Scheme 7 -continued
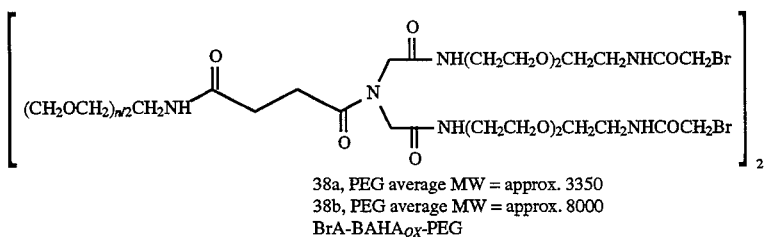
38a, PEG average MW = approx. 3350
38b, PEG average MW = approx. 8000
BrA-BAHA$_{OX}$-PEG
Reaction Scheme 8
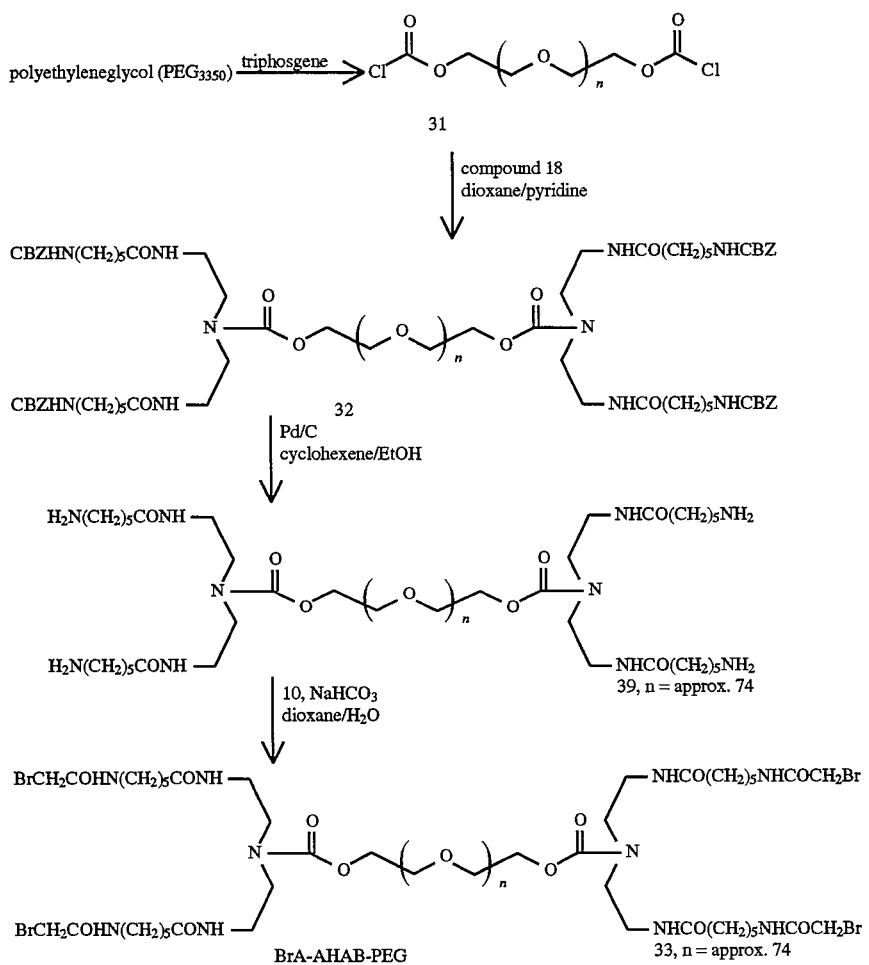

Reaction Scheme 9
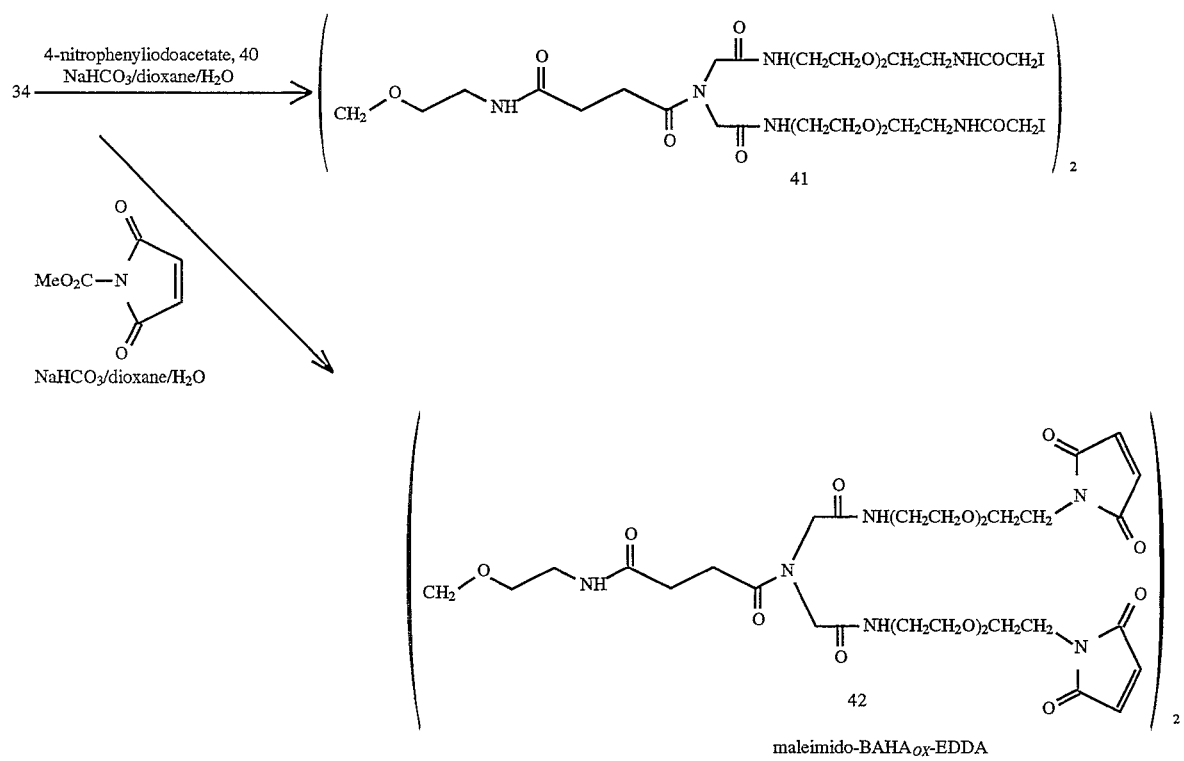
Reaction Scheme 10
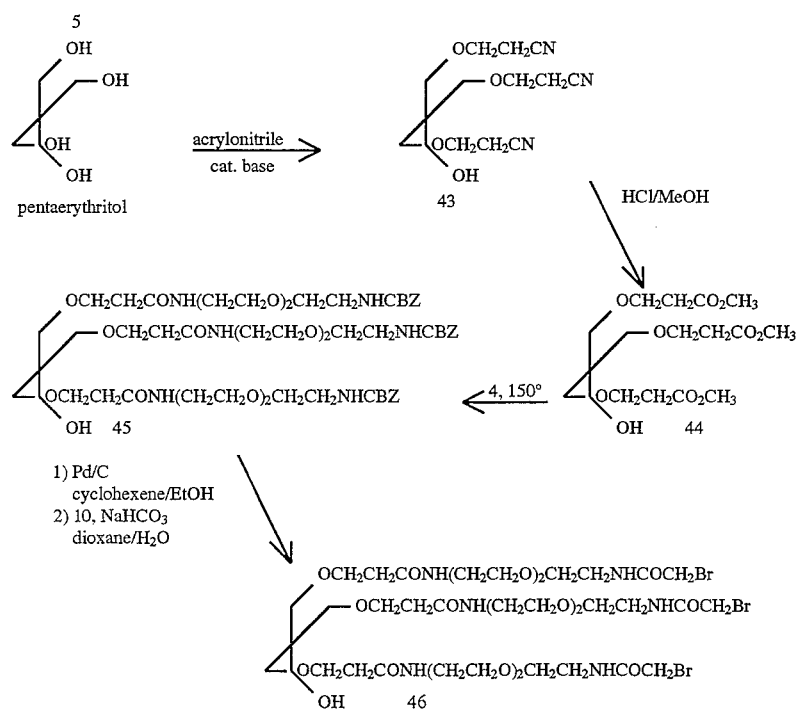

Synthesis of reagents used to modify $(CA)_8$, $(CA)_{10}$, $(CA)_{12}$ and $(CA)_{16}$ with disulfide linkers is described in Reaction Scheme 11 below:
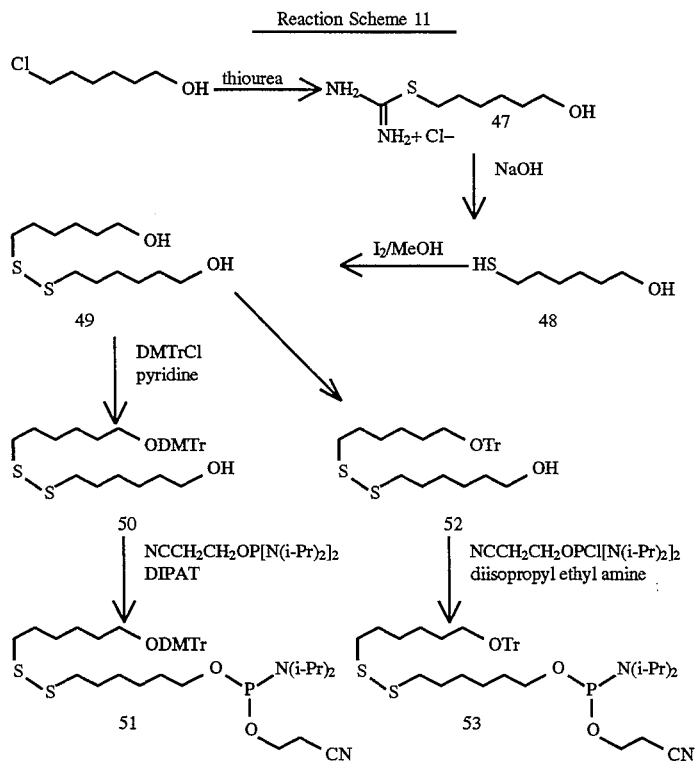
Synthesis of a reagent used to modify $(CA)_{25}$ with vicinal diol linkers is described in Reaction Scheme 12 below:
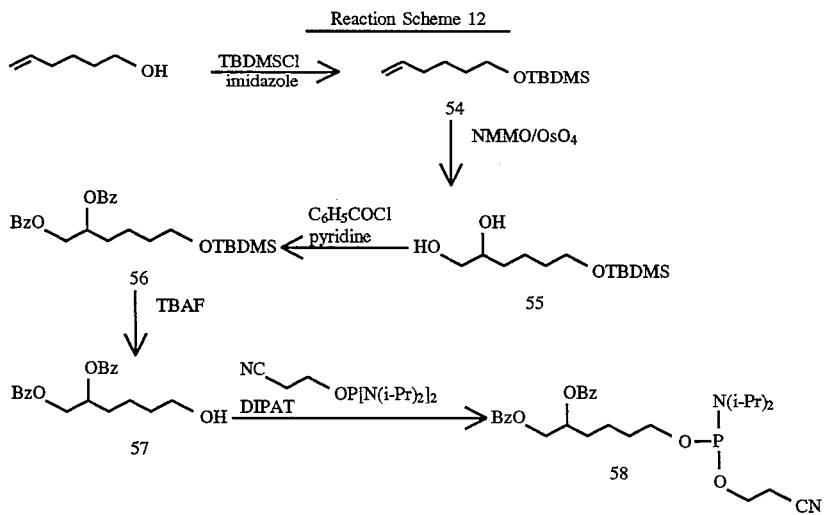

Reaction Scheme 13

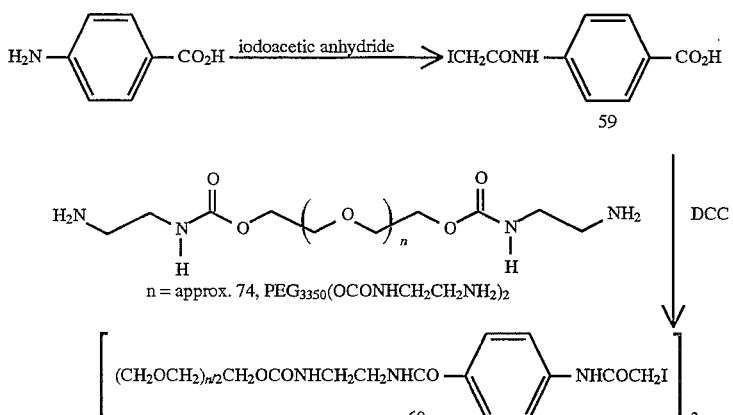

EXAMPLE 2

Synthesis of Chemically-Defined Valency Platform Molecules

Compound 1—[3,5-Bis-(iodoacetamido)benzoic acid]:

2.93 g (8.28 mmol, 2.2 eq) of iodoacetic anhydride was added to a stirred suspension of 572 mg (3.76 mmol) of 3,5-diaminobenzoic acid in 19 mL of dioxane at room temperature under $N_2$ atmosphere. The mixture was stirred, covered with foil for 20 hours and partitioned between 50 mL of EtOAc and 50 mL of 1N HCl solution. The EtOAc layer was washed with brine, dried over $MgSO_4$, filtered, and concentrated on a rotary evaporator to give 3.3 g of tan solid. The material was purified by silica gel chromatography (94/5/1 $CH_2Cl_2$/MeOH/HOAc) to yield 992 mg (54%) of compound 1 as a white solid: NMR (DMSO) 3.84 (s, 4H), 7.91 (s, 2H), 8.14 (s, 1H), 10.56 (s, 2H).

Compound 2—[3,5-Bis-(iodoacetamido)benzoyl chloride]:

117 μL (1.6 mmol, 190 mg) of $SOCl_2$ was added to a solution of 390 mg (0.8 mmol) of 1 in 34 mL of THF. The mixture was refluxed under $N_2$ atmosphere until all solids had dissolved (approximately 30 minutes) to give a clear red-brown solution. The mixture was concentrated on the rotary evaporator and placed under vacuum to provide crude compound 2 as a foamy solid which was used directly in the next step.

Compound 3—[N,N'-Bis-(3,5-bis-(iodoacetamido]benzoyl) derivative of α,ω-bis-(N-2-aminoethylcarbamoyl) polyethyleneglycol]:

570 mg of α,ω-bis-(N-2-aminoethylcarbamoyl) polyethyleneglycol (0.16 mmol, 3350 g/mol, Sigma) was placed in a tared flask. Toluene (20 mL) was added and water was removed by azeotropic distillation. The residue was dried under vacuum to give 549 mg of solid and dissolved in 4 mL THF with 89 μL (0.64 mmol) of diisopropylethylamine. The crude acid chloride was dissolved in 4 mL anhydrous THF and added to the mixture over 30 seconds under $N_2$. The mixture was stirred for 16 hours at room temperature and partitioned between 25 mL of 0.1N HCl and 25 mL of $CH_2Cl_2$. The aqueous layer was again extracted with $CH_2Cl_2$ and the organic layers were combined, washed with 25 mL of $H_2O$, followed by 50 mL of at $NaHCO_3$ solution. The organic layers were dried with $Na_2SO_4$, filtered, and concentrated to give 784 mg of orange oil. Silica gel chromatography (9/1 $CH_2Cl_2$/MeOH) yielded 190 mg of colorless oil which was crystallized from hot EtOH/$Et_2O$, collected on sintered glass filter under $N_2$ pressure, and dried under vacuum to provide 177 mg of compound 3 as a white solid: NMR ($CDCl_3$) 3.40 (bd m, 8H), 3.59 (bd s, $(CH_2CH_2O)_n$, integral too large to integrate in relation to other integrals), 3.91 (s, 8H), 4.21 (m, 4H), 6.04 (bd m, 2H), 7.55 (bd m, 2H), 7.78 (bd s, 4H), 8.10 (bd s, 2H), 9.30 (bd m, 4H): iodoacetyl determination (European Journal of Biochemistry (1984) 140:63–71): Calculated, 0.92 mmol/g; Found, 0.96 mmol/g.

Compound 4—[Mono-N-carbobenzyloxy-3,6-dioxa-1,8-diaminooctane]:

A solution of 14.3 mL (17.1 g, 100 mmol) of benzylchloroformate in 200 mL of $CH_2Cl_2$ was added dropwise over a 1 hour period to a solution of 29.0 mL (29.6 g, 200 mmol) of 1,2-bis-(2'-aminoethyoxy)ethone (Fluka) in 100 mL of $CH_2Cl_2$ at 0°. The mixture was stirred at room temperature for 24 hours and 1N HCl was added until the aqueous layer remained acidic (pH less than 2). The aqueous layer was washed with three 50 mL portions of $CH_2Cl_2$ and neutralized with 1N NaOH until the pH was above 13. The basic aqueous layer was extracted with five 75 mL portions of $CH_2Cl_2$. The combined $CH_2Cl_2$ layers were dried ($MgSO_4$), filtered, and concentrated to yield 12.7 g (45%) of compound 4 as a thick oil: $^1$H NMR ($CDCl_3$) d 2.82 (bd s, 2H), 3.30–3.60 (m, 12H), 5.10 (s, 2H), 5.75 (bd s, 1H), 7.20–7.40 (m, 5H); $^{13}$C NMR ($CDCl_3$) d 41.1, 41.8, 66.5, 70.0, 70.2, 70.4, 73.5, 127.9, 128.0, 128.4, 136.9, 156.4.

Compound 5—[N-tert-butyloxycarbonyliminodiacetic acid]:

This compound was prepared by a procedure similar to that reported by Garrigues, B. and Lazraq, E. M. Tetrahedron Letters (1986) 27, 1685–1686. 47 mL (34.2 g, 338 mmol) of $Et_3N$ was added to a stirred solution of 22.0 g (169 mmol) of iminodiacetic acid and 36.8 g (169 mmol) of di-tert butyldicarbonate in 169 mL of 50/50 dioxane/$H_2O$ at room temperature. The mixture was stirred for 24 hours and most of the dioxane was removed on a rotary evaporator. The mixture was partitioned between 350 mL of 1N HCl and five 100 mL portions of EtOAc. The combined EtOAc layers were dried ($MgSO_4$), filtered, and concentrated to give a white solid. Recrystallization from hexanes/EtOAc yielded 35.3 g (90%) of compound 5 as crystals: m.p. 131°–132° fused; $^1$H NMR (DMSO) d 1.35 (s, 9H), 3.87 (s, 2H), 3.91 (s, 2H), 12.6 (bd s, 2H); $^{13}$C NMR (DMSO) d 27.9, 49.6, 79.6, 154.8, 171.2.

Compound 6.

9.99 g (48.5 mmol) of dicyclohexylcarbodiimide was added to a solution of 4.52 g 73 (19.4 mmol) of compound 5 and 4.46 g (38.8 mmol) of N-hydroxysuccinimide in 100 mL of THF at 0°. The mixture was stirred for 3 hours at 0° C., and a solution of 5.39 mL (3.92 g, 38.8 mmol) Et$_3$N and 10.9 g (38.7 mmol) of compound 4 in 83 mL of THF was added, and the mixture was stirred at 5° C. for 17 hours. The mixture was filtered to remove solids, and the filtrate was concentrated to an oil which was partitioned between 400 mL of EtOAc and two 100 mL portions of 1N HCl. The EtOAc layer was washed with three, 100 mL portions of 1N Na$_2$CO$_3$, 100 mL of brine, dried (MgSO$_4$), filtered and concentrated to provide 14.2 g (96%) of compound 6 as a thick oil; $^1$H NMR (CDCl$_3$) d 1.41 (s, 9H), 3.30–3.70 (m, 24H), 3.70–3.90 (m, 4H), 5.10 (s, 4H), 5.50 (bd s, 2H), 7.12 (bd s, 1H), 7.30–7.40 (m, 10H), 8.24 (bd s, 1H).

Compound 7.

26.3 mL (38.9 g, 156 mmol) of trifluoroacetic acid was added to a solution of 14.2 g (18.6 mmol) of compound 6 in 111 mL of CH$_2$Cl$_2$ and the mixture was stirred at room temperature for 3 hours. The mixture was concentrated on the rotary evaporator to give a viscous oil, and the oil was dissolved in 93 mL of THF. The solution was cooled to 0° C and 3.72 g (37.2 mmol) of succinic anhydride was added followed by 5.18 mL (3.76 g, 37.2 mmol) of Et$_3$N. The cooling bath was removed, and the mixture was stirred for 18 hours at room temperature. The solvent was removed under reduced pressure, and the resulting oil was partitioned between 300 mL of CH$_2$Cl$_2$ and three 100 mL portions of H$_2$O. The CH$_2$Cl$_2$ layer was dried (MgSO$_4$), filtered, and concentrated to provide an oil which was purified by chromatography on silica gel (9/1/0.1 EtOAc/MeOH/acetic acid) to provide 10.5 g (74%) of compound 7 as a viscous oil; $^1$H NMR (CDCl$_3$) d 2.50–2.60 (m, 4H), 3.30–3.60 (m, 24H), 3.88 (s, 2H), 4.03 (s, 2H), 5.07 (s, 4H), 5.77 (bd s, 2H), 7.20–7.30 (m 10H), 7.91 (bd s, 1H), 8.88 (bd s, 1H); $^{13}$C(CDCl$_3$) d 27.7, 29.0, 39.4, 41.0, 52.9, 53.8, 66.5, 69.3, 69.8, 70.0, 70.1, 127.8, 128.1, 128.3, 136.7, 156.6, 169.1, 169.6, 173.3, 174.5.

Compound 8—[4-Nitrophenyl ester of compound 7]:

1.61 g (7.83 mmol) of dicyclohexylcarbodiimide was added to a solution of 3.98 g (5.22 mmol) of 1 and 800 mg (5.75 mmol) of 4-nitrophenol in 26 mL of CH$_2$Cl$_2$ at 0°. The mixture was stirred at room temperature under N$_2$ for 64 hours. The mixture was cooled to 0°, 1 mL of HOAc was added, and the mixture was kept at 0° for 2 hours. The solids were removed by filtration, and the filtrate was concentrated. The residue was purified by silica gel chromatography (gradient, 91/8/1 to 84/15/1 CH$_2$Cl$_2$/IPA/HOAc) to provide 2.58 g (56%) of compound 8 as a viscous oil: $^1$H NMR (CDCl$_3$) d 2.66 (t, 2H), 2.84 (t, 2H), 3.32–3.68 (m, 24H), 3.90 (bd s, 2H), 4.01 (bd s, 2H), 5.06 (s, 4H), 5.58 (bd m, 2H), 6.91 (bd m, 1H), 7.27 (d, 2H), 7.33 (s, 10H), 8.23 (d, 2H), 9.01 (bd m, 1H).

Compound 10—[4-Nitrophenylbromoacetate]:

9.28 g (45 mmol) of dicyclohexylcarbodiimide was added to a stirred solution of 5.0 g (35.9 mmol) of bromoacetic acid and 8.50 g (61.1 mmol) of 4-nitrophenol in 180 mL of EtOAc at 0°. The mixture was stirred for 16 hours at 5° and 1 mL of acetic acid was added. The mixture was stirred for 20 minutes at room temperature and then placed in a freezer for 20 minutes. The solid material was removed by filtration, and the filtrate was concentrated to a viscous oil and crystallized from Et$_2$O/hexanes to provide 7.73 g (83%) of compound 10 as flakes: m.p. 86°–87°; TLC Rf=0.63 (50/50/1 hexanes/EtOAc/HOAc); $^1$H NMR (CDCl$_3$) d 4.13 (s, 2H), 7.36 (d, J=12 Hz, 2H), 8.32 (d, J=12 Hz, 2H); $^{13}$C NMR (CDCl$_3$) d 24.9, 122.1, 125.3, 155.5 164.9; Anal. calc'd for C$_8$H$_6$BrNO$_4$: C, 36.95; H, 2.33; N, 5.39. Found: C, 37.24; H, 2.33; N, 5.42.

Compound 9:

300 mg (3.57 mmol) of NaHCO$_3$, followed by 162 mg (1.09 mmol) of 2,2$_1$-(ethylenedioxy)-diethylamine (Fluka), was added to a solution of 2.37 g (2.68 mmol) of compound 8 in 15 mL of dioxane and 8 mL of H$_2$O. The mixture was stirred for 24 hours at room temperature and concentrated under vacuum to approximately one half the original volume. The concentrate was partitioned between 40 mL of CH$_2$Cl$_2$ and 40 mL of saturated NaHCO$_3$ solution. The CH$_2$Cl$_2$ layer was then washed twice with 40 mL of 0.5N HCl. The CH$_2$Cl$_2$ layer was washed with saturated NaCl solution, dried (MgSO$_4$), filtered, and concentrated to give 2.8 g of an oil. This crude produce was purified by silica gel chromatography (3/6/1 CH$_2$Cl$_2$/THF/MeOH) to provide 940 mg (59%) of compound 9 as an oil: TLC R$_f$=0.21 (3/6/1 CH$_2$Cl$_2$/THF/MeOH); $^1$H NMR (CDCl$_3$) d 2.45 (m, 4H), 2.59 (m, 4H), 3.25–3.55 (m, 60H), 3.87 (s, 4H), 4.05 (s, 4H), 5.07 (s, 8H), 5.62 (bd s, 4H), 6.78 (bd s, 2H), 7.34 (bd s, 20H), 8.56 (bd s, 2H); $^{13}$C NMR (CDCl$_2$) d 28.1, 30.3, 31.1, 39.4, 41.1, 52.9, 53.9, 66.5, 69.4, 69.7, 69.9, 70.2, 125.3, 127.8, 128.3, 136.8, 156.5, 168.8, 169.4, 172.1, 173.5.

Compound 94:

110mg of 10% Pd on carbon was added to a solution of 281 mg (0.175 mmol) of compound 9 in 5 mL of EtOH and 2 mL of cyclohexene under nitrogen and the resulting mixture was refluxed under nitrogen for 2 hours. When cool, the mixture was filtered through diatomaceous earth and concentrated under vacuum to give 170 mg (92%) of compound 34 as an oil which was used directly in the next step without purification; $^1$H NMR (CDCl$_3$) d 2.45 (m, 4H), 2.53 (m, 4H), 2.62 (m, 4H), 2.86 (m, 8H), 3.42–3.60 (m, 52H), 4.00 (s, 4H), 4.14 (s, 4H); $^{13}$C NMR (CDCl$_3$) d 28.2, 30.3, 31.1, 39.4, 41.1, 46.5, 48.6, 52.9, 53.8, 69.4, 69.7, 70.2, 72.4, 168.9, 169.5, 172.3, 173.8.

Compound 11:

128 mg (1.4 mmol) of NaHCO$_3$ and 200 mg (0.85 mmol) of compound 10 were added to a solution of 165 mg (0.155 mmol) of compound 34 in 6 mL of dioxane and 3 mL of H$_2$O. The resulting mixture was stirred for 24 hours at room temperature and concentrated under vacuum. The concentrate was purified by chromatography on Sephadex® G-10 (MeOH) to give 114 mg (46%) of compound 11 as a viscous oil. An analytical sample was prepared by preparative HPLC (C$_{18}$; gradient 15/85/0.1 to 30/70/0.1 CH$_3$CN/H$_2$O/CF$_3$CO$_2$H, 50 min, 225 nm): $^1$H NMR (CDCl$_3$) d 2.58 (m, 4H), 2.65 (m, 4H), 3.43–3.62 (m, 60H), 3.92, (s, 8H), 4.03 (s, 4H), 4.16 (s, 4H); MS (FAB) m/e (relative intensity) MNa+ 1605 (100), MH+ 1579 (1), 1581 (5), 1583 (7), 1585 (6), 1587 (2).

Compound 12—[Mono-N-carbobenzyloxy-1,6-diaminohexane]:

A solution of 21 mL (25.7 g, 150 mmol) of benzylchloroformate in 200 mL of dioxane was added dropwise to a stirred solution of 17.49 g (150 mmol) of 1,6-hexanediamine and 19.58 g (196 mmol) of KHCO$_3$ in 100 mL of dioxane and 300 mL of H$_2$O at 0°. The mixture was stirred at room temperature for 18 hours and then cooled to 0°. The mixture was acidified with 12N HCl and extracted with two 100 mL portions of Et$_2$O. The aqueous layer was neutralized with 10N NaOH and extracted with eight 100 mL portions of Et$_2$O. The basic extracts were combined, dried (Na$_2$SO$_4$), and concentrated to provide 5.03 g (13%) of crude compound 12 as a semisolid residue: $^1$H NMR (DMSO) d 1.22–1.51 (m, 8H), 2.54 (t, 2H), 3.02 (d of t, 2H), 5.05 (s, 2H), 7.30–7.48 (m, 5H).

Compound 13:

918 mg (4.45 mmol) of dicyclohexylcarbodiimide was added to a solution of 417 mg (1.78 mmol) of compound 5 and 409 mg (3.56 mmol) of NHS in 15 mL of THF at 0°. The mixture was stirred at 0° for 4.5 hours and a solution of 1.02 g (4.08 mmol) of compound 12 in 4 mL of THF was added. The mixture was stirred under $N_2$ at 5° for 18 hours. The concentrate was partitioned between 30 mL of EtOAc and two 30 mL portions of 1N HCl. The combined EtOAc layers were washed successively with 30 mL of $H_2O$ and 30 mL of saturated $NaHCO_3$ solution, dried ($MgSO_4$), filtered, and concentrated to provide 1.48 g of viscous residue. Purification by chromatography on silica gel (5/95 MeOH/$CH_2Cl_2$) gave 1.04 g (84%) of compound 13 as a sticky solid: $^1$H NMR (CDCl$_3$) d 1.33 (m, 8H), 1.43 (s, 9H), 1.51 (m, 8H), 3.18 (m, 4H), 3.26 (m, 4H), 3.81 (s, 2H), 3.85 (s, 2H), 4.90 (bd s, 2H), 5.10 (s, 4H), 6.81 (bd s, 1H), 7.28–7.40 (m, 10H), 8.05 (bd s, 1H).

Compound 14:

14.9 mL of trifluoroacetic acid was added to a solution of 5.16 g (7.45 mmol) of compound 13 in 14.9 mL of $CH_2Cl_2$ and the resulting mixture was stirred for 3 hours at room temperature. The mixture was concentrated under vacuum and redissolved in 57 mL of THF. 2.07 mL (1.51 g, 14.9 mmol) of $Et_3N$ was added to the mixture. 1.5 g (14.9 mmol) of succinic anhydride was added to the mixture and the mixture was then stirred for 18 hours. The mixture was partitioned between 75 mL of 1N HCl and four 75 mL portions of $CH_2Cl_2$. The combined $CH_2Cl_2$ layers were dried ($MgSO_4$), filtered, and concentrated to provide a solid. Crystallization from $CH_2Cl_2$/EtOAc/hexanes provided 3.84 g (74%) of compound 14 as a white solid: m.p. 122°; $^1$H NMR (MeOH) d 1.32 (m, 8H), 1.48 (m, 8H), 2.56 (m, 4H), 3.10 (t, 4H), 3.23 (m, 4H), 4.00 (s, 2H), 4.18 (s, 2H), 5.05 (s, 4H), 7.33 (m, 10H).

Compound 15—[4-Nitrophenyl ester of compound 14]:

887 mg (4.30 mmol) of dicyclohexylcarbodiimideo was added to a solution of 2.0 g (2.87 mmol) of compound 14 and 438 mg (3.15 mmol) of 4-nitrophenol in 15 mL of THF at 0°. The mixture was allowed to come to room temperature, stirred for 18 hours, and then cooled to 0°. 200 uL of acetic acid was then added and the mixture was stirred at 0° for 1 hour. The solids were removed by filtration and the filtrate was concentrated to an oil. Purification by chromatography on silica gel (92/8 $CH_2Cl_2$/IPA) and recrystallization of the resulting solid from $CH_2Cl_2$/hexanes provided 1.52 g (64%) of compound 15 as a white solid: m.p. 65–68°; $^1$H NMR (CDCl$_3$) d 1.30 (m, 8H), 1.47 (m, 8H), 2.71 (t, 2H), 2.90 (t, 2H), 3.17 (m, 4H), 3.25 (m, 4H), 3.92 (s, 2H), 4.08 (s, 2H), 4.86 (bd t, 1H), 4.95 (bd t, 1H), 5.09 (s, 4H), 6.28 (bd t, 1H), 7.23 (d, J=9 Hz, 2H), 7.32 (m, 10H), 8.22 (d, J=9 Hz, 2H), 8.95 (bd t, Compound 16:

A solution of 830 mg (0.99 mmol) of compound 15 in 7.5 mL of dioxane was added to a solution of 58 uL (59 mg, 0.40 mmol) of 2,2$^1$-(ethylenedioxy)-diethylamine (Fluka) and 111 mg (1.31 mmol) of $NaHCO_3$ in 7.5 mL of $H_2O$. The mixture was stirred at room temperature for 18 hours. The mixture was partitioned between 50 mL of 1N HCl and 50 mL of $CH_2Cl_2$. The $CH_2Cl_2$ layer was dried ($Na_2SO_4$), filtered, and concentrated provide 1.28 g of viscous oil. Purification by silica gel chromatography (84/15/1 $CH_2Cl_2$/MeOH/HOAc) gave 670 mg of compound 16 as a waxy solid: $^1$H NMR (CDCl$_3$) d 1.32 (m, 16H), 1.49 (m, 16H), 2.46 (m, 4H), 2.58 (m, 4H), 3.10–3.23 (m, 16H), 3.34 (m, 4H) 3.48 (m, 4H), 3.53 (s, 4H), 3.85 (s, 4H), 4.02 (s, 4H), 5.05 (s, 8H), 5.07 (underlying bd t, 2H), 5.15 (bd t, 2H), 7.30 (m, 20H), 7.40 (bd t, 2H), 8.60 (bd t, 2H).

Compound 35:

A solution of 613 mg (0.41 mmol) of compound 16 in 20.3 mL of EtOH and 10.1 mL of cyclohexene was stirred and purged with nitrogen. 20 mg of 10% Pd on carbon (Aldrich) was added and the mixture was heated in a 85° oil bath for 1.5 hours. When cool, the mixture was filtered through diatomaceous earth using 50/50 $H_2O$/acetone to rinse the flask and filter. The filtrate was concentrated under vacuum to give 448 mg (114%) of compound 35 as a waxy solid: $^1$H NMR (D$_2$O) d 1.39 (m, 16H), 1.59 (m, 16H), 2.57 (t, 4H), 2.65 (t, 4H), 2.88 (t, 8H), 3.23 (t, 4H), 3.29 (t, 4H), 3.42 (t, 4H), 3.65 (t, 4H), 3.71 (s, 4H), 4.06 (s, 4H), 4.30 (s, 4H).

Compound 17:

546 mg (6.50. mmol) of $NaHCO_3$ was added to a solution of 445 mg (0.406 mmol) of compound 35 in 9.5 mL of $H_2O$. A solution of 838 mg (3.25 mmol) of compound 10 in 14.4 mL of dioxane was added to the resulting mixture. The mixture was stirred for 7 hours at room temperature and partitioned between 50 mL of 0.1N $H_2SO_4$ and 50 mL of $CH_2Cl_2$. The $CH_2Cl_2$ layer was discarded, and the aqueous layer was extracted with two 50 mL portions of $CH_2Cl_2$, two 50 mL portions of 9/1 $CH_2Cl_2$/MeOH, 50 mL of 4/1 $CH_2Cl_2$/MeOH, and 50 mL of 3/2 $CH_2Cl_2$/MeOH. The extracts were combined and dried ($Na_2SO_4$), filtered, and concentrated to provide 282 mg of solid. Crystallization from EtOH/EtOAc/Et$_2$O gave 143 mg (24%) of compound 17 as a white solid: $^1$H NMR (CDCl$_3$/MeOH) d 1.33 (m, 16H), 1.55 (m, 16H), 2.55 (m, 8H), 3.21 (m, 16H), 3.39 (m, 4H), 3.55 (m, 4H), 3.81 (s, 8H), 3.95 (s, 4H), 4.12 (s, 4H). Anal. calc'd for $C_{54}H_{94}N_{12}O_{14}Br_4$: C, 44.57; H, 6.51; N, 11.55; Br, 21.97. Found: C, 45.85; H, 6.49; N, 11.37; Br, 19.90.

Compound 18—[1,5-Bis(N-carbobenzyloxy-6-aminohexanoamido)-3-azapentane]:

3.09 g (19.0 mmol) of carbonyldiimidazole was added to a solution of 5.05 g (19.0 mmol) of N-carbobenzyloxy-6-aminohexanoic acid in 25 mL of EtOAc at room temperature. The mixture was stirred for 15 hours and 1.02 μL (982 mg, 9.52 mmol) of diethylenetriamine was then added followed by 2.65 (1.93 g, 19.0 mmol) of $Et_3N$. The resulting mixture was stirred fur 4 hours, and the solid product was collected by filtration. Recrystallization (MeOH/EtOAc) gave 4.27 g (75%) of compound 18 as a fine grainy solid: m.p. 132°–133°; $^1$H NMR (CDCl$_e$) d 1.33 (m, 4H), 1.52 (m, 4H), 1.64 (m, 4H), 2.18 (t, 4H), 2.73 (t, 4H), 3.16 (m, 4H), 3.35 (m, 4H), 4.96 (bd s, 2H), 5.09 (s, 4H), 6.13 (bd s, 2H), 7.33 (s, 10H); Anal. calc'd for $C_{32}H_{47}N_5O_6$: C, 64.29; H, 7.50; N, 11.72. Found: C, 63.54; H, 7.75; N, 11.91.

Compound 19:

657 uL (880 mg, 3.2 mmol) of triethyleneglycol-bis-chloroformate (Aldrich) was added to a solution of 4.86 g (8.1 mmol) of compound 18 in 162 mL of pyridine in a 20° water bath. The mixture immediately formed a precipitate. The mixture was stirred for 16 hours and the resulting cloudy yellow solution was concentrated under vacuum. The concentrate was partitioned between 150 mL of EtOAc and two 150 mL portions of 1N HCl (making sure the aqueous layer was acidic). The aqueous layers were combined and extracted with a second 150 mL portion of EtOAc. The EtOAc layers were combined, dried ($MgSO_4$), filtered, and concentrated. The resulting residue was crystallized (EtOAc/hexanes/CHCl$_3$) to provide 1.92 g (43%) of compound 19 as fine yellow tinted crystals: m.p. 86°–91°; $^1$H NMR (CDCl$_3$) 1.31 (m, 8H), 1.52 (m, 8H), 1.62 (m, 8H), 2.20 (m, 8H), 3.20 (m, 8H), 3.39 (8, 16H), 3.62 (s, 4H), 3.68 (m, 4H), 4.26 (m, 4H), 5.08 (s, 8H), 5.32 (bd s, 4H), 7.31 (bd s, 4H), 7.37 (s, 20H); $^{13}$C NMR (CDCl$_3$) d 25.1, 26.2, 26.4, 29.6, 36.0, 36.2, 38.5, 38.8, 40.8, 64.5, 66.4, 69.1, 70.3, 128.0, 128.4, 136.7, 156.5, 156.9, 173.6; Anal. calc'd for $C_{72}H_{104}N_{10}O_{18}$: C, 61.87; H, 7.50; N, 10.02. Found: C, 61.68; H, 7.63; N, 9.95.

Compound 36:

3.5 mL of cyclohexene was added to a solution of 800 mg (0.57 mmol) of compound 19 in 5 mL of absolute EtOH. The solution was placed under nitrogen, 500 mg of 10% Pd on carbon was added, and the resulting mixture was refluxed with stirring for 2 hours. When cool, the mixture was filtered through diatomaceous earth and concentrated to give 500 mg (100%) of compound 36 as an oil: $^1$H NMR (50/50 $CDCl_3/CD_3OD$) d 1.21 (m, 8H), 1.49 (m, 8H), 1.62 (m, 8H), 2.19 (t, J=7.4 Hz, ell), 2.67 (t, J=7.4 Hz, 8H), 3.36 (bd s, 16H), 3.67 (s, 4H), 3.71 (m, 4H), 4.21 (m, 4H).

Compound 20:

3.9 g (46.4 mmol) of $NaHCO_3$ was added to a solution of 5.0 g (5.8 mmol) of compound 36 in 37.5 mL of dioxane and 12.5 mL of $H_2O$. The mixture was cooled to 0° in an ice bath and 8.7 g (34.8 mmol) of 4-nitrophenylbromoacetate, compound 10, was added. The mixture was stirred at 0° for 1 hour and 50 mL of 1N $H_2SO_4$ was slowly added. The mixture was extracted with three, 50 mL portions of EtOAc. The EtOAc extracts were discarded and the aqueous layer was extracted with six, 50 mL portions of 20/80 MeOH/$CH_2Cl_2$. The combined MeOH/$CH_2Cl_2$ layers were dried ($Na_2SO_4$), filtered, and concentrated. The residue was purified by silica gel chromatography (step gradient 9/1 $CH_2Cl_2$/MeOH then 85/15/5 $CH_2Cl_2$/MeOH/THF) to provide 3.62 g (46%) of compound 20 as a white solid: melting point 66.0°–70.5°. An analytical sample was prepared by preparative HPLC ($C_{18}$ reversed phase column, gradient 25/75/0.1 to 35/65/0.1 $CH_3CN/H_2O/CF_3CO_2H$ over 50 minutes, 225 nm) to give a clear oil which solidified on standing under vacuum to give a white solid: melting point 87°–89°; $^1$H NMR ($CDCl_2$) d 1.35 (m, 8H), 1.55 (m, 8H), 1.64 (m, 8H), 2.26 (m, 8H), 3.28 (m, 8H), 3.42 (bd s, 16H), 3.66 (s, 4H), 3.70 (m, 4H), 3.89 (S, 8H), 4.19 (m, 4H); $^{13}$C NMR ($CDCl_3$) d 25.1, 26.2, 28.8, 29.0, 38.5, 39.1, 40.0, 47.8, 48.3, 64.7, 69.1, 70.3, 157.0, 166.3, 174.9; MS m/e (relative intensity) MH+ [1341(25), 1343(60), 1345(70), 1347(56), 1349(21)], 705.6(100); Anal. calc'd for $C_{48}H_{84}N_{10}O_{14}Br_4$: C, 42.86; H, 6.29; N, 9.27; Br, 23.77. Found: C, 42.15; H, 6.28; N, 9.87; Br, 25.33.

Compound 21—[Tetrakis-(2-cyanoethoxymethyl)methane]:

This compound was prepared similarly to the method reported (Bruson, H. A., U.S. Pat. No. 2,401,607; Jun. 4, 1946). 27.3 mL (21.8 g, 411 mmol) of acrylonitrile was added to a stirred solution of 8.0 g (58.8 mmol) of pentaerythritol and 1.76 mL of a 40% aqueous solution of benzyltrimethylammonium hydroxide in 50 mL of $H_2O$. A reflux condenser was affixed and the mixture was heated under $N_2$ atmosphere with stirring at 40° for 16 hours and then at 60° for 24 hours. When cool, the mixture was acidified with 1 mL of concentrated HCl and transferred to a separatory funnel. The oil which settled to the bottom was collected, and the aqueous phase was extracted with three 40 mL portions of $CH_2Cl_2$. The oil and combined extracts were dried ($MgSO_4$), filtered, and concentrated to give 23.5 g of oil. Biscyanoethyl ether was removed by Khugelrhor distillation at 110° and 0.25 torr. The pot residue was crystallized from 1 L of $H_2O$ to give 8.43 g (41%) of compound 21 as white needles: m.p. 42.5° [Reported (*Macromolecules* 1991, 24, 1443–1444.) 39°–40°]; $^1$H NMR ($CDCl_3$) d 2.61 (t, J=6 Hz, 8H), 3.50 (s, 8H), 3.6 (t, J=6 Hz, 8H).

Compound 22—[Tetrakis-(2-carboxyethoxymethyl]methane]:

A solution of 5.0 g (14.35 mmol) of compound 21 in 21.5 μmL of concentrated HCl was stirred at 75° for 3 h; during this time a white precipitate formed. The aqueous HCl was removed under vacuum, and the mixture was concentrated twice from 25 mL of $H_2O$. The resulting 9.68 g of solid material was loaded onto a 45 mm i.d. column containing a 16.5 cm bed of DOW-1-X2 resin in the hydroxide form, and the column was eluted with 200 mL of $H_2O$ followed by 1N HCl. Fractions containing product, as evidenced by TLC (80/20/1 $CH_3CN/H_2O/HOAc$), were concentrated to give 1.21 g (21%) of 22 as an oil: $^1$H NMR ($D_2O$) d 2.46 (t, J=6 Hz, 8H), 3.22 (s, 8H), 3.55 (t, J=6 Hz, 8H).

Compound 23:

3.71 mL (6.06 g, 50.8 mmol) of thionyl chloride was added to a solution of 1.12 g (2.85 mmol) of compound 22 in 7.0 mL of THF. The mixture was stirred at room temperature for 3 hours and the solvents were removed under vacuum. The crude acid chloride was dissolved in 7 mL of THF. 2.12 mL (1.54 g, 15.24 mmol) of $Et_3N$ was then added to the solution. The mixture was stirred under $N_2$ and cooled to 0°. A solution of 3.60 g (12.74 mmol) of compound 4 in 5 mL of THF was added over a 1 minute period. The cooling bath was removed, and the mixture was stirred for 5.5 hours at room temperature and then partitioned between 25 mL of 1N HCl and four 25 mL portions of EtOAc. The EtOAc layers were combined, washed with brine, dried ($MgSO_4$), filtered, and concentrated to provide 3.46 g of viscous oil. Purification by chromatography on silica gel (95/5 $CH_2Cl_2$/MeOH) provided 1.26 g (30%) of compound 23 as a viscous oil: $^1$H NMR ($CDCl_3$) d 2.40 (t, 8H), 3.29 (s, 8H), 3.35 (m, 16H), 3.48–3.77 (m, 48H), 5.12 (s, 8H), 5.60 (bd, 4H), 6.85 (bd, 4H), 7.34 (s, 20H).

Compound 37:

4.0 mL of cyclohexene and 83 mg of 10% Pd on carbon were added to a solution of 142 mg (0.093 mmol) of compound 23 in 8.4 mL of EtOH under $N_2$. The mixture was refluxed with stirring in a 90° oil bath for 3 hours and, when cool, filtered through diatomaceous earth using $CH_2Cl_2$ to wash the filter and flask. The filtrate was concentrated to provide 70 mg (78%) of compound 37 as an oil: 1H NMR ($CDCl_3$) d 2.90 (t, 8H), 3.33 (s, 8H), 3.45 (t, 8H), 3.52–3.73 (m, 48H).

Compound 14:

40 mg (0.48 mmol) of $NaHCO_3$ and 104 mg (0.40 mmol) of compound 10 were added to a solution of 70 mg (0.098 mmol) of compound 37 in 2 mL of dioxane and 0.67 mL of $H_2O$. The mixture was stirred for 17 hours at room temperature and 0.5 mL of 1N $H_2SO_4$ was added, bringing the pH to 4. The mixture was concentrated, and the concentrate was purified by chromatography on G-10 Sephadex® (MeOH). The fractions containing product were concentrated under vacuum to provide 91 mg of oil. Purification of 36 mg of the crude product by HPLC ($C_{18}$, gradient 20/80/0.1 to 35/65/0.1 $CH_3CN/H_2O/CF_3CO_2H$) gave 19 mg (44%) of compound 24 as an oil: $^1$H NMR ($CDCl_3$) d 2.50 (t, 8H), 3.31 (s, 8H), 3.36–3.72 (m, 56H), 3.91 (s, 8H); $^{13}$C NMR ($CDCl_2$) d 28.8, 36.5, 39.7, 40.0, 67.2, 69.3, 69.5, 70.3, 166.6, 173.0. MS(FAB) m/e (relative intensity) MH$^+$ [1425 (15), 1427(63), 1429(75), 1431(64), 1433(12)], 577(100).

Compound 25a—[Bis-tolsylate of $PEG_{3350}$]:

6.47 mL of pyridine was added to a solution of 16.75 g (5.0 mmol) of polyethylene glycol (J. T. Baker, average molecular weight 3350 g per mol) which had been dried by azeotropic distillation (toluene) in 40 mL of $CH_2Cl_2$. The solution was placed under nitrogen and cooled to 0°. A solution of 7.63 g (40 mmol) of tosyl chloride in 40 mL of $CH_2Cl_2$ was added over a 25 minute period. The cooling bath was removed and the mixture was stirred at room temperature for 16 hours. The mixture was shaken with 80 mL of 1N HCl and the $CH_2Cl_2$ layer which contained emulsions was washed with 100 mL of $H_2O$. The $CH_2Cl_2$ layer was dried ($MgSO_4$), filtered, and concentrated. The residue was crystallized from $CH_2Cl_2/Et_2O$ to provide 16.82 g (92%) of compound 25a as a white solid: $^1H$ NMR ($CDCl_3$) d 2.50 (s, 6H), 3.48 (t, J=5 Hz, 4H), 3.55–3.77 (m, more than 600H, integral too large to be accurate), 3.83 (t, J=5 Hz, 4H), 7.44 (d, J=7 Hz, 4H), 7.94 (d, J=7 Hz, 4H).

Compound 26a —Diazido-$PEG_{3350}$:

A solution of 10.83 g (2.96 mmol) of compound 15a and 1.92 g (29.6 mmol) of $NaN_3$ in 30 mL of DMF was heated under $N_2$ in a 120° oil bath for 3 hours. When cool, the mixture was partitioned between 100 mL of $H_2O$ and 100 mL of $CH_2Cl_2$. The $CH_2Cl_2$ layer was diluted to 200 mL with $CH_2Cl_2$ and washed with 100 mL of 1N HCl, dried ($Na_2SO_4$), filtered and concentrated. The resulting waxy solid was recrystallized ($CH_2Cl_2/Et_2O$), and the resulting solids were further purified by chromatography on silica gel (gradient 98/2 to 95/5 $CH_2Cl_2$/MeOH) to provide 4.75 g (47%) of compound 26a as a waxy solid: TLC Rf 0.41 (9/1 $CH_2Cl_2$); $^1H$ NMR ($CDCl_3$) d 3.35 (t, J=5 Hz, 4H), 3.44 (t, J=5 Hz, 2H), 3.54–3.77 (m, approx. 300H, integral too large to be accurate), 3.79 (t, J=5 Hz, 2H).

Compound 27a—[Diamino-$PEG_{3350}$]:

473 mg of 10% Pd on carbon (Aldrich) was added to a solution of 4.75 g (1.39 mmol) of compound 26a in 140 mL of EtOH. The mixture was shaken under 60 psi of $H_2$ for 30 hours. Because the reaction was incomplete (TLC, 9/1 $CH_2Cl_2$/MeOH), another 473 mg of 10% Pd on carbon was added and the mixture was shaken under 60 psi of $H_2$ for another 5 hours. The mixture was then filtered through diatomaceous earth, concentrated under vacuum, and the concentrate was crystallized ($CH_2Cl_2/Et_2O$) to give 4.03 g (86%) of compound 27a as a white solid: $^1H$ NMR ($CDCl_3$) d 2.92 (t, 4H), 3.49 (t, 2H), 3.66 (t, 4H), 3.67 (m, approx. 300H, integral too large to be accurate), 3.86 (t, 2H).

Compound 28—[N-hydroxysuccinimidyl ester of compound 7]:

596 mg (2.89 mmol) of dicyclohexylcarbodiimide was added to a solution of 1.84 g (2.41 mmol) of compound 7 and 278 mg (2.41 mmol) of NHS in 12 mL of THF at 0° under $N_2$. The cooling bath was removed, and the mixture was stirred at room temperature for 16 hours. 250 uL of acetic acid was added to the mixture. Stirring was continued at room temperature for 1 hour. The mixture was then placed in a freezer for 2 hours. The solids were removed by filtration, and the filtrate was concentrated to give 2.27 g (110%) of crude compound 28 as a viscous oil. Compound 28 was difficult to purify without decomposition, so it was used directly to acylate diamino-PEG.

Compound 39a:

A solution of 900 mg (1.05 mmol) of compound 28 in 4.68 mL of dioxane was added to a solution of 877 mg (0.26 mmol) of compound 27a and 176 mg (2.10 mmol) of $NaHCO_3$ in 3.12 mL of $H_2O$ at 0°. The mixture was stirred for 2 hours and then partitioned between 25 mL of 1N HCl and two 25 mL portions of $CH_2Cl_2$. The combined $CH_2Cl_2$ layers were dried ($Na_2SO_4$), filtered, and concentrated to give a viscous oil. Purification by silica gel chromatography (gradient, 95/5 to 87/13 $CH_2Cl_2$/MeOH) yielded 695 mg (55%) of compound 29a as a waxy solid: $^1H$ NMR ($CDCl_3$) d 2.55 (bd, 8H), 3.39 (m, 16H), 3.44–3.72 (m, approx. 432H, integral too large to be accurate), 3.89 (s, 4H), 4.03 (s, 4H), 5.09 (s, 8H), 7.36 (s, 20H).

Compound 38a:

7.1 mL of cyclohexene was added to a solution of 688 mg (0.142 mmol) of compound 29a in 14.2 mL of EtOH under $N_2$. 284 mg of 10% Pd on carbon was added and the resulting mixture was refluxed for 2 hours. When cool, the mixture was filtered through diatomaceous earth with EtOH, and the filtrate was concentrated under vacuum to yield 550 mg (90%) of compound 38a as a waxy solid: $^1H$ NMR ($CDCl_3$) d 2.58 (m, 8H), 2.93 (m, 8H), 3.38–376 (m, approx. 550H), 4.00 (s, 4H), 4.13, (s, 4H).

Compound 30a:

A solution of 268 mg (1.04 mmol) of compound 10 in 4.65 mL of dioxane was added to a solution of 550 mg (0.13 mmol) of compound 38a and 175 mg (2.08 mmol) of $NaHCO_3$ in 3.11 mL of $H_2O$ at 0°. The mixture was stirred for 20 hours and partitioned between 50 mL of 1N $H_2SO_4$ and two 50 mL portions of $CH_2Cl_2$. The combined $CH=Cl_2$ layers were dried ($Na_2SO_4$), filtered, and concentrated to an oil. Purification by G-10 Sephadex® chromatography (MeOH) gave an amorphous solid which was crystallized ($EtOH/Et_2O$) to provide 378 mg (61%) of compound 30a as a white solid: $^1H$ NMR ($CDCl_3$) d 2.59 (bd s, 8H), 3.38–3.82 (m, approx. 500H, integral too large to be accurate), 3.88 (s, 8H), 3.98 (s, 4H), 4.10 (s, 4H); bromoacetyl determination (*European Journal of Biochemistry*, 1984, 140, 63–71): Calculated, 0.84 mmol/g; Found, 0.50 mmol/g.

Compound 25b—[Bis-tosylate of $PEG_{8000}$]:

2.3 mL (16.5 mmol) of triethylamine, followed by 3.15 g (16.5 mmol) of TsCl, was added to a solution of 12.0 g (1.5 mmol) of $PEG_{8000}$ (Aldrich, average molecular weight 8000 g/mmol) which had been dried by azeotropic distillation (toluene) in 30 mL of $CH_2Cl_2$. The mixture was stirred at room temperature for 18 hours and extracted with four, 50 mL portions of 1N HCl followed by 50 mL of saturated NaCl solution. The $CH_2Cl_2$ layer was dried ($Na_2SO_4$), filtered, and concentrated under vacuum to provide a waxy solid. Recrystallization ($CH_2Cl_2/Et_2O$) gave 11.0 g (92%) of compound 25b as a white solid: $^1H$ NMR ($CDCl_3$) d 2.38 (s, 6H), 3.40–3.89 (m, approx. 800H, integral too large to be accurate), 4.14 (m, 4H), 7.34 (d, J=8.2 Hz, 4H), 7.79 (d, J=8.2 Hz, 4H).

Compound 26b —[Diazido-$PEG_{8000}$]:

1.86 g (28.6 mmol) of $NaN_3$ was added to a solution of 10.8 g (1.3 mmol) of compound 25b in 30 mL of dry DMF. The mixture was heated under $N_2$ at 120° for 2.5 hours. When cool, the mixture was partitioned between 240 mL of $CH_2Cl_2$ and three 50 mL portions of 0.5N HCl. The $CH_2Cl_2$ layer was washed with 50 mL of saturated NaCl solution, dried ($Na_2SO_4$), filtered, and concentrated to give a solid. Purification by chromatography on silica gel (gradient 2/98 to 6/94 MeOH/$CH_2Cl_2$) and recrystallization of the purified product (MeOH/$Et_2O$) gave 6.95 (66%) of compound 26a as a white solid: TLC(Rf=0.33, 12/88 MeOH/$CH_2Cl_2$); $^1H$ NMR ($CDCl_3$) 3.39–3.86 (m).

Compound 27b —[Diamino-$PEG_{8000}$:

A solution of 6.9 g (0.86 mmol) of compound 26b in 150 mL of MeOH saturated with ammonia was sparged with nitrogen. 1.5 g of 10% Pd/C was added and the mixture was shaken under 65 psi of $H_2$ . After 20 hours, TLC analysis indicated that the reaction was incomplete. As a result, 200 mg of 10% Pd/C was added and shaking under 65 psi of $H_2$ was continued for another 20 hours. The mixture was filtered through diatomaceous earth and the filtrate was concentrated under vacuum. The resulting waxy solid was recrystallized (MeOH/$Et_2O$) to give 6.0 g (89%) of compound 27b as a white solid. $^1H$ NMR ($CDCl_3$) d 2.96 (t, J=5.1 Hz, 4H), 3.40–3.89 (m, approx. 700H, integral too large to be accurate).

Compound 29b:

221 mg (2.63 mmol) of $NaHCO_3$ was added to a solution of 3.0 g (0.375 mmol) of compound 27b in 10 mL of water and 3 mL of dioxane. 1.3 g (1.51 mmol) of compound 28 dissolved in 10 mL of dioxane was then added. The mixture was stirred for 24 hours and then 40 mL of 0.5N HCl was added. The mixture was extracted with four, 25 mL portions of $CH_2Cl_2$. The combined $CH_2Cl_2$ layers were dried ($MgSO_4$), filtered, and concentrated to an oil. Crystallization from $MeOH/Et_2O$ provided 2.0 g (58%) of compound 29b: $^1H$ NMR ($CDCl_3$) d 2.52 (m, 8H), 3.40–3.64 (m, approx. 700H, integral too large to be accurate), 3.89 (s, 4H), 4.02 (s, 4H), 5.09 (s, 8H), 7.35 (s, 20H).

Compound 38b:

123 mg of 10% Pd/C was added to a solution of 600 mg (0.063 mmol) of compound 29b in 5 mL of absolute EtOH and 2.5 mL of cyclohexene under nitrogen. This mixture was refluxed under nitrogen for 2 hours. The reaction mixture was filtered through diatomaceous earth and evaporated to give 549 mg (97%) of compound 38b as a white solid: $^1H$ NMR ($CDCl_3$) d 2.58 (m, 8H), 2.90 (m, 8H), 3.39–3.70 (m, approx. 700H, integral too large to be accurate), 4.05 (s, 4H), 4.15 (s, 4H).

Compound 30b:

100 mg (1.2 mmol) of $NaHCO_3$, followed by 84 mg (0.32 mmol) of compound 10, was added to a solution of 529 mg (0.059 mmol) of compound 38b in 2 mL of dioxane and 5 mL of water. After stirring for 12 hours, the reaction was acidified with 1N $H_2SO_4$ and extracted with four, 40 mL of $CHCl_3$. The combined $CHCl_3$ layers were dried ($MgSO_4$), filtered, and concentrated to give 503 mg of semi-solid residue. The residue was purified by chromatography on G-10 Sephadex® (MeOH) and crystallized ($MeOH/Et_2O$/hexanes) to give 215 mg (39%) of compound 30b as a white solid: $^1H$ NMR ($CDCl_2$) d 2.58 (m, 8H, 3.35–3.70 (m, approx. 700H, integral too large to be accurate), 3.89 (S, 8H), 4.01 (s, 4H), 4.16 (s, 4H); bromoacetyl determination (*European Journal of Biochemistry* 1984, 140, 63–71): Calculated, 0.42 mmol/g; Found, 0.27 mmol/g.

Compound 31—$PEG_{3350}$-bis-chloroformate]:

Two drops of dry pyridine, followed by 125 mg (0.418 mmol) of triphosgene, was added to a solution of 1.0 gram (0.249 mmol) of polyethylene glycol (J. T. Baker, average molecular weight 3350 g per mol) which had been dried by azeotropic distillation (toluene) in 12 mL of $CH_2Cl_2$. The mixture was stirred at room temperature for 20 hours and the solvent was evaporated under vacuum to give 1.0 g (100%) of compound 31 as a white solid: $^1H$ NMR ($CDCl_3$) d 3.40–3.65 (m, approx. 300H, integral too large to be accurate), 3.77 (m, 4H), 4.46 (m, 4H).

Compound 32:

A solution of 1.0 g (0.25 mmol) of compound 31 in 12 mL of 5:1 $CH_2Cl_2$/dioxane was added dropwise to a 50° solution of 600 mg (1.0 mmol) of compound 18 in 10 mL of dioxane and 1.5 mL of pyridine. The resulting cloudy solution was stirred for 72 hours. 25 mL of $CH_2Cl_2$ was added and the mixture was then filtered. The filtrate was evaporated and the semi-solid residue was purified by chromatography on G-10 Sephadex®. The resulting solid was crystallized ($CH_2Cl_2/Et_2O$) to give 829 mg (75%) of compound 32 as a faintly yellow solid: $^1H$ NMR ($CDCl_3$) d 1.30 (m, 8H), 1.40 (m, 8H), 1.61 (m, 8H), 2.18 (m, 8H), 3.17 (m, 8H), 3.40 (m, 16H), 3.62 (m, approx. 300H, integral too large to be accurate), 4.15 (m, 4H), 5.07 (s, 8H), 7.33 (m, 20H).

Compound 39:

100 mg of 10% Pd/C was added to a solution of 300 mg (0.065 mmol) of compound 32 in 5 mL of absolute EtOH and 2 mL of cyclohexene under nitrogen. This mixture was refluxed under nitrogen for 2 hours. The mixture was filtered through diatomaceous earth and the solvent was evaporated to give 237 mg (90%) of compound 39 as a white solid: $^1H$ NMR ($CDCl_3$) d 1.37 (m, 8H), 1.48 (m, 8H), 1.65 (m, 8H), 2.21 (m, 8H), 2.50 (m, 8H), 3.39 (m, 16H), 3.64 (m, approx. 300H, integral too large to be accurate), 4.19 (m, 4H).

Compound 33: 125 mg (0.67 mmol) of $NaHCO_3$ and 115 mg (0.44 mmol) of compound 10 was added to a solution of 225 mg (0.055 mmol) of 39 in 5 mL of dioxane and 5 mL of water. The resulting yellow solution was stirred at room temperature for 12 hours. The solution was then extracted with three 30 mL portions of $CH_2Cl_2$. The aqueous layer was acidified with 1N $H_2SO_4$ and extracted with three, 30 mL portions of $CH_2Cl_2$. The combined $CH_2Cl_2$ layers were dried ($MgSO_4$), filtered, and concentrated to provide a yellow oil. Purification by chromatography on G-10 Sephadex® (MeOH) and recrystallization of the resulting oil ($EtOH/Et_2O$) provided 182 mg (73%) of compound 33 as a white solid: $^1H$ NMR ($CDCl_3$) d 1.35 (m, 8H), 1.55 (m, 8H), 1.65 (m, 8H), 2.22 (m, 8H), 3.28 (m, 8H), 3.42 (m, 16H), 3.50–364 (m, approx. 300H, integral too large to be accurate), 3.87 (s, 8H), 4.18 (m, 4H); bromoacetyl determination (*European Journal of Biochemistry* 1984, 140, 63–71): Calculated, 0.87 mmol/g; Found, 0.73 mmol/g. Anal Calcd. for $C_{191}H_{375}O_{37}N_{10}Br_4$: C, 50.84; H, 8.33; N, 3.09; Br, 7.05. Found: C, 51.98; H, 8.34; N, 2.45; Br, 10.19.

Compound 40 - [4-Nitrophenyliodoacetate]: 5.15 g (25 mmol) of dicyclohexylcarbodiimide and 2.92 g (2.92 mmol) of 4-nitrophenol in 100 mL of EtOAc were added to a 0° solution of 3.72 g (20 mmol) of iodoacetic acid. The mixture was stirred at 0° for 1 hour and at room temperature for 2 hours. The solids were removed by filtration, and the filtrate was concentrated under vacuum. The resulting yellow solid was recrystallized (EtOAc/hexanes/trace HOAc) to yield 4.82 g (78%) of compound 40 as a yellow-brown solid: $^1H$ NMR ($CDCl_3$) d 4.00 (s, 2H), 7.39 (d, 2H), 8.40 (m, 2H).

Compound 41: 103 mg (1.22 mmol) of $NaHCO_3$, followed by 211 mg (0.692 mmol) of compound 40, was added to a solution of 110 mg (0.104 mmol) of compound 34 in 5 mL of dioxane and 5 mL of $H_2O$. The mixture was stirred for 18 hours and then concentrated under vacuum. Purification by chromatography on Sephadex® (MeOH) provided 140 mg (87%) of compound 41 as an oil. An analytical sample was prepared by preparative HPLC ($C_{18}$, gradient 20/80/0.1 to 25/75/0.1 $CH_3CN/H_2O$/TFA over 60 minutes, 225 nm): $^1H$ NMR ($CDCl_3$) d 2.59 (m, 4H), 2.65 (m, 4H), 3.44–3.62 (m, 60H), 3.77 (s, 4H), 3.78 (s, 4H), 4.02 (s, 4H), 4.21 (s, 4H).

Compound 42: 145 mg (0.935 mmol) of N-methoxycarbonylmaleimide was added with vigorous stirring to a solution of 171 mg (0.161 mmol) of compound 34 in 8 mL of dioxane, 2 mL of saturated $NaHCO_3$ solution, and 2 mL of $H_2O$ at 0° (*The Practice of Peptide Synthesis*, M. Bodansky and A. Bodansky, Springer-Verlag, New York, 1984, pages 29–31. Keller, O., Rudinger, *J. Helv. Chim. Acta* 1975, 58, 531.). After 15 minutes, 25 mL of dioxane was added, the cooling bath was removed, and stirring was continued for 45 minutes at room temperature. The mixture was extracted with two, 30 mL portions of $CHCl_3$ and the combined $CHCl_3$ layers were dried ($MgSO_4$), filtered, and concentrated to an oil. Purification by chromatography on G-10 Sephadex® (MeOH) gave 103 mg (45%) of compound 42 as an oil. An analytical sample was prepared by preparative HPLC ($C_{18}$, gradient 20/80/0.1 to 25/75/0.1 $CH_3CN/H_2O$/TFA over 65 minutes, 225 nm) to give an oil: $^1H$ NMR ($CDCl_3$) d 2.57 (m, 4H), 2.67 (m, 4H), 3.42–3.65 (m, 52H), 3.72 (m, 8H), 4.03 (s, 4H), 4.17 (s, 4H), 6.74 (s, 4H), 6.75 (s, 4H).

Compound 43 - [hydroxymethyl-tris-(2-cyanoethoxymethyl)methane]: 0.30 g (5.41 mmol) of KOH, followed by 23 mL (18.6 g, 350 mmol) of acrylonitrile, was added to a solution of 6.8 g (50 mmol) of pentaerythritol in 50 mL of $H_2O$. The mixture was stirred at room temperature for 16 hours, acidified with 1.5 mL of concentrated HCl solution, and extracted with two, 50 mL portions of $CH_2Cl_2$. The combined $CH_2Cl_2$ layers were dried ($MgSO_4$), filtered, and concentrated to give 16.97 g of liquid. Purification by chromatography on silica gel (EtOAc) yielded 8.49 g (51%) of compound 43 as a viscous oil: TLC, Rf=0.15 (EtOAc); $^1H$ NMR ($CDCl_3$) d 2.62 (t, 6H), 3.54 (s, 6H), 3.68 (t, 6H), 3.70 (s, 2H).

Compound 44 - [hydroxymethyl-tris-(2-carboxymethylethoxymethyl)methane: 78 mL of a saturated solution of HCl in MeOH was added to 5.45 g (15.6 mmol) of compound 43. The mixture was heated at reflux for 1 hour and, when cool, partitioned between 100 mL of $H_2O$ and four, 100 mL portions of $Et_2O$. The combined $Et_2O$ layers were washed successively with 100 mL of saturated $NaHCO_3$ solution and 100 mL of saturated NaCl solution, dried ($MgSO_4$), filtered, and concentrated to yield 4.74 g of viscous liquid. Purification by chromatography on silica gel provided 3.05 g (50%) of compound 44 as an oil: TLC, Rf=0.27 (80/20 EtOAc/hexanes); $^1H$ NMR ($CDCl_3$) d 2.58 (t, 6H), 3.43 (s, 6H), 3.61 (s, 2H), 3.69 (t, 6H), 3.70 (s, 9H); $^{13}$NMR ($CDCl_3$) d 34.8, 44.9, 51.6, 65.2, 66.9, 71.0, 172.1.

Compound 45: A mixture of 560 mg (1.4 mmol) of compound 44 and 1.69 g (6.0 mmol) of compound 4 was heated under nitrogen at 150° for 4 hours. The mixture was partitioned between 50 mL of EtOAc and 25 mL of 1N HCl, and the HCl layer was extracted with 25 mL of $CH_2Cl_2$. Combined EtOAc and $CH_2Cl_2$ extracts were washed with of saturated $NaHCO_3$ solution, dried ($K_2CO_3$), filtered, and concentrated to a viscous residue. Purification by chromatography on silica gel (gradient 95/5 to 90/10 $CH_2Cl_2$/MeOH) provided 300 mg (19%) of compound 45 as a viscous oil: TLC, Rf=0.24 (90/10 $CH_2Cl_2$/MeOH); $^1$NMR ($CDCl_3$) d 2.40 (t, 6H), 3.38 (s, 6H), 3.39–3.48 (m, 12H), 3.52–3.67 (m, 32H), 5.13 (s, 6H), 5.62 (bd s, 3H) 6.80 (bd s, 3H), 7.40 (s, 15H).

Compound 46: 104 mg of 10% Pd/C was added to a solution of 308 mg (0.269 mmol) of compound 45 in 10.4 mL of EtOH and 5.2 mL of cyclohexene under nitrogen. A reflux condenser was attached and the mixture was heated in an 85° oil bath for 1.5 hours. When cool, the mixture was filtered through diatomaceous earth and the filtrate was concentrated to provide 177 mg of residue. The residue was partially dissolved in 5.98 mL of dioxane. The resulting mixture was added to 386 mg (1.49 mmol) of compound 10 followed by a solution of 251 mg (2.99 mmol) of $NaHCO_3$ in 3.99 mL of $H_2O$. The resulting mixture was stirred under nitrogen for 18 hours and partitioned between 25 mL of 1N HCl and three 25 mL portions of $CH_2Cl_2$. The aqueous phase was extracted with three 25 mL portions of 3/1 $CH_2Cl_2$/MeOH and three 25 mL portions of 1/1 $CH_2Cl_2$/MeOH. The first two $CH_2Cl_2$ extracts were discarded and the remaining extracts were combined, dried ($Na_2SO_4$), filtered, and concentrated to give 102 mg of a viscous oil. Purification by HPLC ($C_{18}$, 23/77/0.1 $CH_3CN/H_2O$/$CF_3CO_2H$, 234 nm detection) provided 43 mg (14%) of compound 46 as a viscous oil: $^1H$ NMR ($CDCl_3$) d 2.48 (t, 6H); 3.40 (s, 6H), 3.44–3.54 (m, 14H), 3.56–3.62 (m, 12H), 3.63 (s, 12H), 3.67 (t, 6H), 3.91 (s, 6H), 6.90 (t, 3H), 7.10 (t, 3H); MS (FAB) m/e (relative intensity) $MH^+$ [1103(17), 1105(42), 1107(41), 1109(18)], $MNa^+$ [1125(38), 1127 (100), 1129(99), 1131(39)].

Compound 47 - S-(6-hydroxyhexyl)isothiuronium chloride: 11.1 g (146 mmol) of thiourea was added to a solution of 16.6 mL (20.0 g, 146 mmol) of 6-chlorohexanol in 49 mL, of ethanol and the mixture was refluxed for 24 hours. The mixture was cooled to 0° and the product crystallized. The crystals were collected by vacuum filtration and dried to give 28.4 g (92%) of compound 47 as a white solid: mp 122°–124°; $^1$H-NMR (DMSO) 1.40 (m, 4H), 1.65 (m, 2H), 3.21 (t, 2H), 3.41 (t, 2H), 9.27 and 9.33 (overlapping broad singlets, 4H); Anal. Calc'd for $C_7H_{17}ClN_2OS$: C, 39.51; H, 8.06; N, 13.17; S, 15.07. Found: C, 39.69; H, 8.00; N, 13.01; S, 15.16.

Compound 48 - 6-Mercaptohexan-1-ol: 9.25 g of NaOH pellets was added to a solution of 17.8 mg (83.6 mmol) of compound 47 in 120 mL of $H_2O$ and 120 mL of EtOH. The mixture was refluxed for 4 hours. The mixture was carefully concentrated to approximately 75 mL and the concentrate was purified by vacuum distillation to provide 7.4 g (66%) of compound 48: bp 95°–105°@5 mm Hg; $^1$H NMR ($CDCl_3$) 1.41 (m, 9H), 2.59 (dt, 2H), 3.69 (t with underlying brd s, 3H); $^{13}$C NMR ($CDCl_3$) d 24.5, 25.2, 28.0, 32.5, 33.9, 62.7; Anal. calc'd for $C_6H_{14}OS$: C, 53.68, H, 10.51; S, 23.89. Found: C, 53.35; H, 10.72; S, 23.60.

Compound 49 - Bis-(6-hydroxyhexyl)disulfide: A solution of 4.02 g (15.8 mmol) of $I_2$ in 90 mL of MeOH was added dropwise over a period of 10 minutes to a solution of 4.26 g (31.7 mmol) of compound 48 in 10 mL of MeOH and 13.7 mL (9.97 g, 98.5 mmol) of $Et_3N$ under $N_2$ atmosphere and cooled in an ice bath. The cooling bath was removed and the mixture was stirred at ambient temperature for 4 hours. The mixture was concentrated on the rotary evaporator and purified by silica gel chromatography (1:1 hexane/EtOAc) to provide 3.12 g (73%) of compound 49 as a pale yellow solid: TLC $R_f$ 0.18 (1:1 hexane/EtOAc); mp 38°–48°; $^1H$ NMR ($CDCl_3$) 1.15–2.20 (m, 16H, 2.73 (t, 4H), 3.70 (t, 4H); Anal. calc'd for $C_{12}H_{26}S_2O_2$: C, 54.09; H, 9.84; S, 24.06. Found: C, 54.85, H, 9.86; S, 24.11.

Compound 50 - Mono-O-(4',4"-dimethoxytriphenylmethyl)-bis-(6-hydroxyhexyl)disulfide: 3.97 g (11.7 mmol) of 4,4'-dimethoxytriphenylmethyl chloride was added to a solution of 3.12 g (11.7 mmol) of compound 49 and 45 mL of pyridine. The mixture was stirred at ambient temperature for 16 hours. Most of the pyridine was removed on the rotary evaporator and the residue was partitioned between 100 mL of saturated $NaHCO_3$ solution and 100 mL of EtOAc. The EtOAc layer was washed with 50 mL of saturated NaCl solution, dried ($Na_2SO_4$), filtered and concentrated to an oil. Purification by silica gel chromatography (9:1 $CH_2Cl_2$/EtOAc) yielded 2.84 g (43%) of compound 50 as a viscous oil: TLC $R_f$ 0.35 (9:1 $CH_2Cl_2$/EtOAc); $^1H$ NMR ($CDCl_3$) 1.41 (m, 8H), 1.65 (m, 8H), 2.70 (two overlapping triplets, 4H), 3.08 (t, 2H), 3.65 (t, 2H), 3.81 (s, 6H), 6.85 (d, 4H), 7.32 (m, 7H), 7.47 (d, 2H); HRMS (FAB, M+), calc'd for $C_{33}H_{44}O_4S_2$: 568.2681. Found: 568.2665.

Compound 51 - O-[14-(4',4"-Dimethyoxytriphenylmethoxy)-7,8-dithiotetradecyl]-O-(2-cyanoethyl)-N,N-diisopropylphosphoramidite: 458 mg (1.52 mmol) of O-cyanoethyl-N,N,N',N'-tetra-isopropylphosphorodiamidite in 0.5 mL of $CH_2Cl_2$ was added to a solution of 771 mg (1.36 mmol) of compound 50 and 116 mg (0.68 mmol) of diisopropylammonium tetrazolide in 6.8 mL of $CH_2Cl_2$ under $N_2$ atmosphere. The mixture was stirred for 4 hours and partitioned between 25 mL of $NaHCO_3$ and 3×25 mL of $CH_2Cl_2$. The combined $CH_2Cl_2$ layers were washed with saturated NaCl solution, dried ($Na_2CO_3$), filtered and concentrated to an oil. Purification by filtration through a 2" plug of basic alumina in a 25 mm column, eluting with 9:1 $CH_2Cl_2$/$Et_3N$ provided 831 mg (80%) of compound 51 as a viscous oil: $^1$H NMR (CDCl$_3$) d 1.25 (m, 12H), 1.45 (m, 8H), 1.70 (m, 8H), 2.72 (m, 6H), 3.09 (t, 2H), 3.65 (m, 4H), 3.87 (s, 6H), 3.91 (m, 2H), 6.89 (d, 4H), 7.35 (m, 7H), 7.49 (d, 2H); $^{31}$P NMR (CDCl$_3$ with 15% H$_3$PO$_4$ internal standard) 147.69; HRMS (FAB, MH+) calc'd for C$_{42}$H$_{62}$N$_2$O$_5$PS$_2$ 769.3839, found 769.3853.

Compound 52 - Trityl-HAD alcohol: 60 g (0.21 mol) of trityl chloride was added to a solution of 57 g (0.21 mole) of compound 49 and 60 mL of pyridine. This mixture was stirred at 100° C. for 19 hours. The reaction mixture was cooled to room temperature and filtered. The filtrate was diluted with 300 mL of methylene chloride and extracted by 200 mL of saturated sodium bicarbonate. The organic layer was dried over Na$_2$SO$_4$, filtered and concentrated to an oil. Purification by silica gel chromatography (gradient 9:1 hexanes: ethyl acetate 3:1 hexanes:ethyl acetate) yielded 55 g of compound 52 (50%): $^1$H NMR (CDCl$_3$) δ 1.38 (m, 8H), 1.63 (m, 8H), 2.66 (m, 4H), 3.04 (t, 2H), 3.62 (t, 2H), 7.25 (m, 9H), 7.42 (m, 6H). HRMS (FAB, M+) calc'd for C$_{31}$H$_{40}$O$_2$S 508.2470, found 508.2482.

Compound 53 - Trityl HAD Phosphoramidite: To a solution of 10 g (19.7 mmol) of compound 52 and 6.3 mL (36.2 mmol) of diisopropylethylamine in 90 mL of methylene chloride at 0° C. under argon was slowly added 4.5 mL (20.2 mmol) of 2-cyanoethyl-N,N-diisopropylchlorophosphoramidite. After stirring for 90 minutes, the reaction mixture was extracted twice with 100 mL of saturated sodium bicarbonate. The methylene chloride solution was dried over Na$_2$SO$_4$, filtered and concentrated to an oil. Purification by basic alumina chromatography (75:24:1, hexanes:ethyl acetate:triethylamine) provided 11.3 g (81%) of compound 53 as an oil: $^1$H NMR (CDCl$_3$) δ 1.18 (m, 12H), 1.37 (m, 8H), 1.62 (m, 8H), 2.6 (m, 6H), 3.04 (t, 2H), 3.60 (m, 4H), 3.82 (m, 2H), 7.26 (m, 6H), 7.44 (m, 9H). HRMS (FAB, MH+) calc'd for C$_{40}$H$_{58}$N$_2$O$_3$PS$_2$ 709.3626, found 709.3621.

Compound 54 - O-(tert-butyldimethylsilyl)-5-hexenol: 15.66 g (230 mmol) of imidazole and 20.0 g (130 mmol) of tert-butyldimethylsilyl chloride were added to a solution of 12.47 mL (10.4 g, 104 mmol) of 5-hexene-1-ol in 104 mL of DMF. The mixture was stirred at ambient temperature for 4 hours and partitioned between 200 mL of EtOAc and 100 mL of saturated NaHCO$_3$ solution. The EtOAc layer was washed with 100 mL of saturated NaHCO$_3$ solution, 100 mL of saturated NaCl solution, dried (MgSO$_4$), filtered, and concentrated to a volume of approximately 100 mL. Distillation under vacuum provided 70.07 g (90%) of compound 54: bp 130°–143° @100 mm Hg; $^1$H NMR (CDCl$_3$) 0.11 (s, 6H), 0.95 (s, 9H), 1.48 (m, 2H), 1.57 (m, 2H), 2.11 (dt, 2H), 3.66 (t, 2H), 5.03 (m, 2H), 5.86 (m, 1H); $^{13}$C NMR (CDCl$_3$) –5.25, 18.40, 25.21, 26.01, 32.35, 33.60, 63.09, 114.40, 138.92; Anal. calc'd for C$_{12}$H$_{26}$OSi: C, 67.22; H, 12.22. Found: C, 66.96; H, 12.16.

Compound 55 - 1-O-(tert-butyldimethylsilyl)-1,5,6-hexanetriol: To a solution of 9.86 g (46.0 mmol) of compound 54 in 92 mL of acetone was added a solution of 6.46 g (55.2 mmol) of N-methylmorphololine oxide in 23 mL of H$_2$O. To the mixture was added 443 µl of a 2.5% solution of OsO$_4$ in tert-butyl alcohol (360 mg of solution, 9.0 mg of OsO$_4$, 35 µmol) and 50 µL of 30% H$_2$O$_2$. The mixture was stirred for 16 h and a solution of 474 mg of sodium dithionite in 14 mL of H$_2$O was added. After another 0.5 h the mixture was filtered through celite. The filtrate was dried with MgSO$_4$ and filtered through 1" of silica gel in a 150 mL Buchner funnel using 250 mL portions of EtOAc to elute. Fractions containing product were concentrated to provide 11.0 g (96%) of 55 as a viscous oil: TLC R$_f$ 0.2 (1:1 hexane/EtOAc); $^1$H NMR (CDCl$_3$) 0.05 (s, 6H), 0.89 (s, 9H), 1.25 (m, 4H), 1.55 (m, 2H), 3.41 (dd, 2H), 3.62 (t, 2H), 3.71 (m, 1H); $^{13}$C NMR (CDCl$_3$) –5.23, 18.42, 21.91, 26.02, 32.68, 32.81, 63.16, 66.74, 72.24; HRMS (FAB, MH+), calc'd for C$_{12}$H$_{29}$O$_3$Si: 249.1886. Found: 249.1889.

Compound 56 - 5,6-(bis-O-benzoyl)-1-O-(tert-butyldimethylsilyl)-1,5,6-hexanetriol: 6.18 mL (7.48 g, 53.2 mmol) of benzoyl chloride was added to a solution of 5.29 g (21.3 mmol) of 55 in 106 mL of pyridine. The mixture was stirred for 18 hours and concentrated on the rotary evaporator. The mixture was partitioned between 100 mL of cold 1N HCl and 100 mL of EtOAc. The pH of the aqueous layer was checked to make sure it was acidic. The EtOAc layer was washed successively with 100 mL of H$_2$O and 100 mL of saturated NaCl, dried (MgSO$_4$), filtered, and concentrated to provide 10.33 g (99%) of compound 56 as a viscous yellow oil: TLC R$_f$ 0.45 (1:4 EtOAc/hexanes); $^1$H NMR (CDCl$_3$) d 0.05 (s, 6H), 0.88 (s, 9H), 1.59 (m, 4H), 1.85 (m, 2H), 3.14 (t, 2H), 4.49 (dd, 1H), 4.59 (dd, 1H), 5.54 (m, 1H), 7.45 (m, 4H), 7.58 (m, 2H), 8.05 (m, 4H).

Compound 57 - 5,6-(bis-O-benzoyl)-1,5,6-hexanetriol: 10.7 mL (10.7 mmol) of 1N tetrabutylammonium fluoride in THF was added to a solution of 2.62 g (5.36 mmol) of compound 56 in 10.9 mL of THF. The mixture was stirred for 16 hours. The mixture was partitioned between 25 mL of saturated NaHCO$_3$ solution and 3×25 mL of EtOAc. The combined EtOAc extracts were washed with saturated NaCl solution, dried (MgSO$_4$), filtered and concentrated to a viscous oil which was purified by silica gel chromatography (1:1 hexane/EtOAc) to provide 823 mg (41%) of compound 57 as a viscous oil; R$_f$ 0.14 (1:1 hexane/EtOAc); $^1$H NMR (CDCl$_3$) d 1.58 (m, 2H), 1.68 (m, 2H), 1.88 (m, 2H), 3.68 (t, 2H), 4.52 (dd, 1H), 4.62 (dd, 1H), 5.56 (m, 1H), 7.46 (m, 4H), 7.58 (m, 2H), 8.05 (m, 4H); $^{13}$C NMR (CDCl$_3$) d 22.08, 31.20, 31.30, 32.88, 62.92, 66.17, 72.63, 128.93, 130.19, 130.57, 133.62, 166.72, 166.86; HRMS (FAB MH+), calc'd for C$_{20}$H$_{23}$O$_5$: 343.1545. Found: 343.1553.

Compound 58 - O-[5,6-(bis-O-benzoyloxy)-hexyl]-O-(2-cyanoethyl)-N,N-diisopropylphosphoramidite: A solution of 989 mg (3.28 mmol) of O-cyanoethyl-N,N,N',N'-tetraisopropylphosphorodiamidite in 2.0 mL of CH$_2$Cl$_2$ was added to a solution of 1.02 g (2.98 mmol) of compound 57 and 255 mg (1.49 mmol) of diisopropylammonium tetrazolide (prepared by mixing acetonitrile solutions of diisopropylamine and tetrazole in a one-to-one mole ratio and concentrating to a white solid) in 14.9 mL of CH$_2$Cl$_2$. The mixture was stirred for 4 hours and then partitioned between 25 mL of CH$_2$Cl$_2$ and 25 mL of chilled saturated NaHCO$_3$ solution. The CH$_2$Cl$_2$ layer was washed with saturated NaCl solution, dried (Na$_2$SO$_4$), filtered, and concentrated. Purification by filtration through a 2" plug of basic alumina in a 25 mm column, eluting with 9:1 EtOAc/Et$_3$N, provided 1.5 g (93%) of compound 58 as a viscous oil: $^1$H NMR (CDCl$_3$) d 1.19 (m, 12H), 1.62 (m, 2H), 1.73 (m, 2H), 1.90 (m, 2H), 2.62 (dd, 2H), 3.53–3.92 (m, 6H), 4.53 (dd, 1H), 4.62 (dd, 1H), 5.58 (m, 1H), 7.48 (m, 4H), 7.60 (m, 2H), 8.09 (m, 4H); $^{31}$P NMR (CDCl$_3$ with 15% H$_3$PO$_4$ internal standard) d 148.2; HRMS (FAB, MH+), calc'd for C$_{29}$H$_{40}$O$_6$N$_2$P 543.2624. Found, 543.2619.

Compound 59 - [4(iodoacetamido)benzoic acid: This compound was prepared as described by Weltman, J. K., 1983 *Biotechniques* 1:148–152. Briefly, 708 mg (2.0 mmol) of iodoacetic anhydride was added to a solution of 137 mg (1.0 mmol) of para-aminobenzoic acid in 10 mL of dioxane. The mixture was stirred in the dark for 18 hours and partitioned between 25 mL of H$_2$O and 25 mL of EtOAc.

The EtOAc layer was washed with saturated NaCl solution, dried (MgSO$_4$), filtered and concentrated to yield 797 mg of a peach colored solid. Recrystallization from hexanes/EtOAc yielded 221 mg (72%) of 4-(iodoacetamido)benzoic acid as a white solid: mp 220°– 230°; $^1$H NMR (CDCl$_3$) d 3.86 (s, 2H), 7.68 (d, 2H), 7.91 (d, 2H), 10.60 (s, 1H).

Compound 60 - [4-(iodoacetamido)benzoyl derivative of α,ω-bis-(N-2-aminoethylcarbamoyl)polyethyleneglycol: 188 mg (0.909 mmol) of dicyclohexylcarbodiimide was added to a solution of 185 mg (0.606 mmol) of 4-(iodoacetamido)benzoic acid and 406 mg (0.121 mmol) of α,ω-bis-(N-2-aminoethylcarbamoyl)polyethyleneglycol (Sigma Chemical Co., St. Louis, Mo., dried by azeotropic distillation with toluene) in 2 mL of THF. The mixture was stirred for 2 hours and then six drops of acetic acid were added. 10 mL of CH$_2$Cl$_2$ was added and the mixture was kept in a freezer for 30 minutes. The mixture was filtered to remove solids and the filtrate was concentrated to a viscous residue. Purification by silica gel chromatography (gradient 99/1 to 96/4 CH$_2$Cl$_2$/MeOH) provided a solid which was triturated with MeOH to give 292 mg of a cream colored solid: $^1$H (CDCl$_3$) 3.48 (m, 8H), 3.63 (bd s, (CH$_2$CH$_2$O)$_n$, integral too large to integrate), 3.98 (s, 4H), 4.18 (bd m, 4H), 5.91 (bd m, 2H), 7.48 (bd m, 2H), 7.76 (d, 4H), 7.88 (d, 4H), 9.38 (bd m, 2H): iodoacetyl determination (*European Journal of Biochemistry* 1984, 140, 63–71): Calculated, 0.46 mmol/g; Found, 0.37 mmol/g.

EXAMPLE 3

Preparation of Activated Valency Platform Molecules and Conjugates

There are many ways to form conjugates of biological or chemical molecules and valency platform molecules. A particularly specific method uses a thiol attached to the biological or chemical molecule to react nucleophilically with a reactive "thiophillic" group on the valency platform molecule to form a thioether bond, but other combinations of reactive groups on the platform molecule and on the biological or chemical molecule can also be employed for attaching biological or chemical molecules covalently to a valency platform molecule. Table 1 contains a number of combinations of mutually reactive groups. The preference of any given method is dictated by the nature of the biological or chemical molecule (solubility, presence of other reactive groups, etc.).

TABLE 1

| Nucleophile | Mutually Reactive Group |
|---|---|
| amine, hydrazide | active ester, anhydride, acid |
| hydrazine | halide, sulfonyl halide, imidate ester, isocyanate, isothiocyanate, chloroformate carbodiimide adduct, aldehyde, ketone |
| sulfhydryl | haloacetyl, alkyl halide, alkyl sulfonate, maleimide, α,β-unsaturated carbonyl, alkyl mercurial, sulfhydryl, α,β-unsaturated sulfone |

The following examples illustrate how various valency platform molecules can be synthesized and conjugated with biological or chemical molecules. These examples show how peptides and oligonucleotides can be conjugated to valency platform molecules using some of the mutually reactive groups in Table 1. In addition to peptides and oligonucleotides, other biologically active molecules (proteins, drugs, etc.) can also be conjugated to valency platform molecules.

Combination 1:

Thiol on Platform - Thiophile on Ligand

Reaction Scheme 14

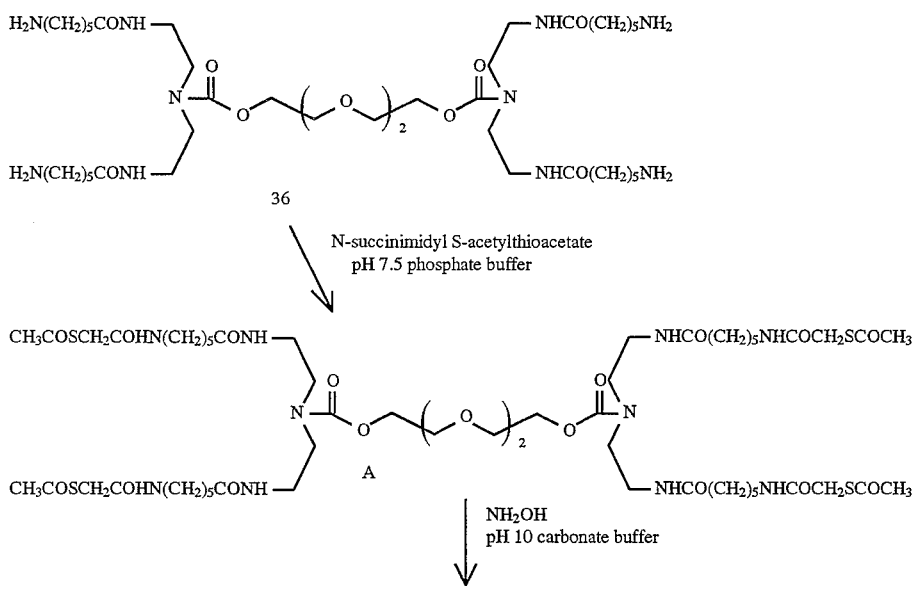

-continued
Combination 1:
Thiol on Platform - Thiophile on Ligand
Reaction Scheme 14

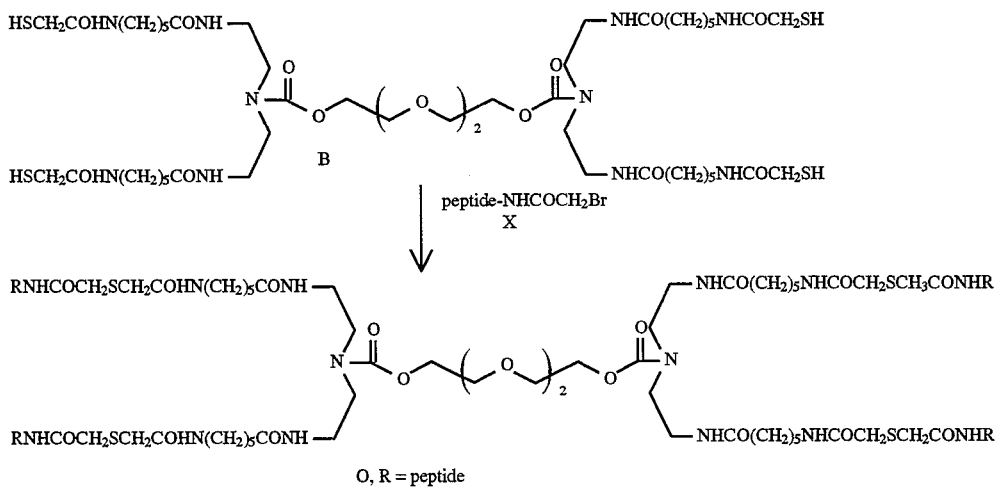

O, R = peptide

Compound A: Compound 36 (861 mg, 1.0 mmol) and 252 mg (3.0 mmol) of $NaHCO_3$ are dissolved in 20 mL of 1/1 dioxane/$H_2O$. The mixture is cooled to 0°, and a solution of 1.16 g (5.0 mmol) of N-succinimidyl-S-acetylthioacetate (Prochem Inc.) in 40 mL of dioxane is added to the stirred mixture. After 1 hour the mixture is extracted with $CH_2Cl_2$. The combined extracts are dried ($MgSO_4$), filtered, and concentrated. The crude product is purified by silica gel chromatography to provide A.

Compound B - Platform with Four Thiol Groups. A solution of 732 mg (0.55 mmol) of A in 7.3 mL of DMSO is added to 55 mL of helium sparged pH 10, 100 mM sodium carbonate, 10 mM $NH_2OH$ buffer. The mixture is kept under $N_2$ and stirred for 1 hour to obtain an approximately 10 mM solution of tetra-thiol platform B.

Compound X - Bromoacetylated Peptide: A peptide is synthesized with standard solid phase methods on a Wang (p-alkoxybenzyl) resin using FMOC chemistry. FMOC protected amino acids are added sequentially to the amino terminus. The final step involves coupling N-bromoacetylaminocaproic acid. The protecting groups are removed, and the peptide is removed from the resin with trifluoroacetic acid to give X which is purified by preparative reverse phase HPLC.

Peptide - Platform Conjugate, C. To the approximately 10 mmol solution of tetrathiol platform, B, in pH 10 buffer, is added an excess of a solution of bromoacetylated peptide, X, in DMSO. The peptide conjugate, C, is purified by preparative reverse phase HPLC.

Combination 2:
Amine on Platform - Activated Carboxylate on Peptide
Reaction Scheme 15

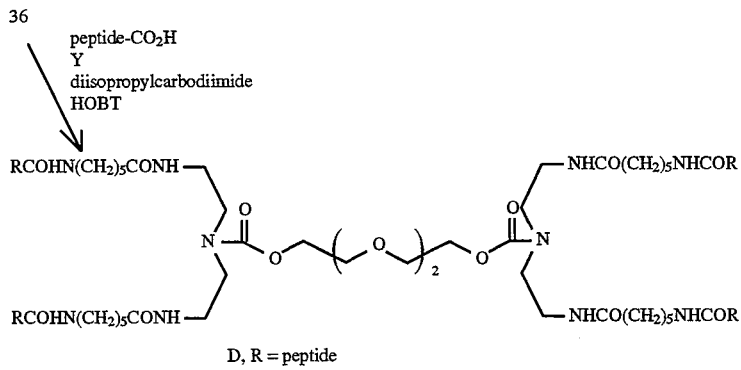

D, R = peptide

Compound Y - Peptide with Activated Carboxylate. A peptide is synthesized with standard solid phase methods on a Wang (p-alkoxybenzyl) resin, using TFA stable protecting groups (benzyl ester on carboxyl groups and CBZ on amino groups). Amino acid residues are added sequentially to the amino terminus. The peptide is removed from the resin with TFA to provide a peptide with one free carboxyl group at the carboxy terminus and all the other carboxyls and amines blocked. The protected peptide, Y, is purified by reverse phase HPLC.

Peptide - Platform Conjugate, D. Compound Y (0.3 mmol) is dissolved in 1 mL of DMF, and to the solution is added 0.3 mmol of diisopropylcarbodiimide and 0.3 mmol of HOBT. The solution is added to a solution of 0.025 mmol tetraamino platform, 36, in 1 mL of DMF. When complete, the DMF is removed under vacuum to yield a crude fully protected conjugate. The conjugate is dissolved in MeOH, and the solution is placed in a Parr hydrogenation apparatus with 100 mg of 10% Pd/C per gram of conjugate. The mixture is shaken under 60 psi $H_2$, and the deprotected conjugate, D, is purified by preparative reverse phase HPLC.

discarded, and the pellet is dried under vacuum. The pellet is dissolved in 3.3 mL of $H_2O$, and to the resulting solution is added a solution of 4.3 mg (0.005 mmol) of 36 in 2.0 mL of pH 8.0 100 mM sodium borate. To the resulting solution is added 250 uL (50 umol) of a 200 mM solution of Combination 3: Amine on Platform - Aldehyde on Oligonucleotide
Reaction Scheme 16

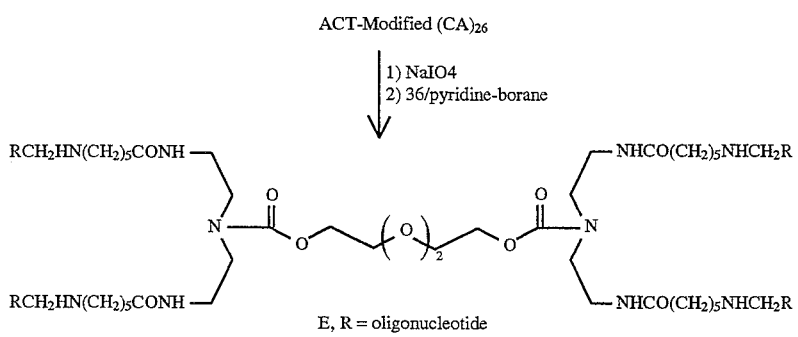

Oligonucleotide - Platform Conjugate, E. A 500 uL aliquot (100 umol) of a 200 mM solution of $NaIO_4$ is added to a solution of 1.0 g (400 mg of full length, 25 umol) of ACT-modified $(CA)_{25}$ in 19.5 mL of $H_2O$ at 0° in the dark. The mixture is kept at 0° for 40 minutes, and 50 mL of EtOH pyridine-borane complex in MeOH, and the mixture is kept at 37° for 4 days. The conjugate, E, can be purified by ion exchange chromatography.

Combination 4: Activated Carboxylate on Platform - Amine on Ligand
Reaction Scheme 17

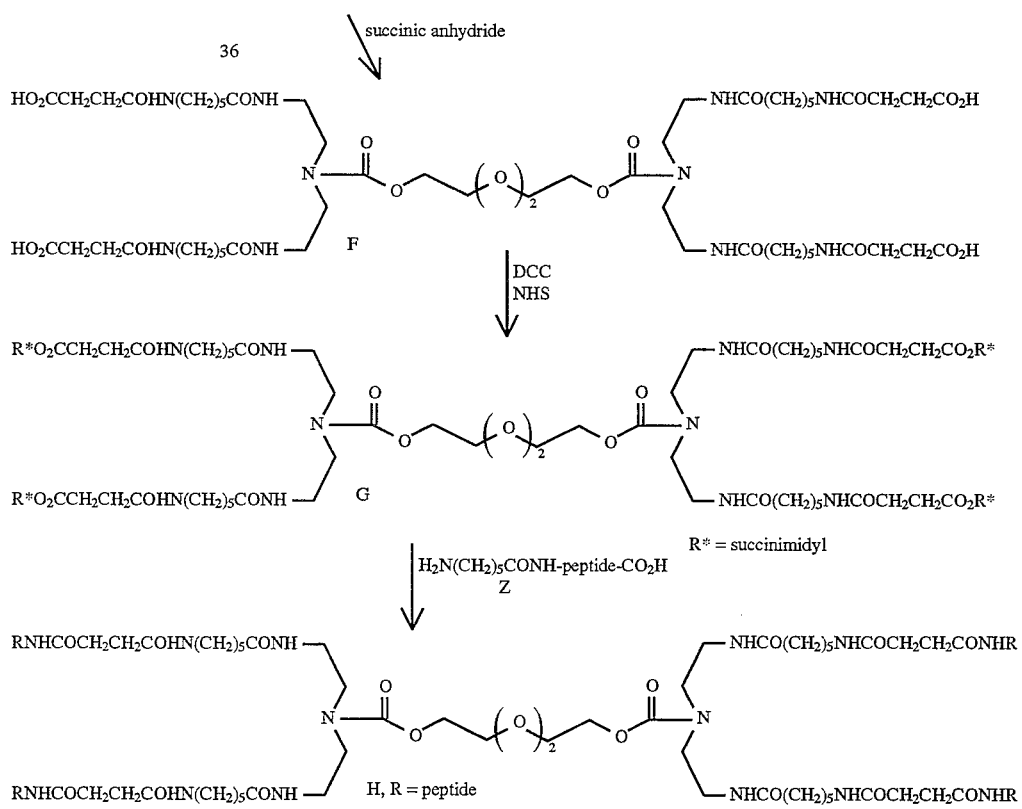

is added. The mixture is kept at −20° for 30 minutes and centrifuged for 5 minutes at 2000 RPM. The supernatant is Compound F - Platform With Four Carboxylic Acid Groups. Succinic anhydride (1.0 g, 10 mmol) is added to a solution of 861 mg (1.0 mmol) of 36 and 252 mg (3.0 mmol) of NaHCO₃ in 20 mL of 1/1 dioxane/H₂O, and the mixture is stirred for 16 h at room temperature. The mixture is acidified with 1N HCl and concentrated. The concentrate is purified by silica gel chromatography to provide F.

Compound G - platform with Four N-Succinimidyl Esters. A solution of 126 mg (0.1 mmol) of F and 46 mg (0.4 mmol) of N-sucinimidyl in 5 mL of anhydrous THF is prepared. The mixture is cooled to 0° and 103 mg (0.5 mmol) of dicyclohexylcarbodiimide is added. The mixture is stirred allowing to come to room temperature over several hours. The solids are removed by filtration, and the filtrate is concentrated to provide G which can be purified by silica gel chromatography.

Compound Z - Peptide with Amino Group. A peptide is synthesized with standard solid phase methods on a Wang (p-alkoxybenzyl) resin. Lysine ε-amines are protected as CBZ groups. Amino acid residues are added sequentially to the amino terminus using FMOC chemistry. The last residue added is N-FMOC-aminocaproic acid. After cleaving from the resin with trifluoroacetic acid, the FMOC group is removed with piperidine to provide a peptide with a free amine linker. The peptide, Z, is purified by reverse phase HPLC.

Peptide - Platform Conjugate, H. A solution of 0.05 mmol of Z and 0.1 mmol of Et₃N in 1 mL of DMF is prepared. To the solution is added a solution of 16.5 mg (0.01 mmol) of G in 1 mL of DMF. The mixture is stirred until the reaction is complete. To remove protecting groups, the conjugate is dissolved in MeOH, and the solution is placed in a Parr hydrogenation apparatus with 100 mg of 10% Pd/C per gram of conjugate. The mixture is shaken under 60 psi H₂, and the deprotected conjugate, H, is purified by preparative reverse phase HPLC.

of 861 mg (1.0 mmol) of 36 in 10 mL of THF, and the mixture is stirred at room temperature until complete by TLC. The mixture is partitioned between methylene chloride and a solution of 5% NaHCO₃. The extracts are dried (MgSO₄), filtered, and concentrated. The product, I, is purified by silica gel chromatography.

Peptide - Platform Conjugate, J. A solution of 0.05 mmol of Z and 0.1 mmol of Et₃N in 1 mL of DMF is prepared. To the solution is added a solution of 10.3 mg (0.01 mmol) of I in 1 mL of DMF. The mixture is stirred until the reaction is complete. To remove protecting groups, the conjugate is dissolved in MeOH, and the solution is placed in a Parr hydrogenation apparatus with 100 mg of 10% Pd/C per gram of conjugate. The mixture is shaken under 60 psi H₂, and the deprotected conjugate, J, is purified by preparative reverse phase HPLC.

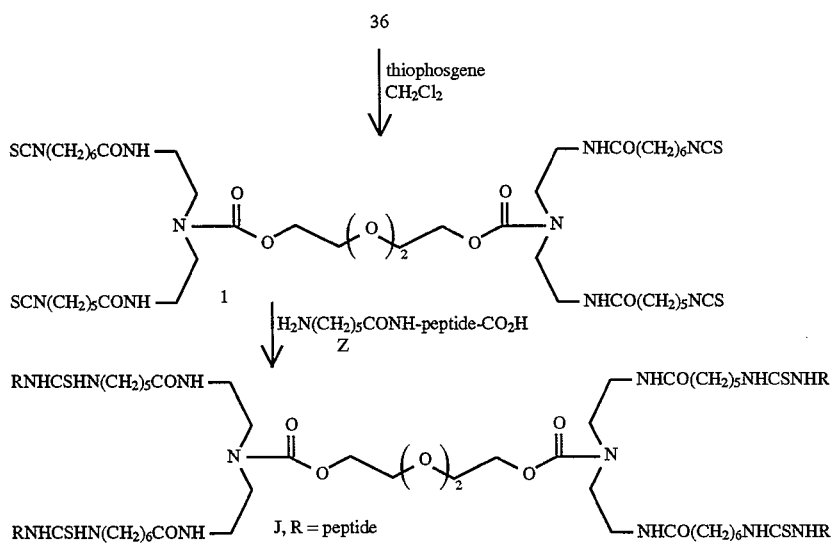

Combination 5: Isothiocyanate on Platform - Amine on Ligand
Reaction Scheme 18

Compound 1 - Platform with Four Isothiocyanates. Thiophosgene (381 uL, 575 mg, 5.0 mmol) is added to a solution Combination 6: Chloroformate on Platform - Amine on Ligand
Reaction Scheme 19

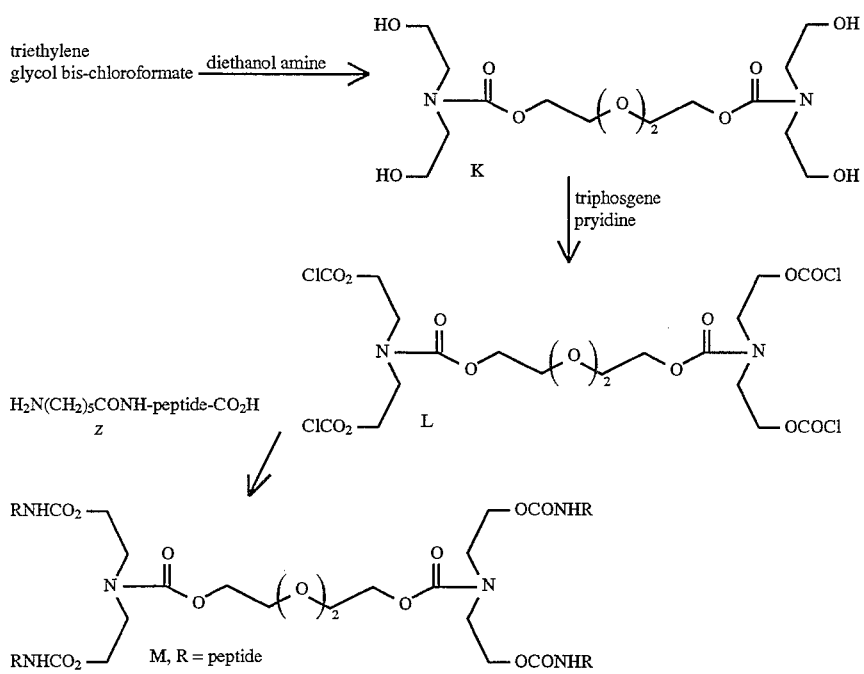

Compound K - platform with Four Hydroxyl Groups. A solution of 205 uL (275 mg, 1 mmol) of triethylene glycol bis-chloroformate in 5 mL of $CH_2Cl_2$ is added to a solution of 497 uL (525 mg, 5 mmol) of diethanolamine and 696 uL (506 mg, 5 mmol) of $Et_3N$ in 5 mL of $CH_2Cl_2$ at 0°. The mixture is allowed to warm to room temperature and stirred until complete as evidenced by TLC. The mixture is concentrated and the product, K, is isolated by silica gel chromatography.

Compound L - Platform with Chloroformate Groups. Pyridine (100 ul) followed by 1.19 g (4 mmol) of triphosgene are added to a solution of 412 mg (1 mmol) of K in 20 mL of $CH_2Cl_2$. The mixture was stirred at room temperature for 20 hours, and the solvent was evaporated under vacuum to give compound L.

Peptide - Platform Conjugate, M. A solution of 1 mmol of Z in 10 mL of pyridine is added to a solution of 132 mg (0.2 mmol) of L in 5 mL of 1/1 THF/pyridine. The mixture is stirred until the reaction is complete. Solvents are removed in vacuo. To remove protecting groups, the conjugate is dissolved in MeOH, and the solution is placed in a Parr hydrogenation apparatus with 100 mg of 10% Pd/C per gram of conjugate. The mixture is shaken under 60 psi $H_2$, and the deprotected conjugate, M, is purified by preparative reverse phase HPLC.

EXAMPLE 4

Synthesis of Conjugates Comprising Two Different Biological Molecules

It can be useful to conjugate more than one kind of biologically active group to a platform molecule. This example describes the preparation of a platform containing two maleimide groups, which react with a thiol-containing peptide, and two activated ester groups, which react with a drug containing a free amine. The resulting conjugate contains two peptides and two drug molecules as shown in Scheme 20.

Preparation of heteroactivated valency platform molecule Benzyl 6-aminocaproate tosylate salt, K: A mixture of 32 mmol of 6-aminocaproic acid, 51 mmol of p-toluenesulfonic acid, and 40 mmol of benzyl alcohol in 60 mL of toluene is refluxed using a Dean-Stark trap to remove water. When the reaction is complete, the mixture is cooled, and the product precipitates. The solid is collected by filtration and recrystallized from $EtOH/Et_2O$ to provide compound K.

Compound L: Dicyclohexylcarbodiimide (2 equivalents) is added to a solution of 1 equivalent of compound 5 and 2 equivalents of N-hydroxysuccinimide in THF. The mixture is stirred for 4 hours and 2.2 equivalents of compound K is added. The mixture is stirred until the reaction is complete as evidenced by TLC. The mixture is filtered and concentrated. The product is purified by silica gel chromatography.

Compound M: Compound L is treated with trifluoroacetic acid in $CH_2Cl_2$. When the reaction is complete, the mixture is concentrated under vacuum to provide compound M as the trifluoroacetate salt.

Compound N: Compound 6 (Scheme 2) is treated with trifluoroacetic acid in $CH_2Cl_2$. When the reaction is complete, the mixture is concentrated under vacuum to provide compound N as the trifluoroacetate salt.

Compound O: 3.2 mmol of triethyleneglycol bis-chloroformate is added to a solution of 4 mmol of compound M and 4 mmol of compound N in 162 mL of pyridine in a 20° water bath. The mixture is stirred until complete by TLC and concentrated under vacuum. The concentrate is dissolved in $CH_2Cl_2$ and washed successively with 1N HCl solution, 5% $NaHCO_3$ solution, and saturated NaCl solution. The $CH_2Cl_2$ layer is dried ($MgSO_4$), filtered and concentrated. The concentrate is dissolved in 10 mL, Of EtOH and 10 mL of 1M NaOH is added. The mixture is stirred for several hours, until no further reaction appears to take place by TLC. The mixture is acidified to pH 1 with 1N HCl and extracted with $CH_2Cl_2$. The $CH_2Cl_2$ layer is dried ($MgSO_4$), filtered, and concentrated. The product, O, is isolated by silica gel chromatography.

Compound P: Compound O is dissolved in EtOH and hydrogenated in a Parr shaker with 100 mg of 10% palladium on carbon per gram of O. The reaction is monitored for completeness by TLC. When the reaction is complete, the catalyst is removed by filtration, and the mixture is concentrated to yield compound P.

Compound O: 3 mmol of N-methoxycarbonylmaleimide is added to a solution of 1 mmol of compound P in 20 mL of dioxane and 5 mL of saturated $NaHCO_3$ at 0°. The mixture is stirred for an hour, acidified with 1N HCl, and extracted with $CH_2Cl_2$. The $CH_2Cl_2$ layer is dried ($MgSO_4$), filtered, and concentrated, and the product is purified by silica gel chromatography to yield O.

Compound R: 2 mmol of DCC is added to a solution of 1 mmol of O and 2 mmol of p-nitrophenol in $CH_2Cl_2$ and the mixture is stirred for 16 h. The solids are removed by filtration, and the filtrate is concentrated and purified by silica gel chromatography to yield R.

Conjugate with two peptides and two drug molecules, compound S: An excess of two equivalent of thiol-containing peptide is added to a solution of 1 equivalent of heteroactivated platform, R, in pH 7.5 phosphate buffer. The mixture is stirred for 1 hour, and excess of two equivalents of amine-containing drug is added. The conjugate, S, is isolated by reverse-phase HPLC or ion-exchange chromatography or a combination of both.

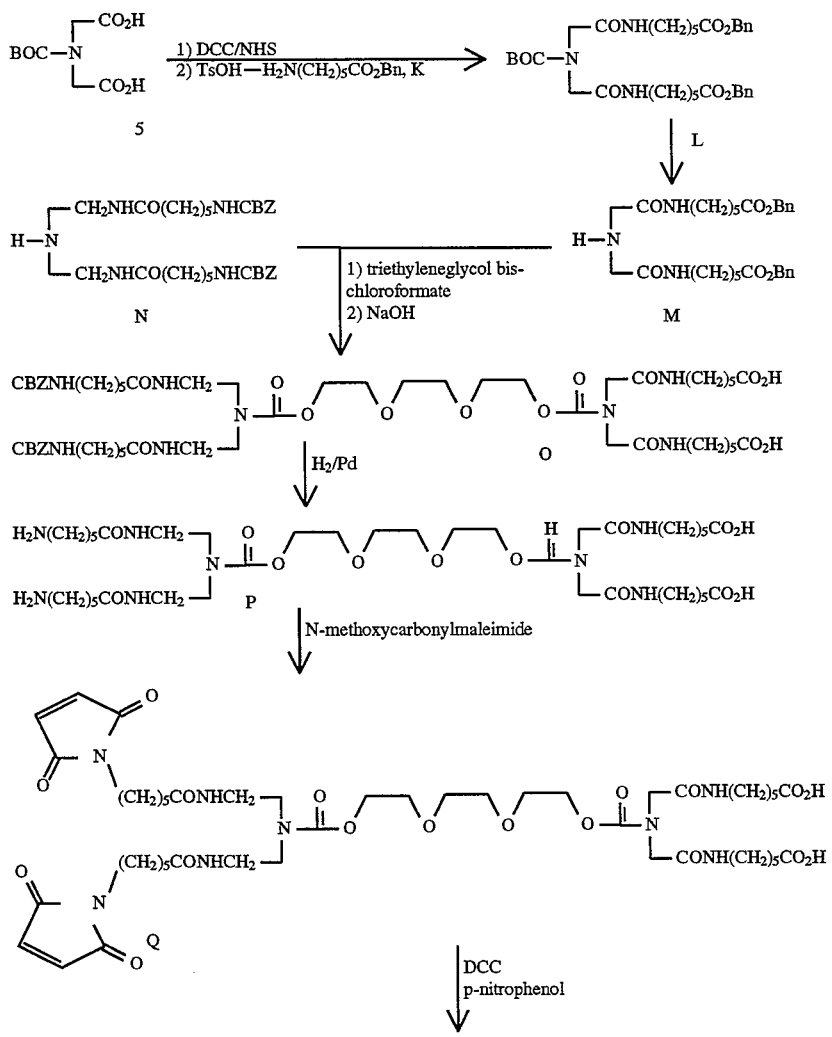

Reaction Scheme 20

-continued
Reaction Scheme 20

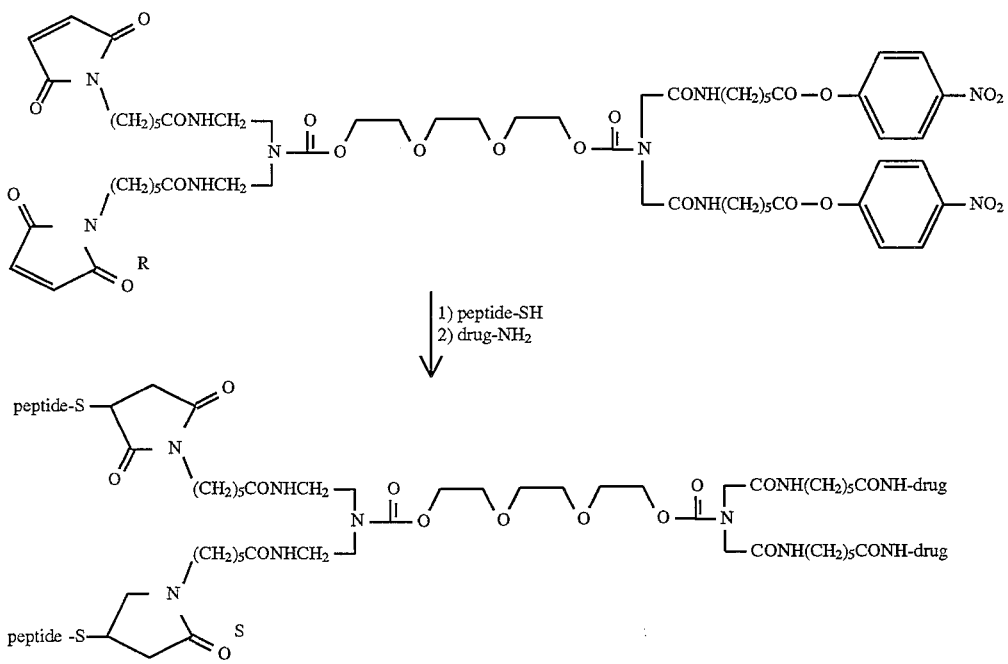

Synthesis and Testing of Conjugate 3-II
Reaction Scheme 21

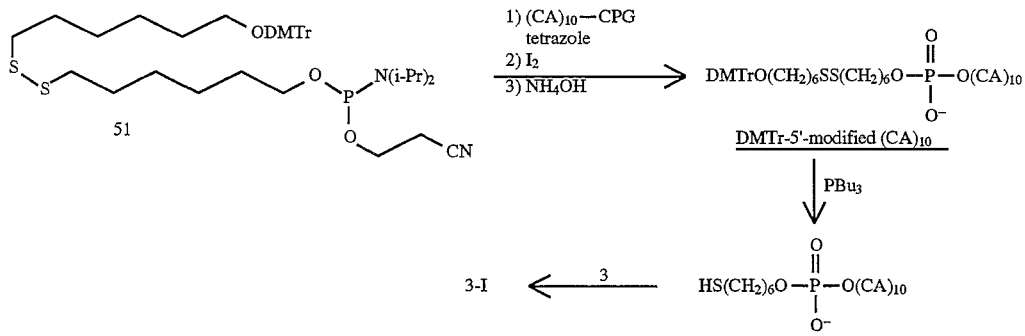

Preparation of DMTr-5'-Modified $(CA)_{10}$.

Figure 6B:
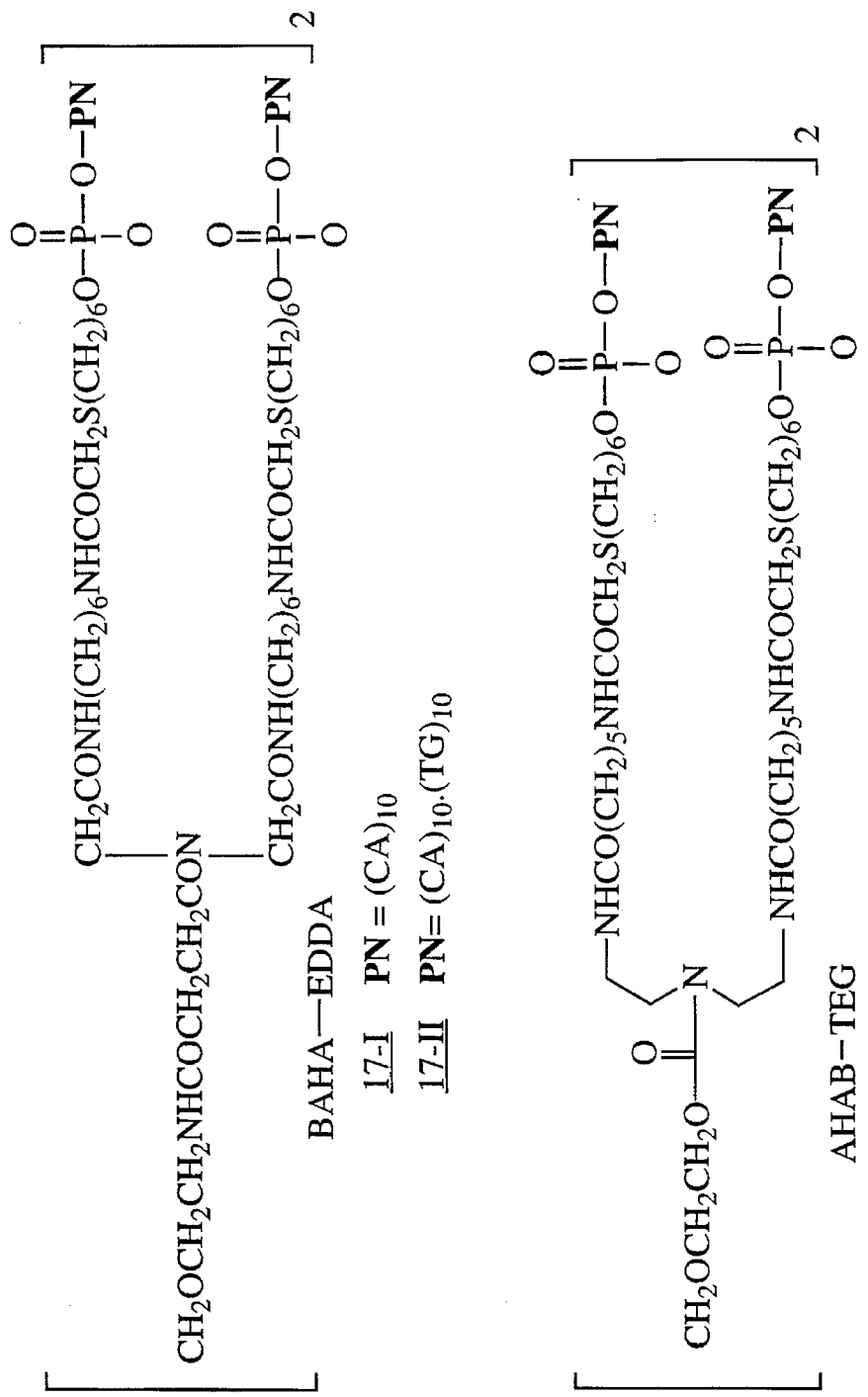
Figure 6C:
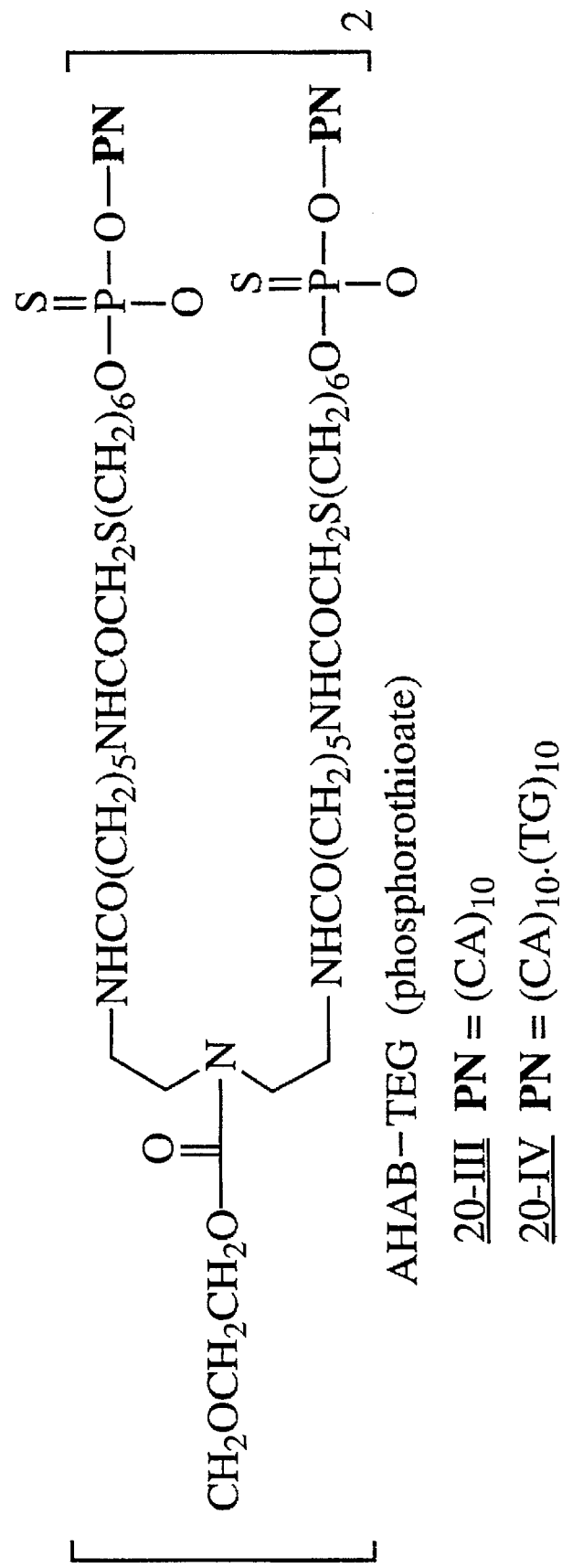

The polynucleotide d-[DMTr-(bzCp(CE)bzA)$_{10}$] was prepared on a Milligen 8800 Prep Scale DNA synthesizer (See FIG. 6A) following the manufacturer's protocols for DNA phosphoramidite synthesis. The synthesis was carried out on 10 g of DMTr-d-bzA-CPG support with a nucleoside loading of 30.0 μmol/g. The final DMTr blocking group was removed using the machine protocol. Milligen activator solution, Cat. No. MBS 5040 (45 mL) and 0.385 g of compound 51 (see Reaction Scheme 11) were added to the reaction and the suspension was mixed for 8 minutes by argon ebullition. The mixture was oxidized by the usual machine protocol and the support-bound polynucleotide was collected by filtration, air dried and treated with 100 mL of concentrated ammonia for 16 hours at 55° C. When cool, the mixture was filtered through a Gelman 10μ polypropylene filter. The filter was washed with 200 mL of 2 mM NaCl adjusted to pH 12 with NaOH. The filtrate was then applied to a Amicon chromatography column (0.45×9.4 cm, 150 mL) which had been packed with Q-Sepharose (Pharmacia) equilibrated first with 3M NaCl and then with 2 mM NaCl, pH 12. The column was eluted with 500 mL of a linear gradient (2 mM NaCl, pH 12 to mL 1.3M NaCl, pH 12), then washed with 1.3M NaCl, pH 12 until all U.V. absorbing material came off. Fractions which absorbed at 260 nm were further analyzed by polyacrylamide electrophoresis and those containing pure product were pooled. The pool (120 mL) was treated with 240 mL of cold isopropanol and stored for 30 minutes at −20° C. The precipitate was collected by centrifugation in a Sorvall RC 3B centrifuge using a model H-6000A rotor for 15 minutes at 3000 rpm and 4° C. to yield DMTr-5'-modified $(CA)_{10}$ (14946 $A_{260}$ units, 498 mg, 62.2 μM, 20% based on 300 μmol CPG nucleoside.)

Synthesis of a Tr-5'-Modified $(CA)_{10}$
Reaction Scheme 22

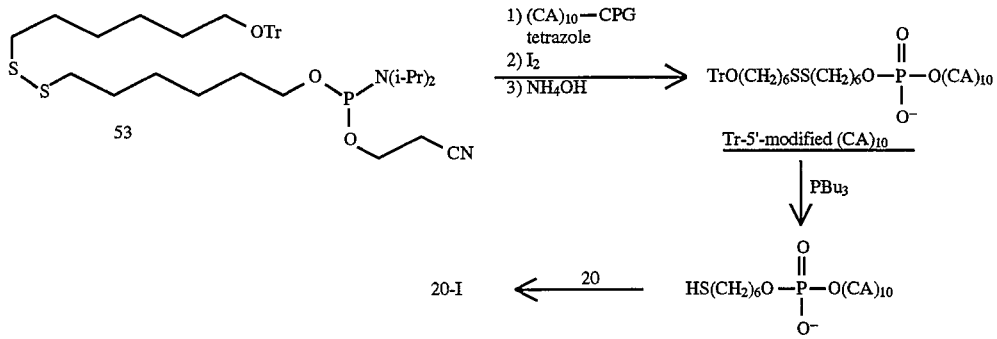

The synthesis of Tr-5'-modified $(CA)_{10}$ was carried out as described above for the synthesis of DMTr-5'-modified $(CA)_{10}$ (prepared as described in Reaction Scheme 11) by substituting compound 53 for compound 51.

Conjugation of DMTr-5'Modified Polynucleotides to Compound 3 (IA-DABA-PEG, Reaction Scheme 1) - Preparation of Conjugate 3-I In the conjugation procedures that follow, all the buffers and solutions employed were thoroughly sparged with helium and all reaction vessels were purged with argon before use. A solution of 11,568 $A_{260}$ units (48.2 µmol, assume molar extinction at 260 nm=240,000) of the DMTr-5'-modified $(CA)_{10}$ in 7.7 mL water was treated with 1 mL of 0.1M $NaHCO_3$ and 210 µL (876 µmol, 18 times molar excess) tributylphosphine for 0.5 hour at room temperature. The suspension was shaken from time to time. The suspension was treated with 0.8 mL of 3M NaCl and 16 mL of cold isopropanol. After 30 minutes at –20° C., the material was centrifuged at 3000 rpm for 20 minutes. The pellet was redissolved in 2 mL of water, 0.2 mL of 3M NaCl, treated with 4 mL isopropanol and recentrifuged. The pellet was briefly dried under vacuum and dissolved in 2.8 mL of water and 1 ml, of 0.1N $NaHCO_3$ which had been sparged with helium. 6.7 mg of compound 3 (IA-DABA-PEG) was added, and the mixture was kept for 16 hours at room temperature in the dark. The reaction mixture in a final volume of 6 mL was applied to a 5×91 (1800 M) Pharmacia column which was packed with Sephacryl 200 (Pharmacia). The column was eluted with 0.5M NaCl, 0.1M sodium borate, pH 8.3. A peristaltic pump was used and set to give a flow rate of approximately 2 mL per min., and fractions of 15 ml were collected. The absorbance of the fractions at 260 nm was measured. The fractions were also analyzed by polyacrylamide gel electrophoresis and those containing pure conjugate were pooled.

Hybridization of Conjugate 3-I - Preparation of Conjugate 3-II

The pooled fractions from above contained 726 $A_{260}$ units. The equivalent amount of $(TG)_{10}$ was added and the tube was heated at 90° C. for ten minutes and then allowed to cool to room temperature over 1.5 hours. An equal amount of isopropanol was added and the mixture kept for 3 hours at –20° C. After centrifugation at 3000 rpm for 20 minutes, the pellet was dissolved in 0.15M NaCl, 0.01M sodium citrate, pH 6.8. 53 mg of the hybrid was obtained. An aliquot of the material was diluted in the above buffer and the melting temperature of the duplex was determined in a Carey 3E spectrophotometer. The material had a Tm of 73.4° C. and 24.3% hyperchromicity. A 10 $A_{260}$ unit aliquot of the product was annealed with excess $(TG)_{10}$ as described above. This as well as unannealed conjugate and a $(TG)_{10}$ standard were analyzed by gel permeation HPLC on a Shodex Protein KW 8025 column on a Rainin HPLC instrument. The column was eluted isocratically with 0.05M $NaH_2PO_4$, pH 6.5, 0.5M NaCl. The run time was 12 minutes. The product had a retention time of 6.9 minutes and $(TG)_{10}$ 9.2 minutes. Comparison of the area under the peaks showed that 98.09% of the product was double stranded DNA. The conjugate is represented by the structure designated "Conjugate 3-II" in FIG. 6A.

EXAMPLE 6

Preparation of PN-KLH Conjugate

The PN-KLH conjugate was prepared according to the scheme below:

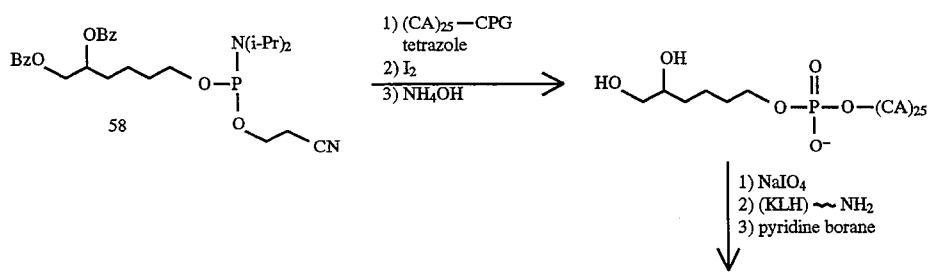

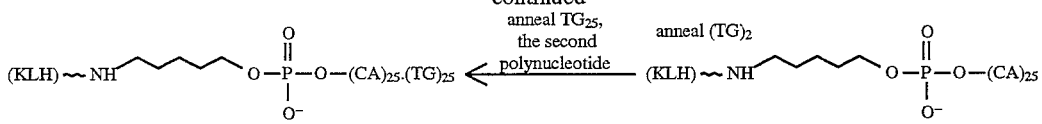

Synthesis of ACT-Modified $(CA)_{25}$

Compound 58 was coupled to $(CA)_{25}$ as the final step of automated synthesis which incorporates the elements of an acyclic triol moiety (ACT). Forty-nine sequential steps were carried out using alternating dC and dA phosphoramidites beginning with 10 g of DMT-d-bzA-CPG support with a nucleoside loading of 30 µmol/g. The DMTr blocking group was removed from the resulting d-[DMTr-$(B_2Cp(CE)B_2A)_{25}$] and 40 mL of activator solution (Milligen, Cat. No. MBS 5040) and 800 mg of compound 58 were added to the reaction mixture. The suspension was mixed for 8 minutes by argon ebullition and subjected to a conventional oxidation step. The support bound polynucleotide was removed from the reaction vessel, air dried, and treated with 100 mL of concentrated ammonia for 40 hours at 55°. When cool, the mixture was filtered through a Gelman 10 µm polypropylene filter and the filtrate was then purified by conventional ion exchange chromatography. Fractions which absorbed at 260 nm were further analyzed by polyacrylamide gel electrophoresis and those containing pure product were combined and precipitated with isopropanol to provide 510 mg (31.9 µmol, 10%) of the ACT-modified $(CA)_{25}$.

Synthesis of Single-stranded PN-KLH Conjugate

To a solution of 100 mg (2.5 µmol) of $NaIO_4$-treated ACT-modified $(CA)_{25}$ in 1.33 mL of 50 mM sodium borate pH 8.0 was added 31.3 mg (0.208 µmol) of KLH and 2.0 mg (31.8 µmol) of pyridine-borane. The mixture was kept at 37° C. for 72 h, and the product was purified by chromatography on S-200.

Hybridization of Single-stranded PN-KLH Conjugate with $(TG)_{25}$

The equivalent amount of $(TG)_{25}$ was added to the single-stranded PN-KLH conjugate and the tube was heated at 90° C. for ten minutes and then allowed to cool to room temperature over an hour and a half. Precipitation with isopropyl alcohol yielded 53 mg of product, PN-KLH; Tm (0.15 M NaCl, 0.01M sodium citrate, pH 6.8) 73.4°, 31.1% hyperchromicity; 98% double stranded as determined by HPLC comparison to standards consisting of sample annealed with excess $(TG)_{10}$, unannealed conjugate, and unannealed $(TG)_{10}$ (Shodex Protein KW 8025 column, 0.05M $NaH_2PO_4$, pH 6.5, 0.5M NaCl). This conjugate may be represented by the formula $$KLH\text{-}[NH(CH_2)_5OPO_2.O\text{-}(CA)_{25}: (TG)_{25}]_{\text{-}5}$$

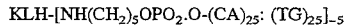

(assuming a molecular weight of $10^5$ for KLH) and is designated "PN-KLH."

Testing of Conjugate 3-II as a Tolerogen

Conjugate 3-II was tested for its ability to tolerize mice that had been immunized with an immunogenic form of the polynucleotide, PN-KLH.

Material and Methods

Mice: C57BL/6 female mice 6 weeks of age were purchased from Jackson Laboratories, Bar Harbor, Me. The mice were housed and cared for by NIH approved methods.

Immunization: The mice were primed, according to the method of Iverson (Assay for in vivo Adoptive Immune Response in Handbook of Experimental Immunology, Vol. 2 Cellular Immunology, Eds. D. M. Weir, L. A. Herzenberg, C. Blackwell and A. Herzenberg, 4th Edition, Blackwell Scientific Publications, Oxford) by injecting the mice, i.p., with 100 µg of PN-KLH precipitated on alum and with $2 \times 10^9$ formalin fixed pertussis organisms as an adjuvant. The mice were boosted with 50 µg of PN-KLH, in saline, i.p.

Coupling of PN to SRBC: Sheep Red Blood Cells (SRBC) in Alsevers were purchased from Colorado Serum Co., Denver, Colo., and used within two weeks. The SRBC were coated with $(CA)_{25}$: $(TG)_{25}$ (a 50 mer of CA:GT) by the method of Kipp and Miller ("Preparation of Protein-Conjugated Red Blood Cells with ECDI (Modification)" in Selected Methods In Cellular Immunology, (1980), Eds. B. B. Mishell and S. M. Shiigi, W. H. Freemen and Co., San Francisco, p. 103). Briefly, the SRBC were washed 4 times in cold saline, mixed with 2 mg of $(CA)_{25}$:$(TG)_{25}$ coupled to D-EK in 0.35M mannitol, 0.01M NaCl containing 10 mg of carbodiimide and incubated for 30 minutes at 4° C. The coated SRBC were washed twice with cold Balanced Salt Solution and resuspended to 10% (v/v).

Plaque assay: The number of anti-PN plaque forming cells (pfc) was determined using the Cunningham technique (Marbrook, J., "Liquid Matrix (Slide Method)", in Selected Methods in Cellular Immunology, (1980), Eds. B. B. Mishell and S. M. Shiigi, W. H. Freemen and Co., San Francisco, p. 86.) The number of IgG pfc were determined by elimination of IgM plaques using rabbit and anti-mouse IgG as described by Henry ("Estimation of IgG responses by Elimination of IgM Plaques" in Selected Methods in Cellular Immunology, (1980), Eds. B. B. Mishell and S. M. Shiigi, W. H. Freemen and Co., San Francisco, p. 91). Briefly, spleens were harvested and single cell suspensions made in balanced salt solution (BSS). Guinea pig serum was added to polynucleotide coated SRBC to give a final dilution of 1:9 guinea pig serum, and enough rabbit anti-mouse IgG was added to give a final dilution of 1:100 rabbit anti-mouse IgG. Equal volumes of the SRBC mixture and diluted spleen cells were mixed in microtiter wells and transferred to Cunningham chambers. Each spleen was tested individually and in triplicate. The edges of the chambers were sealed with paraffin and the chambers were incubated at 37° C. for 1 hour. The number of plaques were enumerated by viewing the chambers under an inverted microscope.

Results

Mice were primed with PN-KLH precipitated on alum with pertussis as an adjuvant (A&P) and seven weeks later divided into groups of 3 mice each. The mice were treated, i.p., with doubling dilutions of PN-DABA-PEG, Conjugate 3-II five days later all of the mice, including the control, were boosted with 50 µg of PN-KLH, in saline, i.p. Four days later, the spleens were harvested and the number of IgG pfc determined. As shown in Table 2, all doses of Conjugate 3-II tested showed a significant reduction in the number of pfc as compared to the control group.

TABLE 2

Tolerogenic Activity of Conjugate 3-II (PN-DABA-PEG)

| Dose (μg/mouse) | pfc/$10^6$ spleen cells Mean (S.D.) | % Reduction Mean |
| --- | --- | --- |
| None | 12865 (2846) | |
| 62.5 | 2868 (6809) | 77.7 |
| 125 | 3331 (939) | 74.1 |
| 250 | 3044 (1929) | 76.3 |
| 500 | 1809 (759) | 85.9 |
| 1000 | 2814 (554) | 78.1 |

EXAMPLE 7

Preparation and Testing of Conjugate 20-II

Conjugation of Tr5' Modified $(CA)_{10}$ to Valency Platform Molecule 20 - Preparation of Single-Stranded Conjugate 20-I 969 μL (789 mg, 3.89 mmol) of tri-n-butylphosphine was added to a solution of 918 mg (0.14 mmol) of Tr5'-modified $(CA)_{10}$ in 30 mL of $H_2O$ under argon atmosphere. The mixture was stirred for 1 hour and then 2.4 mL of a 3M NaCl solution was added followed by 42 mL of isopropanol which had been sparged with helium to remove oxygen. The mixture was placed in a freezer at −20° C. for 1 hour and then centrifuged at 3000 rpm for 30 minutes. The supernatant was removed and the oily residue was dissolved in 15.5 mL of helium sparged $H_2O$. 1.24 mL of 3M NaCl and 21.7 mL of helium sparged isopropanol was added to the mixture. The resulting mixture was then placed in a freezer at −20° C. for 1 hour and centrifuged at 3000 rpm for 20 minutes. The oily pellet was dried under vacuum for 18 hours to yield a solid. The solid was dissolved in 6 mL of helium sparged $H_2O$ to give a total volume of 6.4 mL. The amount of DNA was 863 mg as determined by UV absorbance at 260 nm (0.033 mg per unit of absorbance in pH 7.5 phosphate buffered saline). The solution was transferred to a 50 mL three-neck flask under argon. One neck of the flask had an argon gas inlet while the other two necks were stoppered. The total volume was adjusted to 7.7 mL with $H_2O$ and 0.87 mL of helium sparged 1M sodium phosphate buffer, pH 7.8, and 0.97 mL of MeOH. 1.9 mL (33.63 mg, 0.025 mmol) of a 17.7 mg/mL solution of compound 20 in MeOH was added to the mixture. The resulting mixture was stirred under argon for 20 hours and then diluted to 100 mL with a solution comprising 0.1M NaCl, 0.05M sodium phosphate, pH 7.5, and 10% MeOH. Purification was accomplished by chromatography on Fractogel® (equilibration: 0.1M NaCl, 0.05M sodium phosphate, pH 7.5, 10% MeOH: elution gradient 0.5M NaCl, 0.05M sodium phosphate, pH 7.5, 10% MeOH to 0.8 NaCl, 0.05M sodium phosphate, pH 7.5, 10% MeOH). Fractions containing pure conjugate 20-I as evidenced by HPLC and polyacrylamide gel electrophoresis were collected in 232 mL of eluent. The product and salts were precipitated by adding an equal volume of isopropanol and placing same in a freezer at −20° C. for 1 hour. Dialysis against $H_2O$ (2×100 vol) gave 335 mg of conjugate 20-I (32 mL of 10.47 mg/mL, 0.033 mg/absorbance unit at 260 nm, assumed).

Annealing of Conjugate 20-I with $(TG)_{10}$ to Form Double-Stranded Conjugate 20-II 150 mg (14.33 mL of 10.47 mg/mL based on 0.033 mg/absorbance unit at 260 nm) of conjugate 20-I and 157.5 mg (1.50 mL of 104.6 mg/mL based on 0.033 mg/absorbance unit at 260 nm) of $(TG)_{10}$ were placed into a 50 mL polypropylene centrifuge tube. The concentration was adjusted to 15 mg/mL by adding 2.0 mL of pH 7.2 10X PBS and 2.17 mL of $H_2O$. The mixture was placed in a 90° C. water bath and allowed to cool to room temperature over 1.5 hours. The concentration was determined to be 17.7 mg/mL by absorbance at 260 nm (0.050 mg/absorbance unit); transition melt temperature 67.5° C.; hyperchromicity 27%; osmolality 346; pH 7.2. For final formulation of conjugate 20-II, the solution was diluted to a final concentration of 12.7 mg/mL and an osmolality of 299 by adding 7.23 mL of pH 7.2½ X PBS and filtering through a 0.22μ filter.

Alternative Conjugation of Tr5'-Modified $(CA)_{10-20}$, Preparation of Single Stranded Conjugate 20-I 10 equivalents of tri-n-butylphosphine are added to a 10 mg/mL solution of Tr5'-modified $(CA)_{10}$ in He sparged with 100 mM pH 5 sodium acetate. The mixture is stirred for 1 hour and then precipitated with 1.4 volumes of isopropyl alcohol (IPA). The mixture is placed in the freezer at −20° C. for 1 hour and centrifuged at 3000 rpm for 20 minutes. The supernatant is removed and the pellet is dissolved to 10 mg/mL in He sparged IPA. The mixture is placed in the freezer at −20° C. for 1 hour and centrifuged at 3000 rpm for 20 minutes. The pellet is dried under vacuum for 18 hours to give a solid. A 50 mg/mL solution of the solid is prepared in He sparged 100 mM pH 10 sodium borate buffer. 0.25 equivalents of compound 20 as a 40 mg/mL solution in 9/1 MeOH/$H_2O$ is added to the mixture. The mixture is stirred at room temperature for 3–20 hours and diluted (0.1M NaCl, 0.05 sodium phosphate, pH 7.5, 10% MeOH). Purification is accomplished by chromatography on Factogel (equilibration; 0.1M NaCl, 0.05M sodium phosphate, pH 7.5, 10% MeOH: elution gradient; 0.5M NaCl, 0.05M sodium phosphate, pH 7.5, 10% MeOH to 0.8M NaCl, 0.05 sodium phosphate, pH 7.5, 10% MeOH). Fractions containing pure 20-I, as evidenced by HPLC and polyacrylamide gel electrophoresis, were collected. The product and salts are precipitated by adding an equal volume of IPA and standing in the freezer at −20° C. for 1 hour. Dialysis against $H_2O$ (2×10 vol) give 20-I.

Alternative Annealing of 20-I with $(TG)_{10-20}$ to Form Double Stranded Conjugate 20-II The methodology is essentially the same as that described above except that annealing is done at 70° C. instead of 90° C.

Second Alternative Conjugation of Tr5'-Modified (CA) $_{10-20}$-Preparation of Single Stranded Conjugate 20-I 4.8 mL of tri-n-butylphosphine was added to a solution of 7.75 g of Tr5'-modified $(CA)_{10}$ in 104 mL of Ar sparged 100 mM pH 5 sodium acetate under $N_2$. The mixture was stirred for 1 hour and then precipitated with 232.5 mL of IPA. The mixture was placed in a freezer for −20° C. for 1.5 hours, centrifuged at 3000 rpm for 20 minutes and then frozen at −20° C. for 24 hours. The supernatant was removed and the pellet was dissolved in 170 mL He sparged 0.3M NaCl solution. The mixture was again precipitated with 232 mL of Ar sparged IPA. The mixture was then placed in a freezer at −20° C. for 2 hours, centrifuged at 3000 rpm for 20 minutes and then from at −20° C. for 11 hours. The supernatant was decanted and the pellet was dried under vacuum for 12 hours to give a solid. A solution of the solid was prepared in 110 mL of Ar sparged 100 mM pH 10 sodium borate buffer. 406 mg of compound 20 as a solution in 4.4 mL of 9/1 MeOH/$H_2O$ was added to the mixture. The mixture was stirred at room temperature for 2 hours. The product mixture contained 62% of 20-I by high-pressure ion chromatography, Waters Gen Pak Fax column (100×4 mm), 60° C., linear gradient from 65%A/35%B to 18%A/82%B; A=0.05M NaH$_2$PO$_4$, pH 7.5, 1 mM EDTA, 10% MeOH (v/v); B=0.05M NaH$_2$PO$_4$, pH 7.5, 1M NaCl, 1 mM EDTA, 10% MeOH (v/v), eluting at 19.5 minutes.

Testing of Conjugate 20-II and Nonconjugated Controls

Figure 4:
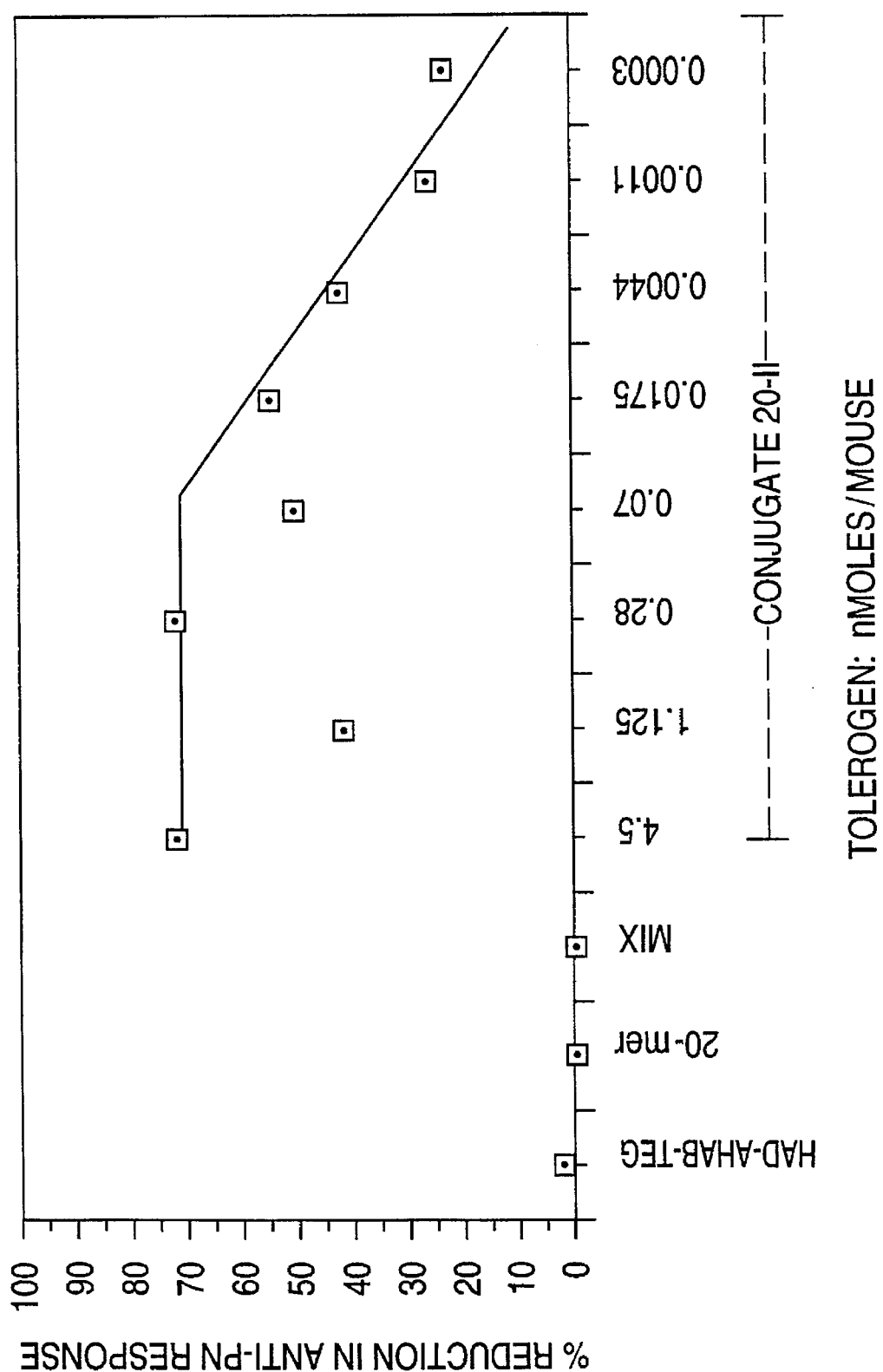
FIG. 4 shows the anti-PN response in mice primed with PN-KLH, treated with (PN)$_{20}$-HAD-AHAB-TEG, Conjugate 20-II, in the doses shown or with HAD-AHAB only, or the PN only or a mixture of each, then boosted with PN-KLH and bled 5 days later. Sera were tested by the Farr assay using radiolabeled PN at a concentration of $10^{-8}$M. The percent reduction was calculated and the data are presented. There were S mice per group.
Figure 7:
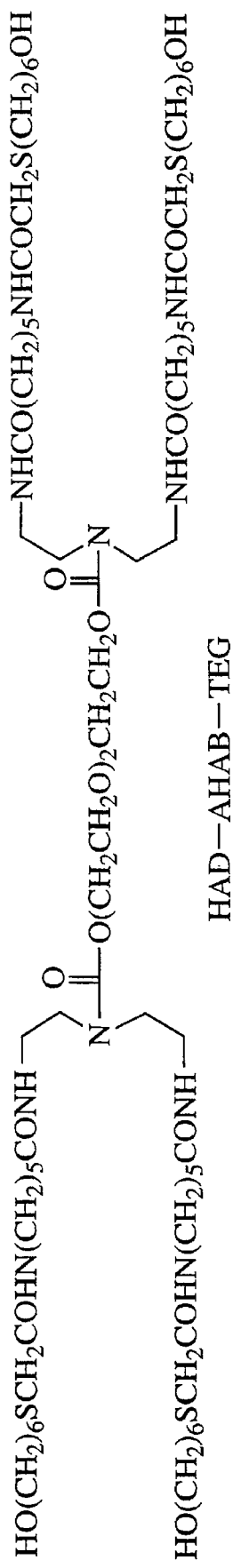
FIG. 7 shows the structures of the derivatized valency platform molecule "HAD-AHAB-TEG."

C57BL/6 mice were immunized with PN-KLH and A&P. After three weeks, groups of 5 mice/group were treated with either different doses of Conjugate 20-II or 4.5 nM HAD-AHAB-TEG (linker, HAD, attached to derivatized valency platform molecule, AHAB-TEG, see FIG. 7), or 18 nM (4×4.5) (CA)$_{10}$:(TG)$_{10}$, or a mixture of 4.5 nM HAD-AHAB-TEG plus 18 nM (CA)$_{10}$:(TG)$_{10}$, i.p.; and one group was not treated. The groups were given booster injections and the sera were collected and assayed as described in Example 6. The percent reduction of the anti-PN response is shown in FIG. 4. The anti-KLH responses of these mice was normal and were not significantly different than those shown in FIG. 2. The results clearly show that the anti-PN response was not affected by (i) the valency platform molecule alone, (ii) the PN alone, or (iii) a mixture of the two. The PN must be coupled to the nonimmunogenic valency platform molecule in order to induce tolerance.

Conjugate 20-II Causes a Reduction in the Number of PN-Specific Antibody producing Cells C57Bl/6 mice were immunized with PN-KLH, A&P. After three weeks, groups of 3 mice/group were treated with different doses of Conjugate 20-II, i.p; one group was not treated. After five days, all of the mice were given a booster injection of PN-KLH in saline, i.p., and then 4 days later their spleens were harvested and assayed for the number of PN-specific, IgG-producing cells using the hemolytic plaque assay. The results, shown in Table 3, clearly show that this conjugate reduced the number of PN-specific IgG-producing cells.

TABLE 3

REDUCTION IN THE NUMBER OF pfc BY Conjugate 20-II

| Group# | Dose μg/mouse | PN-specific pfc per 10$^6$ spleen cells (Mean & S.E.) | % Reduction |
|---|---|---|---|
| 1 | None | 5562 (2570) | |
| 2 | 274 | 982 (1871) | 82.3 |
| 3 | 91 | 1867 (1335) | 66.4 |
| 4 | 30 | 2247 (1606) | 59.6 |
| 5 | 10 | 6109 (2545) | 0 |
| 6 | 3 | 4045 (1411) | 27.3 |
| 7 | 1 | 4578 (2475) | 17.7 |
| 8 | 0.4 | 5930 (897) | 0 |

EXAMPLE 8

Testing of Conjugates as Tolerogens

Testing of Conjugate 17-II as a Tolerogen

Figure 2:
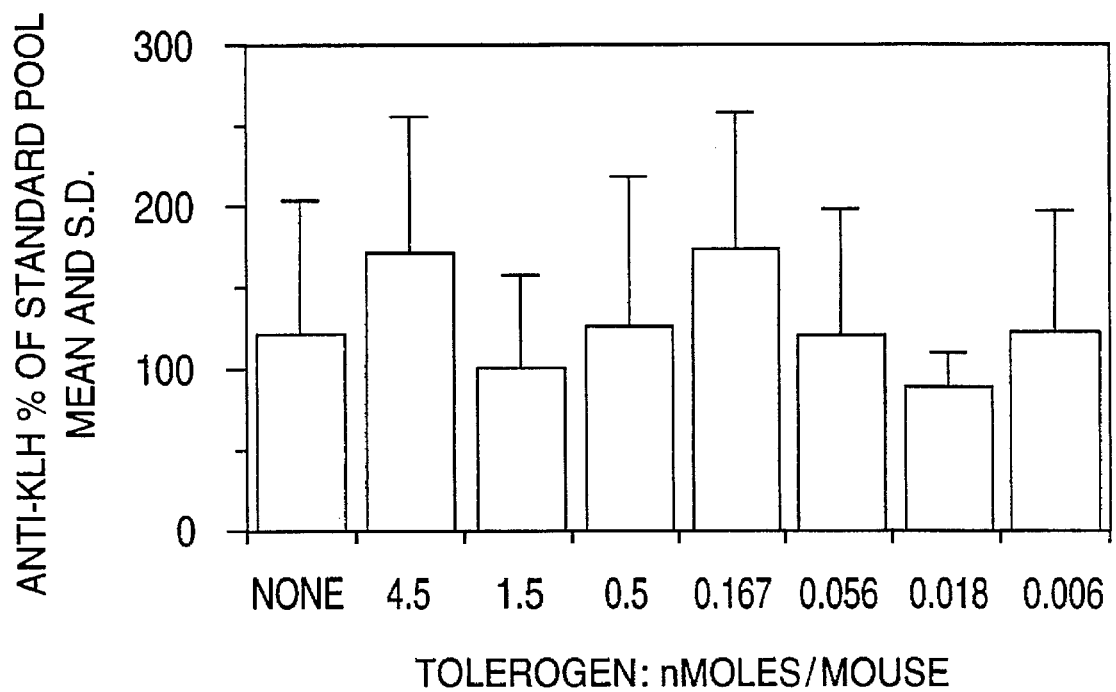
FIG. 2 shows the anti-KLH response in mice primed with PN-KLH, treated with [(PN)$_{20}$-BAHA]-EDDA, Conjugate 17-II, in the doses shown, given a booster injection of PN-KLH and then bled 5 days later. Anti-KLH antibodies were assayed by enzyme-linked immunosorbent assay (ELISA). The results are expressed as the percent of a standard pool of antisera. There were 5 mice per group.

C57BL/6 mice were immunized with PN-KLH, A&P. Three weeks later groups of 5 mice/group were treated with different doses of Conjugate 17-II intraperitoneally, (i.p.), and one group was not treated. Five days later all of the mice were given a booster injection of PN-KLH, in saline, i.p., and 7 days later the mice were bled. The sera were analyzed for anti-PN antibody by the Farr assay at a PN concentration of 10$^{-8}$M. The percentage reduction of the anti-PN response is shown in FIG. 1. The sera were also analyzed for anti-KLH antibodies using an ELISA assay. The results, expressed as the percentage of anti-KLH compared to a standard pool of anti-KLH sera, are shown in FIG. 2. The data in FIG. 1 show that this conjugate reduces the anti-PN response. The anti-KLH (platform molecule) response in all of the mice is normal (see FIG. 2).

Testing of Various of the 11 Series of Conjugates as Tolerogens

Figure 3:
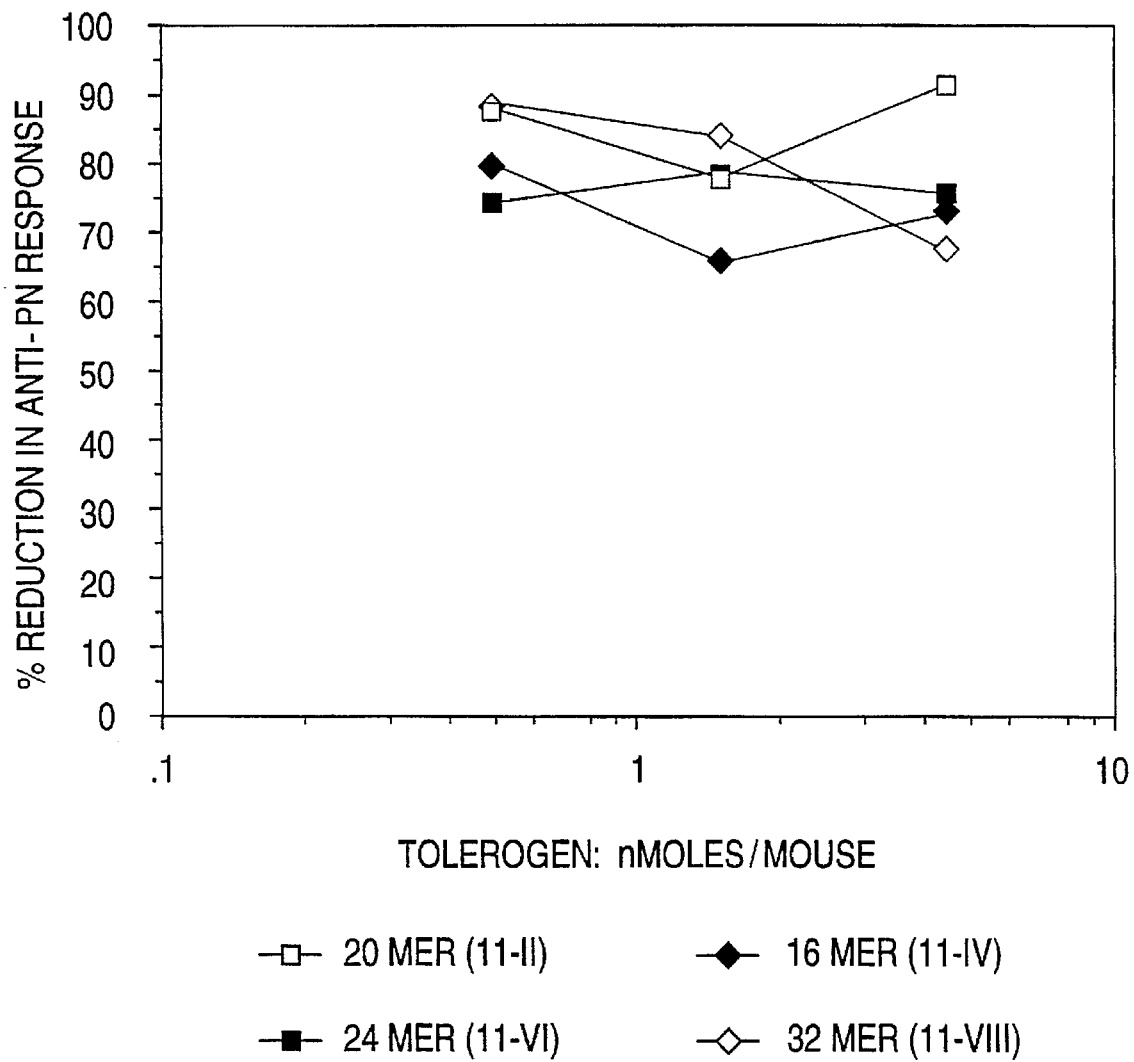
FIG. 3 shows the anti-PN response in mice primed with PN-KLH, treated with either [(PN)$_{16}$-BAHA$_{OX}$]-EDDA (Conjugate 11-IV), [(PN)$_{20}$-BAHA$_{OX}$]-EDDA (Conjugate 11-II), [(PN)$_{24}$-BAHA$_{OX}$]-EDDA (Conjugate 11-VI) or [(PN)$_{32}$-BAHA$_{OX}$]— EDDA (Conjugate 11-VIII) in the doses shown, given a booster injection of PN-KLH and then bled 5 days later. Sera were tested by the Farr assay using radiolabeled PN at $10^{-8}$ M. There were 5 mice per group.

Groups of three C57BL/6 mice/group were immunized with PN-KLH, A&P. After three weeks, two groups were treated with 3 different doses of either Conjugate 11-IV, Conjugate 11-II, Conjugate 11-VI or Conjugate 11-VIII, i.p., one group was not treated. These conjugates are described in FIGS. 6A–B and were prepared according to the methodology described above in Example 7. Five days later all of the mice were given a booster injection of PN-KLH, in saline, i.p., and 7 days later the mice were bled. The sera were analyzed for anti-PN antibody by the Farr assay at a PN concentration of 10$^{-8}$M. The results showing the percentage reduction in the anti-PN response are presented in FIG. 3. The anti-KLH responses in these mice were not significantly different than the responses shown in FIG. 2. All four conjugates significantly reduced the anti-PN response at all doses tested.

Conjugate 11-II Causes a Reduction in the Number of PN-specific Antibody Producing Cells C57Bl/6 mice were immunized with PN-KLH, A&P. After three weeks, groups of 3 mice/group were treated with different doses of Conjugate 11-II, i.p., one group was not treated. Five days later, all of the mice were given booster injections of PN-KLH in saline, i.p.; and 4 days later their spleens were harvested and assayed for the number of PN-specific, IgG-producing cells using the hemolytic plaque assay. The results of this experiment with different doses of Conjugate 11-II are shown in Table 4. These results clearly show that this conjugate reduced the number of PN-specific IgG-producing and that the reduction in antibody titer was not due to the clearance of serum antibody bound to conjugate.

TABLE 4

REDUCTION IN THE NUMBER OF pfc BY Conjugate 11-II

| Group# | Dose μg/mouse | PN-specific pfc per 10$^6$ spleen cells (Mean & S.E.) | % Reduction (SD) |
|---|---|---|---|
| 1 | None | 10845 (1308) | |
| 2 | 263 | 3613 (547) | 66.23 (8.6) |
| 3 | 87 | 3462 (1041) | 64.98 (17) |
| 4 | 29 | 7354 (1504) | 29.5 (23.8) |
| 5 | 9 | 6845 (2031) | 30.9 (32.2) |
| 6 | 3 | 7982 (223) | 26.8 (3.52) |
| 7 | 1 | 6043 (545) | 44.5 (7) |
| 8 | 0.4 | 9343 (1251) | 13 (19.8) |

EXAMPLE 9

Preparation of HADpS-(CA)$_{10}$ - Conjugate 20-IV

A modified polynucleotide with a phosphorothioate joining the linker to the 5' end was prepared. Synthesis of the twentymer, (CA)$_{10}$, and the addition of the HAD linker to the polynucleotide was carried out according to the methodology of Example 5 except for the following. In the final oxidation step, the iodine solution was replaced with a 0.05M solution of 3H-1,2-benzodithiole-3-one 1,1 dioxide (Glen Research, Sterling, Va.) in acetonitrile. Sulfurization was carried out according to the manufacturer's instruction.

Ammonia treatment and purification were carried out as in Example 5. Conjugation of the polynucleotide to the AHAB-TEG valency platform were carried out according to the methodology of Example 5.

Testing of Conjugate 20-IV as a Tolerogen

Figure 5:
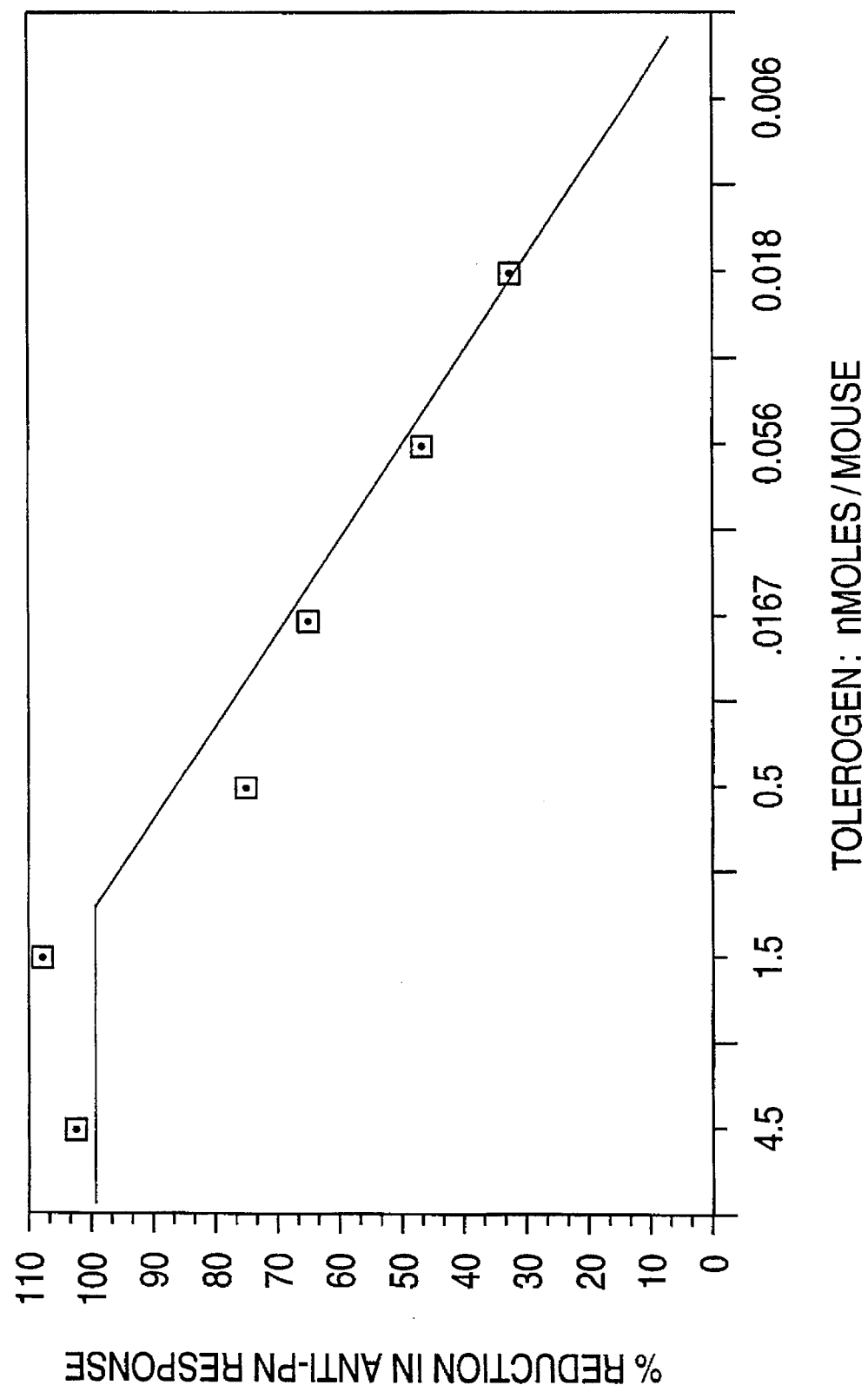
FIG. 5 shows the anti-PN response in mice primed with PN-KLH, treated with (PN)$_{20}$-HAD$_p$S-AHAB-TEG, Conjugate 20-IV, in the doses shown, then boosted with PN-KLH and bled 5 days later. Sera were tested by the Farr assay using radiolabeled PN at a concentration of $10^{-6}$M. There were 5 mice per group.

Because the 5' phosphate on the PN may be susceptible to enzymatic degradation, one of the oxygen molecules on the terminal phosphate was replaced with sulfur—thus the name $HAD_PS$. C57BL/6 mice were immunized with PN-KLH, A&P. After three weeks, groups of 5 mice/group were treated with different doses of Conjugate 20-IV, i.p.; one group was not treated. The groups were given booster injections and the sera were collected and assayed as described above. The results showing the percentage reduction in the anti-PN response are shown in FIG. 5. The anti-KLH responses of these mice (data not shown) were normal and were not significantly different that those shown in FIG. 2. These results show that this conjugate significantly reduced the anti-PN response.

Conjugate 20-IV Causes a Reduction in the Number of PN-specific Antibody Producing Cells C57Bl/6 mice were immunized with PN-KLH, A&P. After three weeks, groups of 3 mice/group were treated with different doses of Conjugate 20-IV, i.p.; one group was not treated. After five days, all of the mice were given a booster injection of PN-KLH in saline, i.p., and 4 days later their spleens were harvested and assayed for the number of PN-specific, IgG-producing cells using the hemolytic plaque assay. The results, shown in Table 5, show that this conjugate reduced the number of PN-specific IgG-producing cells.

TABLE 5

REDUCTION IN THE NUMBER OF pfc BY Conjugate 20-IV

| Group# | Dose μg/mouse | PN-specific pfc per $10^6$ spleen cells (Mean & S.E.) | % Reduction |
|---|---|---|---|
|   | None | 5889.4 (3444) |   |
| 2 | 274 | 3413 (1604) | 42 |
| 3 | 91 | 222 (752) | 96.2 |
| 4 | 30 | 1492 (2269) | 74.7 |
| 5 | 10 | 5421 (832) | 8 |
| 6 | 3 | 5077 (1946) | 13.9 |
| 7 | 1 | 7023 (679) | 0 |
| 8 | 0.4 | 4159 (2688) | 29 |

EXAMPLE 10

TREATMENT OF BXSB MICE WITH LJP 394, CONJUGATE 20-II

Mice Treatment Protocol

Six to 9 week old male BXSB mice (Jackson Laboratory, Bar Harbor, Me.) were housed at the La Jolla Pharmaceutical facility. Food and water were provided as libitum. Animals were rested one week prior to use. Initial blood samples and weights were obtained prior to the first conjugate treatment. Conjugate treatment was initiated at 7 to 9 weeks of age and was administered intravenously twice weekly from day 59 to day 150. Animals were bled periodically and their anti-DNA antibody titers were determined.

Assay for IgG Anti-DNA Antibody Production

Figure 15:
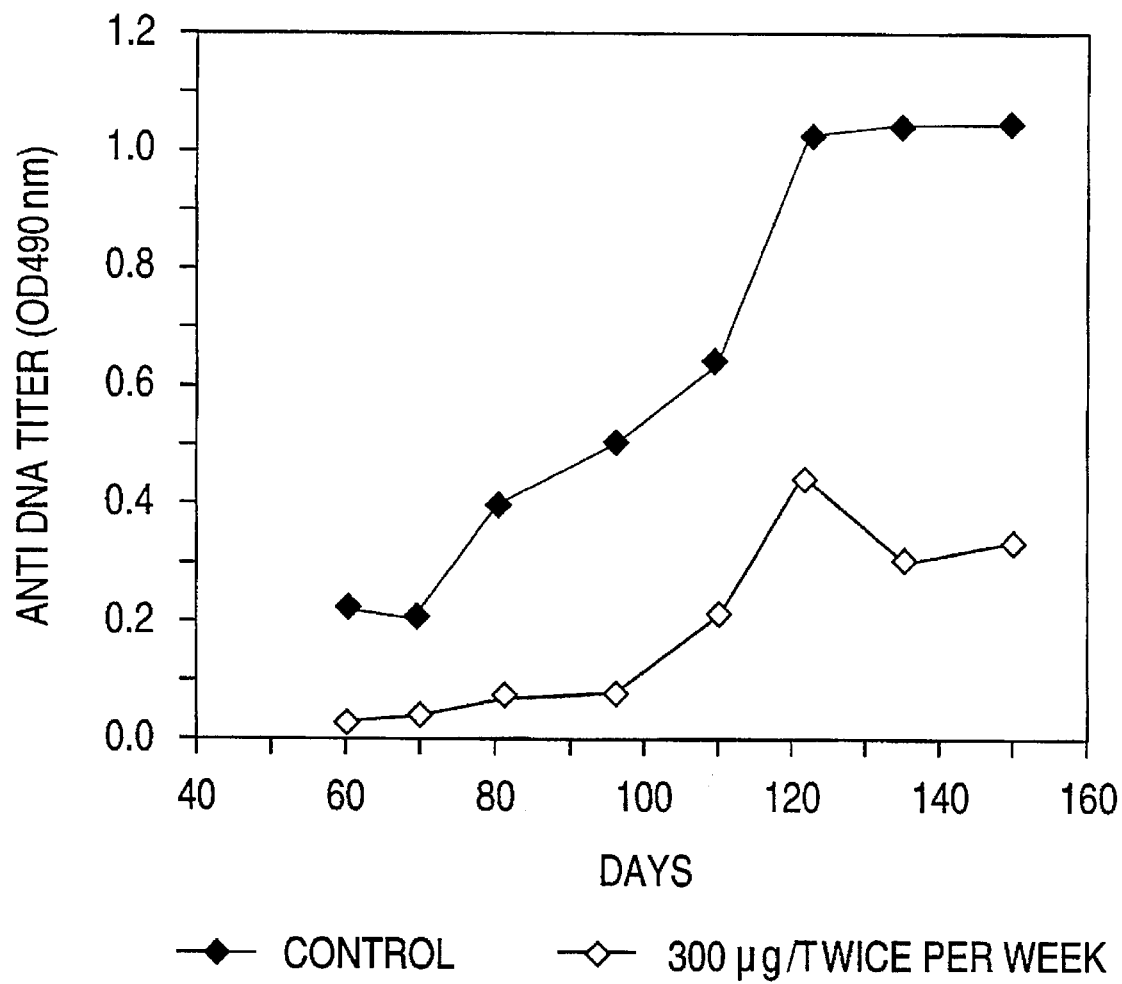
FIG. 15 illustrates the suppression of serum circulating IgG anti-DNA antibodies in male BXSB mice treated with LJP-394, Conjugate 20-II. An ELISA assay was used to measure IgG antibodies to (PN)$_{50}$ conjugated to D-EK. The serum from each of eight individual mice in each group was assayed.

A serum sample taken from each mouse was assessed for the presence of anti-DNA antibody by ELISA. Falcon Probind 96 well microtitration assay plates (Becton Dickerson, Oxnard, Calif.) were coated with 100 μL/well of $(PN)_{50}$-D-EK (a co-polymer of D-glutamic acid and D-lysine) at a concentration of 50 μg/mL overnight at 4° C. The plates were washed twice with PBS without calcium and magnesium and 0.05% Tween 20 (wash buffer) using a M96V plate washer (ICN Biomedical, Inc., Irvine, Calif.). Plates were blocked for 1 hour at room temperature in PBS containing 1% gelatin (Norland Products, Inc., New Brunswick, N.J.) and 0.05% Tween 20. Plates were washed twice with wash buffer before the addition of serum samples or standards. Serum samples and standards were prepared in a diluent containing PBS with 1% gelatin, 0.05% Tween 20 and 10% goat serum. Plates were incubated with serum samples for 60 to 90 minutes at 37° C. and then the wells were washed four times with wash buffer. Biotinylated goat anti-mouse IgG (Sigma Chemical Co., St. Louis, Mo.) was diluted 1/1000 in blocking solution containing 10% goat serum. The plates were incubated for 1 hour at 37° C. and washed four times. The substrate, OPD (Sigma Chemical Co., St. Louis, Mo.), was added. The plates were incubated in the dark until the highest reading of the highest standard was approximately 1 OD unit by an ELISA plate reader at OD 450 nm (Bio-Tek Instruments, Winooski, Vt.). The reaction was stopped with 50 μL of 3M HCl and the plates were read at 490 nm. The reference positive serum was included in each microtitration plate and the positive wells from each assay were within the sensitivity range of the reference curve 95% of the time. In the later bleeds, some positive samples exceeded the reference curve. However the most dilute mouse serum sample was within the range of the reference curve. No significant binding was observed by normal control negative serum. The results are shown in FIG. 15.

EXAMPLE 11

PREPARATION OF MELITTIN PEPTIDES AND CONJUGATE

The melittin molecule, composed of 26 amino acids, is one of the major components of bee venom. One third of the bee venom sensitive individuals have melittin specific antibodies. Melittin is highly immunogenic in some mouse strains (Balb/c, CAF1). The majority (>80%) of melittin specific antibodies in the responder mouse strains bind a B cell epitope which is the c-terminal heptapeptide of melittin.

Melittin $H_2N$-Gly-Ile-Gly-Ala-Val-Leu-Lys-Val-Leu-Thr-Thr-Gly-Leu-Pro-Ala-Leu-Ile-Ser-Trp-Ile-Lys-Arg-Lys-Arg-Gln-$CONH_2$ (SEQ. ID.: 1).

Melittin Peptides for T cell Stimulation

Melittin Peptide #1.

Ile-Lys-Arg-Lys-Arg-Gln-Gln-Gly ("7 mer") (SEQ. ID NO.: 2).

Melittin Peptide #2.

Trp-Ile-Lys-Arg-Lys-Arg-Cln-Cln-Gly ("8 mer") (SEQ. ID NO.: 3).

Melittin Peptide #3.

Ser-Trp-Ile-Lys-Arg-Lys-Arg-Cln-Gln-Gly ("9 mer") (SEQ ID NO.: 4).

Melittin Peptide #4.

Ile-Ser-Trp-Ile-Lys-Arg-Lys-Arg-Gln-Gln-Gly ("10 mer") (SEQ. ID NO.: 5).

Melittin Peptide #5.

Cys-Ile-Ser-Trp-Ile-Lys-Arg-Lys-Arg-Gln-Gln-Gly ("11 mer") (SEQ. ID NO.: 6).

Peptide Synthesis

Melittin peptides were synthesized using standard Fmoc chemistry techniques on a glycine resin (Advanced ChemTech #SG5130 or equivalent (Advanced ChemTech, 2500 Seventh Street Road, Louisville, Ky.) using 2.3M excess amino acid derivatives for each coupling step. Completion of the coupling was monitored with bromphenol blue and confirmed with ninhydrin.

Melittin Peptides Used in Conjugations

Melittin Peptide #6.

$H_2N$-Cys-Trp-Ile-Lys-Arg-Lys-Arg-Gln-Gln-Gly-$CO_2H$ (SEQ. ID NO.: 7).

Melittin Peptide #7.

$H_2N$-Trp-Ile-Lys-Arg-Lys-Arg-Gln-Cln-Lys-Cys-Gly-$CO_2H$ (SEQ. ID NO.: 8 ).

Melittin Peptide #8.

($H_2N$-Trp-Ile-Lys-Arg-Lys-Arg-Gln-Gln$)_2$-Lys-Cys-Gly-$CO_2H$ (SEQ. ID NO.: 10).

A cysteine was added as required for coupling certain peptides via a thioether bond to the valency platform molecule. Peptides were purified by reversed phase HPLC following synthesis and lyophilized to dryness. The appropriate amount of peptide was then weighed out for each conjugation.

Reduction of Preformed Disulfide Bonds: (Tributylphosphine Method)

All buffers were sparged with helium. The peptide was dissolved in a minimal volume (approximately 10 to 20 mg/mL) of 0.05M $NaHCO_3$ (pH 8.25). A 1 mL solution of 0.7M tributylphosphine (TBP; MW=202.32 g/mole; d-0.812 g/mL) was prepared by adding 174.4 µL of TBP to 825.6 µL of isopropanol (iPrOH). Then, 1:1 equivalents of TBP were added to the peptide solution prepared as described above, mixed well, and allowed to react for 30 minutes to 1 hour with occasional mixing to keep TBP dissolved and/or dispersed in the solution. Complete reduction was confirmed by HPLC.

Conjugation of Peptides to Valency Platform Molecules #3 or #60:

All buffers were sparged with helium. The polyethylene glycol (PEG) derivative #3 or #60 was dissolved in a minimal volume (approximately 20 mg/mL) of 0.05M $NaHCO_3$ (pH 8.25). Approximately 3 equivalents of peptide were used per iodacetyl group on the PEG derivative. For para-aminobenzoic acid (PABA)-PEG; 2 iodacetyl groups; MW=approximately 4100 g/mole; 6 equivalents of peptide were used for each equivalent of PABA-PEG. For diaminobenzoic acid (DABA)-PEG; 4 iodoacetyl groups; MW=approximately 4300 g/mole; 12 equivalents of peptide were used for each equivalent of DABA-PEG. The PEG solution was added to the reduced peptide solution and allowed to react for at least one hour in the dark. The peptide conjugate was purified by preparative HPLC. Before pooling and lyophilization, fractions were checked by electrophoresis using a 15% tricine gel.

TABLE 6

Conjugates of melittin Peptides and PEG

| Conjugate number | Valence platform | Peptide conjugated | # B cells epitopes/ molecule | Conjugation terminus | Conju- by peptide conjugate[1] |
|---|---|---|---|---|---|
| 1 | 60 | 6 | 2 | N | no(pep) |
| 2 | 3 | 6 | 4 | N | no(pep/conj) |
| 3 | 3 | 7 | 4 | C | nd |
| 4 | 3 | 5 | 4 | N | yea(pep) |
| 5 | 3 | 8 | 8[2] | C | nd |

[1]Stimulation of uptake of [$^3$H] thymidine by cultured T cell from melittin-immunized mice; nd = not determined; pep = peptide tested; conj = peptide-PEG conjugate tested.
[2]4 copies of a branched peptide, containing two identical branches each; each branch comprising a B cell epitope Murine Lymph Node Proliferation Assays.

Female Balb/c mice (6–8 weeks old; Jackson Laboratory, Bar Harbor, Me.) were obtained and housed at the La Jolla Pharmaceutical animal facility according to National Institutes of Health guidelines. Food and water was provided ad libitum. Balb/c mice were immunized in each hind footpad with 50 µg of melittin molecule in Complete Freund's Adjuvant (CFA) (Sigma Chemical Co., St. Louis, Mo.). Popliteal lymph nodes were harvested aseptically seven days later. Lymph nodes were gently dissociated by teasing the cells through a 50 mesh sieve screen. The single cell suspension was washed in RPMI-1640 (Irvine Scientific, Irvine Calif.) containing glutamine, penicillin and streptomycin. $5\times10^5$ cells in RPMI medium supplemented with 10% fetal bovine serum (FCS) in quadruplicate wells of round bottom 96-well Corning microtitration plates were cultured with melittin or a melittin peptide at 10, 1.0 or 0.1 µg/mL. Cells in the positive control wells were cultured with murine interleukin 2 (IL-2) at 100 or 50 U/mL, PHA (phytohemagglutinin) at 1 µg/mL. The negative control wells contained lymph node cells in RPM-1640 and 10% FCS. The cells were cultured for 4 days in a 37° C. incubator with 5% $CO_2$. Each well was pulsed with 1 µCi of [$^3$H] thymidine (ICN Biochemicals, Costa Mesa, Calif.) for an additional 18 hours. Cells were harvested onto a glass fiber filter mat using a semiautomatic cell harvester (Scatron, Sterling, Va.). Incorporation of [$^3$H]thymidine was determined by liquid scintillation. The results were expressed as average counts per minute.

In vivo Protocols

Balb/c mice were primed intraperitoneally (i.p.) with 4 µg of melittin in CFA. One month later the potential tolerogen or formulation buffer was administered i.p. Three days later all mice received an i.p. injection of 4 µg of melittin in Incomplete Freund's Adjuvant (ICF) (Sigma Chemical Co., St. Louis, Mo.). 100 to 200 µL of blood was collected from the retro-orbital venous plexus 10 days later. Serum samples were assayed for anti-peptide or anti-melittin IgG antibodies.

Assay for IgG Anti-Melittin or Total Anti-Melittin Antibodies

An individual mouse's serum sample was assessed serially for the presence of anti-melittin antibodies by ELISA. Falcon Probind 96-well microtitration plates were precoated with 10 µg/mL melittin or melittin peptide in phosphate buffered saline (PBS), pH 7.2, overnight at 4°. The plates were washed twice with a wash solution containing PBS, 0.02% Tween-20, and 1% gelatin (Norland Products Inc., New Brunswick, N.J.). Plates were blocked with 200 µL PBS containing 5% gelatin for 1 hour at 37°. Serum samples were prepared in a diluent of PBS containing 5% gelatin. Samples were tested at dilutions of 1:100 to 1:1000. After 1 hour of incubation at 37° C., the plates were washed four times. ExtraAvidin peroxidase (Sigma Chemical Co., St. Louis, Mo.) was diluted 1:1000 in PBS containing 5% gelatin. The plates were incubated 30 minutes at 37° C. and then washed five times. Wells were developed with o-phenylenediamine (OPD) (Sigma Chemical Co., St. Louis, Mo.) in the dark for 15–30 minutes, the reaction was stopped with 3M HCl.

The optical density (OD) was determined at 450 nm on a microplate reader (Bio-tek Instruments, Winooski, Vt.).

Antibody Forming Cell Assay

Cellulose microtitration plates (Millipore Co., Bedford, Mass.) were prepared as indicated above for the IgG antibody (ELISA) assay. However, at the point in the assay where the serum samples were added to the wells, splenic cells (5×10⁵/well) were added instead of serum, and incubated overnight. The remainder of the ELISA assay was performed as indicated above.

T Cell Epitopes

Figure 8:
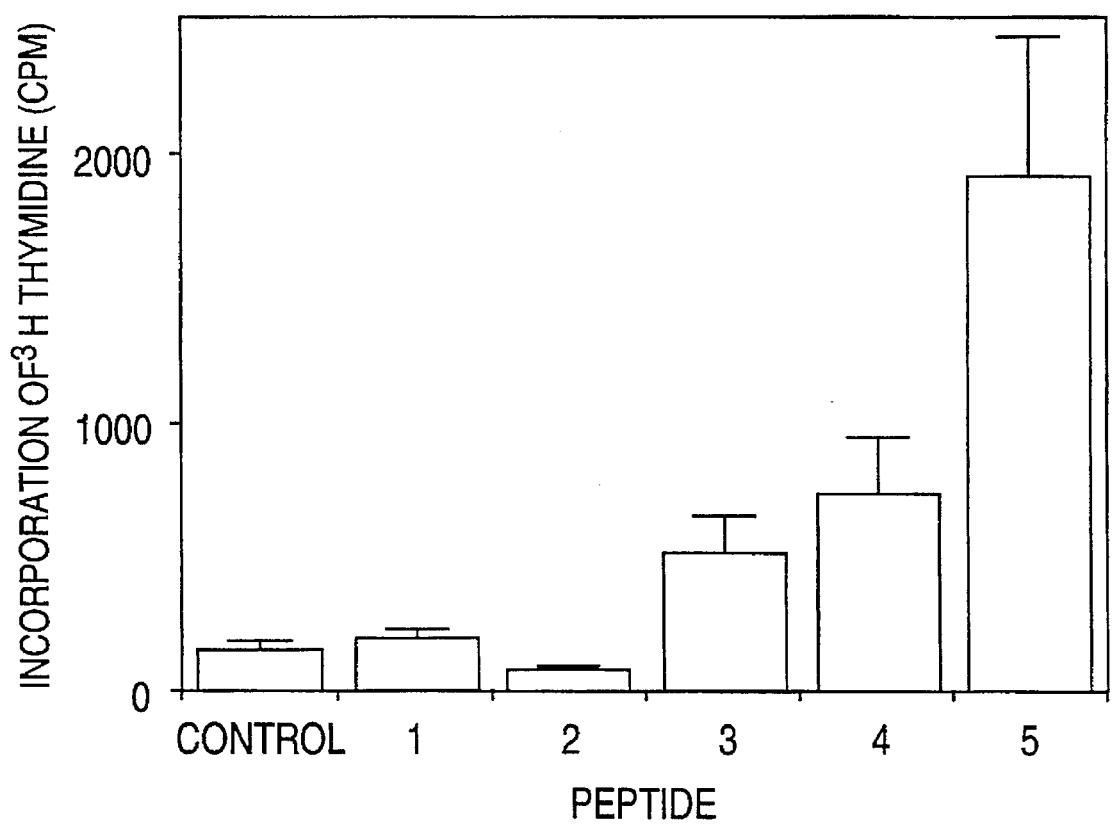
FIG. 8 compares the level of T cell proliferation induced by melittin peptides.

T Cells from mice primed with melittin showed T cell proliferation in response to the whole melittin molecule and to C-terminal melittin peptides 3, 4, and 5 (FIG. 8). However, C-terminal peptides 1 and 2 induced no significant T cell proliferation. Melittin peptides 2 and 5 were conjugated to PEG. Like melittin peptide 2, the PEG conjugate of melittin peptide 2 also did not induce significant T cell proliferation.

Figure 9:
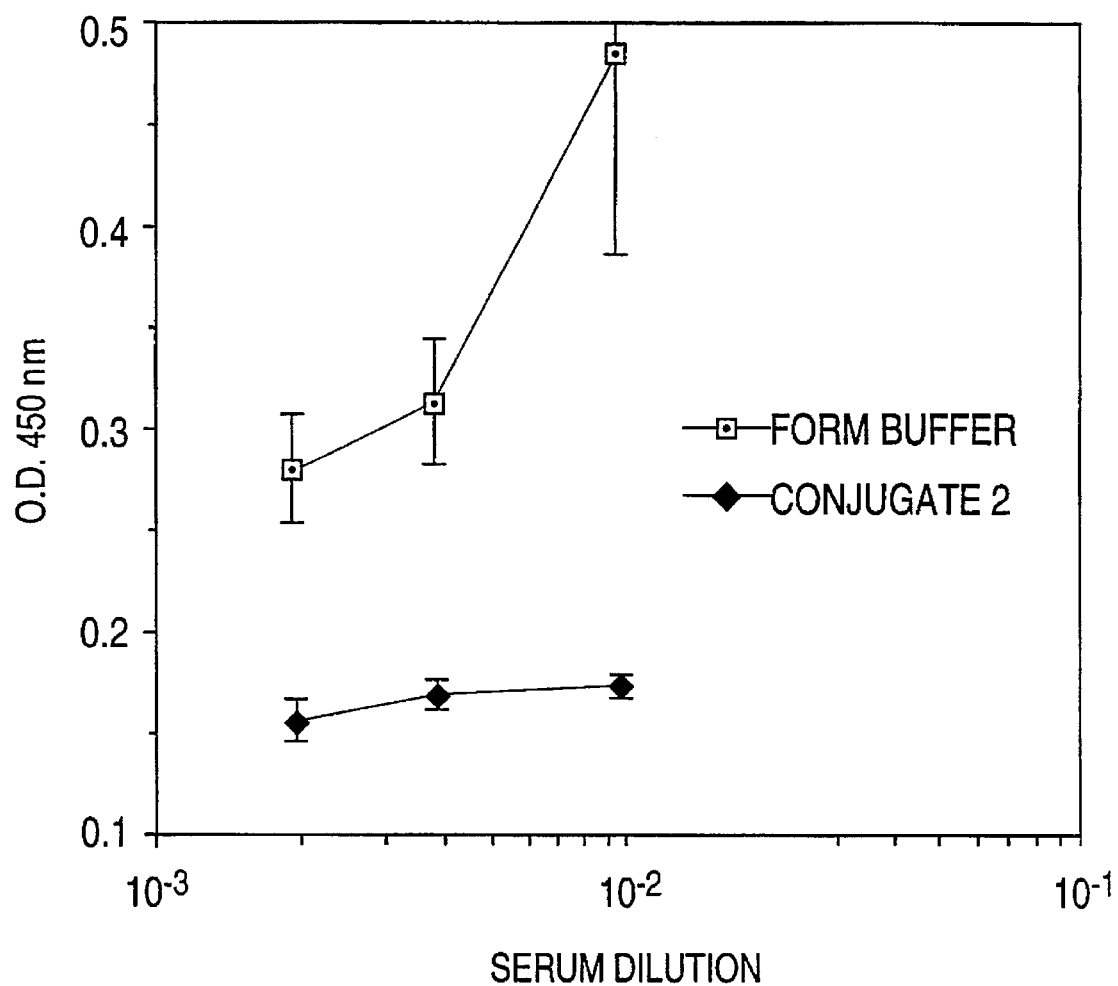
FIG. 9 compares the levels of anti-melittin peptide 2 antibodies produced in mice treated with melittin peptide Conjugate 2 versus the control mice treated with formulation buffer.
Figure 10:
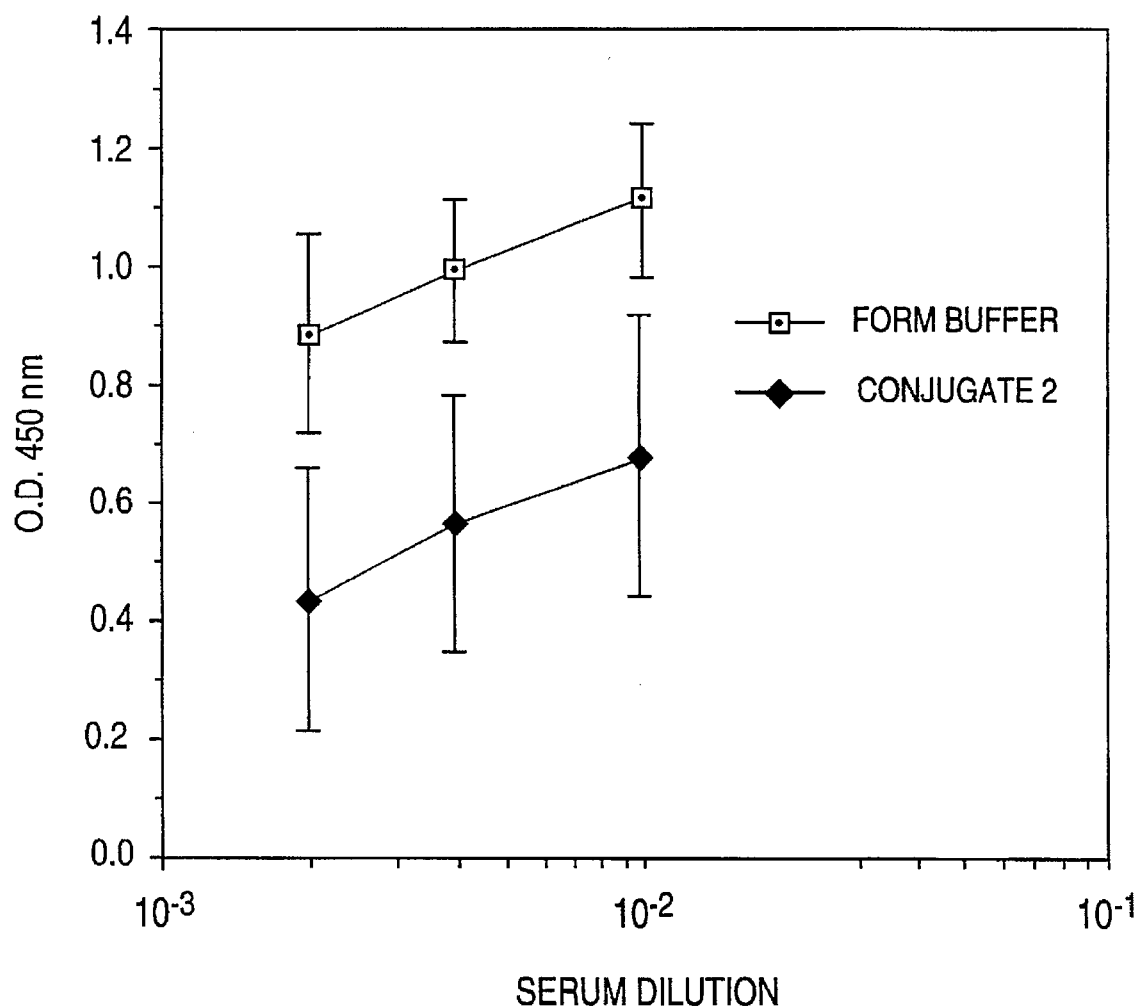
FIG. 10 compares the levels of anti-melittin antibodies produced in mice treated with melittin peptide Conjugate 2 versus the control mice treated with formulation buffer.
Figure 11:
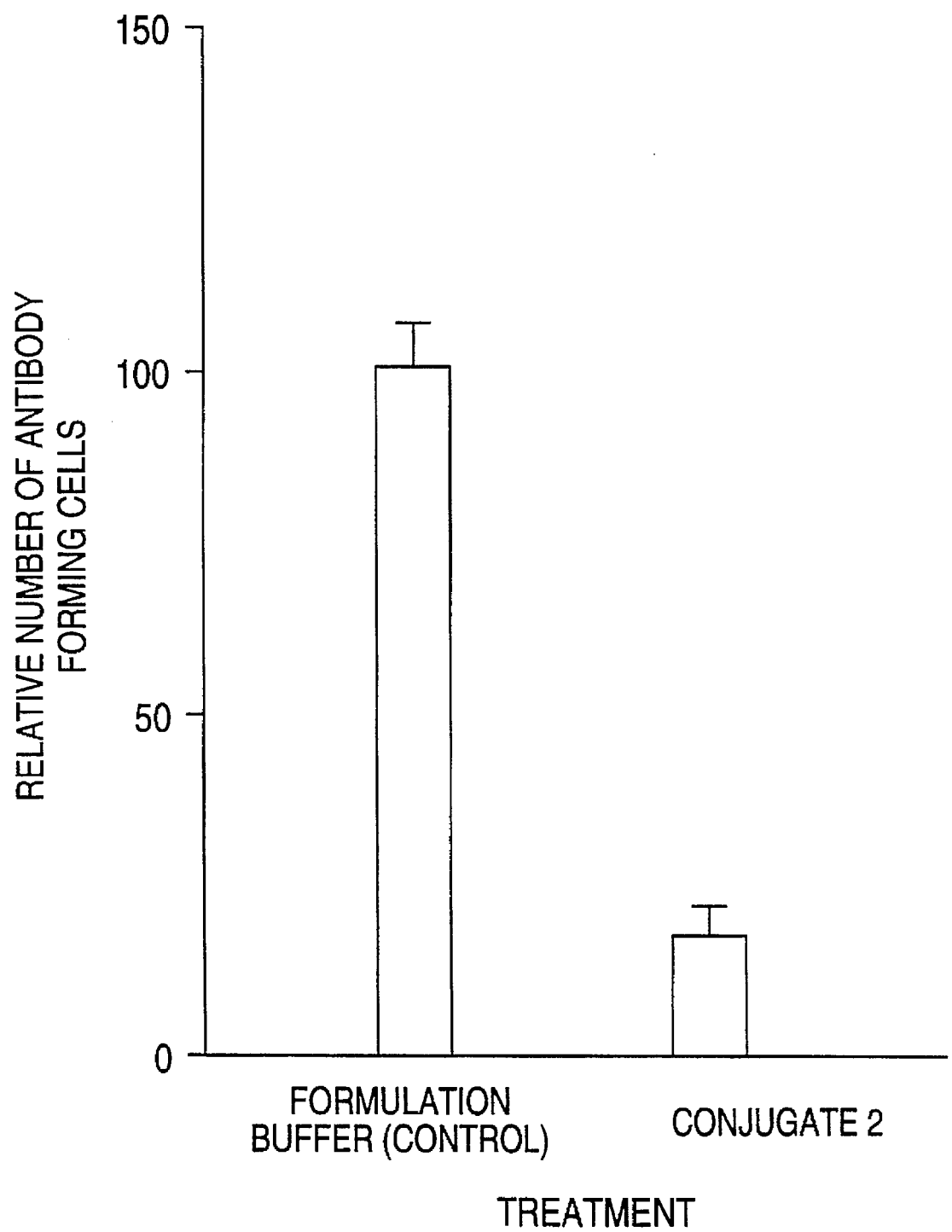
FIG. 11 compares the levels of anti-melittin peptide 2 antibody-forming cells in mice treated with melittin peptide Conjugate 2 versus the control mice treated with formulation buffer.
Figure 12:
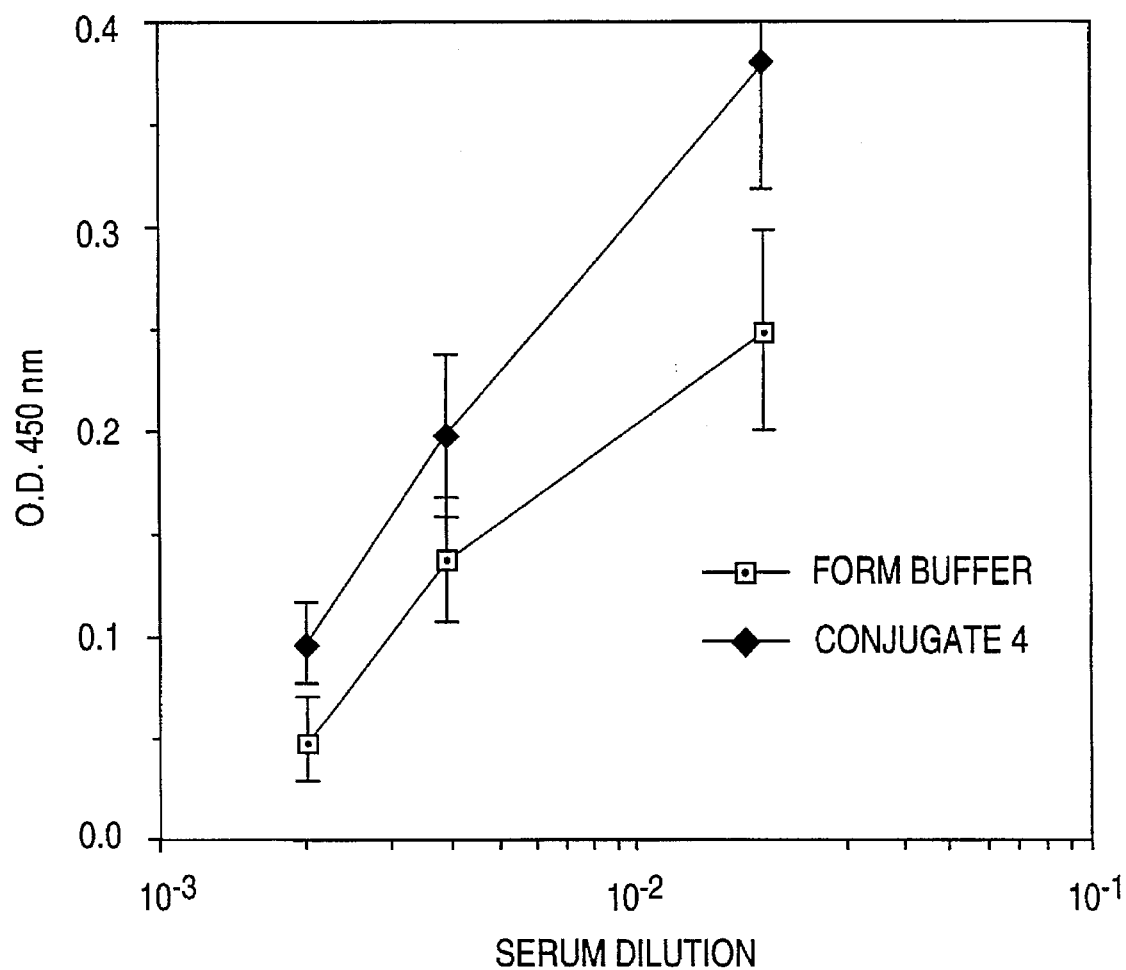
FIG. 12 illustrates that melittin peptide Conjugate 4, a conjugate of peptide #5 which contains a T cell epitope, was not a tolerogen.
Figure 14:
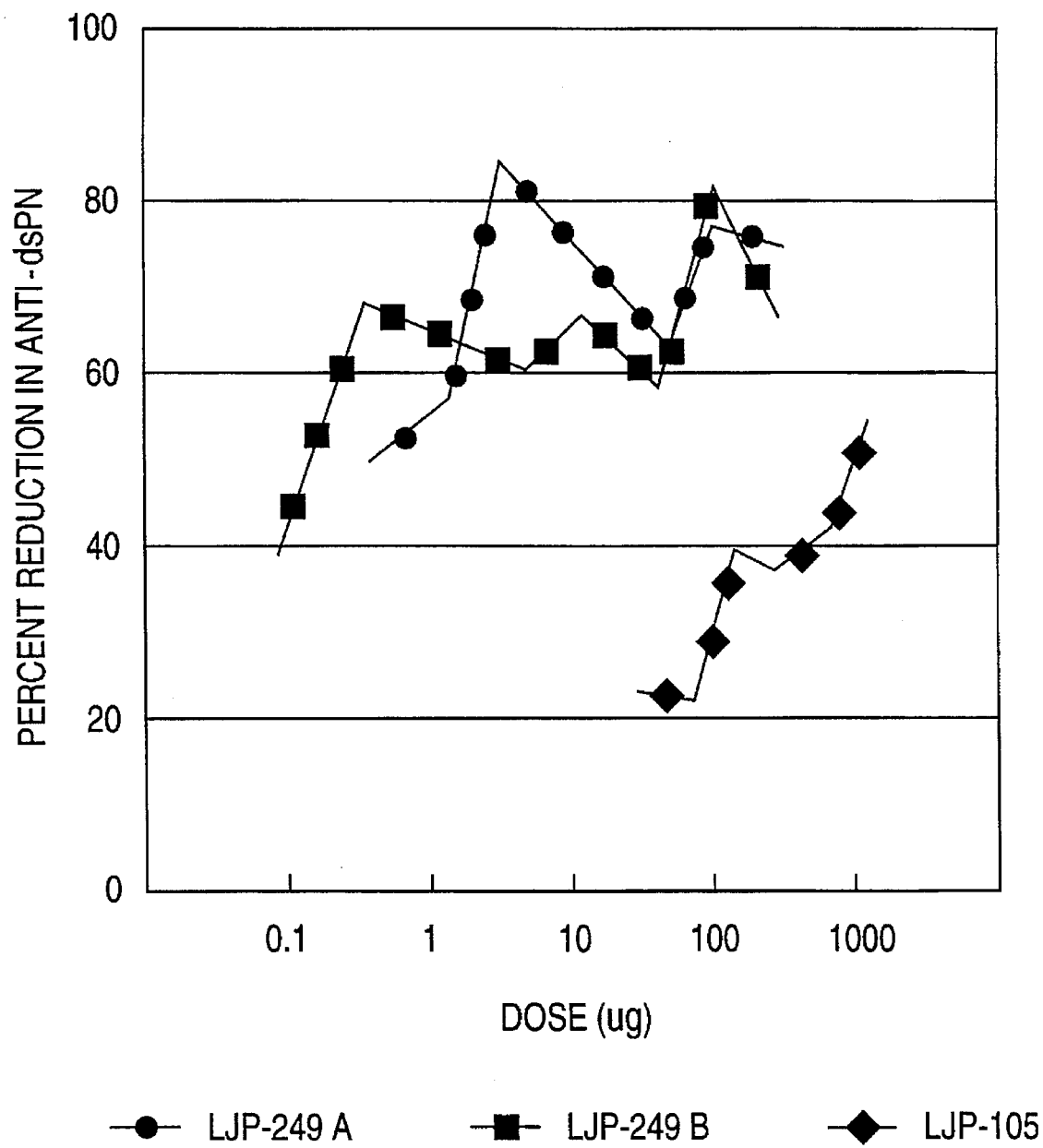
FIG. 14 illustrates the increase in the percentage of reduction in anti-dsPN antibody achieved by conjugates within the present invention LJP-249A and LJP-249B which are Conjugate 3-II compared to a prior art conjugate (LJP-105) comprising D-EK and (PN)$_{50}$.

Studies Using Melittin Conjugated Peptides to Tolerize Mice Primed and Boosted with Melittin Mice treated with the conjugate prepared as described above (10 mg/kg, 200 µg/mouse), had significantly lower levels of anti-melittin peptide 2 antibodies (FIG. 9) and also lower levels of anti-melittin antibodies (FIG. 10) as compared to the control Balb/c mice treated with formulation buffer. Spleen cells from mice treated with buffer control or the conjugate were assayed for the ability of antibody-forming cells to produce anti-melittin or anti-melittin peptide 2 antibodies as measured in a soluble ELISA assay. As shown in FIG. 11, the levels of anti-melittin peptide 2 antibody forming cells in the Conjugate 2 treatment group were significantly lower than in the control group which was administered formulation buffer. Mice treated with Conjugate 4, a conjugate of peptide 5 which contains a T cell epitope, failed to reduce the titer of antibodies to peptide 5 in treated mice. Thus, the conjugate containing a T cell epitope was not a tolerogen (FIG. 12). In fact, rather than reduce the response, the levels of anti-peptide antibody may have increased slightly.

EXAMPLE 12

Additional Studies Using Melittin Peptide Conjugates to Tolerize Mice Primed and Boosted With Melittin Female C57BL/6 mice, ages 5 to 8 weeks were purchased from The Jackson Laboratory, Bar Harbor, Me. Animals were maintained and treated accordingly to National Institutes of Health guidelines.

Immunization Protocol

Mice were primed by an i.p. injection containing 5 µg of melittin precipitated on alum and 2×10⁹ B. pertussis (Michigan Department of Public Health, Lansing, Mich.) as an adjuvant. The mice were boosted with 5 µg of melittin, i.p., in PBS.

pfc Assay

Sheep Red Blood Cells (SRBC) (Colorado Serum Co., Denver, Colo.) were conjugated with melittin-peptide 2 using carbodiimide. Fresh SRBC (less than 2 weeks old) were washed four times with cold saline and one time with mannitol (0.35M mannitol, 0.01M NaCl). The SRBC were suspended in mannitol to a concentration of 10% (v/v). 100 µL of mannitol containing 30 µg of melittin peptide #3 were added to 1 mL aliquots of 10% SRBC which were then incubated on ice for 10 minutes. 100 µL of a 100 mg/mL solution of 1-ethyl-3 (3-dimethylaminopropyl)-carbodiimide HCl (EDCI) was then added and incubated on ice for 30 minutes. The SRBC were washed twice with Balanced Salt Solution (BSS) (Irvine Scientific Co, Irvine, Calif.) and resuspended to 10% (v/v). Lyophilized guinea pig complement (GIBCO, New York, N.Y.) was reconstituted with BSS and then diluted 1:3 with BSS. One mL of the diluted guinea pig complement was added to 3 mL of conjugated SRBC. Rabbit anti-mouse IgG was added to give a final dilution of 1:100 of the rabbit antiserum. This concentration was predetermined to inhibit all IgM pfc while enhancing the maximum number of IgG pfc. An equal volume of this complement/anti-mouse IgG/SRBC suspension was mixed with a cell suspension of mouse spleen cells taken from a single mouse. 50 µL of each mixture was transferred to the chambers of a Cunningham slide (three chambers per slide). The edges were then sealed with paraffin and incubated at 37° C. for one hour. The number of plaques per chamber was counted with the aid of a dissecting microscope. Each spleen suspension was also assayed using non-conjugated SRBC as a control. The number of viable cells, in each spleen cell suspension, was determined. The number of pfc per 10⁶ spleen cells was determined for each chamber and the mean of the triplicates calculated. The number of pfc for non-conjugated SRBC was subtracted from the number of pfc for conjugated SRBC to determine the number of peptide-specific pfc.

Determining The Optimal Time to Measure pfc

Mice were primed with melittin. Groups (3 mice per group) of primed mice were boosted with melittin on days 2, 4, 6, and 8. On day 10 the mice were sacrificed and their spleens harvested. Cell suspensions were prepared and assayed for the number of peptide specific pfc determined. The optimal number of pfc was obtained 6 days after boosting with melittin.

The Orientation of The peptide on The PEG Conjugate Does Not Affect The Conjugate's Ability to Induce Tolerance Two different tolerogens were constructed to determine if the orientation of the peptide on the PEG conjugate affects its ability to induce tolerance. The peptide was covalently bound to valency platform molecule 3 through its C-terminal end to make melittin conjugate 3. Groups (3/group) of mice primed with melittin were treated, i.p., with conjugates or with saline. Five days later all of the mice, including the non-treated control group, were boosted with 5 µp of melittin. Six days later the mice were sacrificed, their spleens were harvested and the number of peptide specific pfc determined. As illustrated in Table 6, both orientations were effective in reducing the number of peptide-specific pfc/10⁶ spleen cells in mice primed and boosted with the parent protein Melittin.

TABLE 7

Orientation of the peptide on the PEG conjugate does not affect the conjugates' ability to induce tolerance

| Melittin Conjugate# | µg/mouse | Peptide specific pfc per 10⁶ spleen cells (Mean and S.D.) | % Reduction |
|---|---|---|---|
| 3 | 1000 µg | 386 (85) | 86.8% |
| " | 500 µg | 489 (one mouse) | 83.3% |
| " | 250 µg | 957 (298) | 67.3% |
| 2 | 1000 µg | 546 (160) | 81.3% |
| " | 500 µg | 866.6 (235) | 70.4% |
| " | 250 µg | 1280 (one mouse) | 56.2% |
| None | None | 2924 (164) | — |

The Number of Peptides per PEG Conjugate Does Affect The Conjugate's Ability to Induce Tolerance Three different conjugates, each with a different number of peptides per PEG conjugate, were constructed to determine if the ratio of peptides to PEG molecule was important. Conjugate 1 had only two peptides per PEG conjugate.

Another had four peptides per PEG conjugate (Conjugate 2). The third had eight peptides per PEG conjugate (Conjugate 5). Groups (3/group) of mice primed with melittin were treated, i.p., with the different conjugates or with saline. Five days later all of the mice, including the non-treated control group, were boosted with 5 µg of melittin. Six days later, the mice were sacrificed, their spleens were harvested and the number of peptide-specific pfc determined. As shown in Table 8, Conjugate 1, containing two peptides per PEG molecule, was ineffective in reducing the number of peptide-specific pfc/$10^6$ spleen cells in mice primed and boosted with the parent protein melittin. The results show that both melittin conjugates 2 and 5 were effective as tolerogens; however, conjugate 5, which contained 8 peptides, was effective at a lower dose than conjugate 2 which contained four peptides per valency platform molecule.

TABLE 8

The number of peptides per PEG conjugate does affect the conjugates' ability to induce tolerance

| Treatment Molecule | Dose µg/mouse (nMoles) | Peptide specific indirect IgG pfc (SD) | % Reduction |
|---|---|---|---|
| No treatment | | 1159 (280) | std |
| Conjugate 1 | 1000 (217) | 1290 (98) | −11% |
| | 250 (54) | 1350 (206) | −16% |
| Conjugate 2 | 500 (80) | 585 (125) | 49.5% |
| | 250 (40) | 1001 (176) | 14% |
| Conjugate 5 | 500 (53) | 630 (325) | 45.6% |
| | 250 (26.5) | 443 (105) | 61.8% |
| | 125 (13.25) | 583 (69) | 49.7% |

Modifications of the above-described modes for carrying out the invention that are obvious to those of skill in the fields of polynucleotide chemistry, conjugation chemistry, immunology and related fields are intended to be within the scope of the following claims.

We claim:

1. A chemically-defined, non-polymeric valency platform molecule of the formula:

$$G^{[7]}\{O-C(=O)-N(Q^{[7]}(T^{[7]})_{p^{[7]}/2})_2\}_{n^{[7]}} \quad \text{Formula 7}$$

wherein $G^{[7]}$ is —$CH_2CH_2$—O—$CH_2CH_2$—O—$CH_2CH_2$—;

$Q^{[7]}$ is —$CH_2CH_2$—NH—C(=O)—$(CH_2)_5$—NH—C(=O)—;

each of the ($p^{[7]} \times n^{[7]}$) moieties shown as $T^{[7]}$ is $R^{ALK}X$;

each X is independently a halogen of atomic number greater than 16 and less than 54 or other good leaving group;

each $R^{ALK}$ is independently a linear, branched, or cyclic alkyl (1–20C) group;

$n^{[7]}=2$; and $p^{[7]}=2$.

* * * * *